(12) United States Patent
Hirotsune

(10) Patent No.: US 9,539,298 B2
(45) Date of Patent: *Jan. 10, 2017

(54) LISSENCEPHALY THERAPEUTIC AGENT

(71) Applicant: OSAKA CITY UNIVERSITY, Osaka (JP)

(72) Inventor: Shinji Hirotsune, Osaka (JP)

(73) Assignee: OSAKA CITY UNIVERSITY, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/074,142

(22) Filed: Mar. 18, 2016

(65) Prior Publication Data

US 2016/0250276 A1 Sep. 1, 2016

Related U.S. Application Data

(63) Continuation-in-part of application No. 13/988,843, filed as application No. PCT/JP2011/078000 on Nov. 28, 2011, now Pat. No. 9,371,359.

(30) Foreign Application Priority Data

| Nov. 29, 2010 | (JP) | 2010-264763 |
| Oct. 4, 2011 | (JP) | 2011-220480 |

(51) Int. Cl.

| C07K 5/062 | (2006.01) |
| C07K 5/083 | (2006.01) |
| A61K 31/27 | (2006.01) |
| A61K 31/351 | (2006.01) |
| A61K 38/00 | (2006.01) |
| A61K 38/05 | (2006.01) |
| A61K 9/00 | (2006.01) |

(52) U.S. Cl.
CPC ............. *A61K 38/05* (2013.01); *A61K 9/0019* (2013.01); *A61K 9/0053* (2013.01)

(58) Field of Classification Search
None
See application file for complete search history.

(56) References Cited

U.S. PATENT DOCUMENTS

| 2007/0004643 A1 | 1/2007 | Shirasaki et al. |
| 2013/0244945 A1 | 9/2013 | Hirotsune |

OTHER PUBLICATIONS

Yamada et al., "Inhibition of calpain increases LIS1 expression and partially rescues in vivo phenotypes in a mouse model of lissencephaly," Nature Medicine, vol. 15, No. 10, pp. 1202-1207, Oct. 2009.
Wynshaw-Boris et al., "Lissencephaly: Mechanistic insights from animal models and potential therapeutic strategies," Seminars in Cell & Developmental Biology, vol. 21, pp. 823-830, available online Aug. 3, 2010.
Takitoh et al., "Inhibiton of calpain increases LIS1 and partially rescues in vivo phenotypes in LIS1 mutant mice: a potential therapy for lissencephaly," Journal of Japanese Biochemical Society, Abstract, p. 3P-0426, 2008.
Hirotsune, "Inhibition of calpain increases LIS1 and partially rescues in vivo phenotypes in LIS1 1 mutant mice: a potential therapy for lissencephaly," Journal of Japanese Biochemical Society, Abstract, p. 2S2a-3, 2009.
Yamada et al., "Inhibition of calpain increases LIS1 (PAFAH1B1) and partially rescues in vivo phenotypes in a mouse model of lissencephaly," Annual Meeting of the Molecular Biology Society of Japan Koen Yoshishu, vol. $32^{nd}$, No. vol. 2, p. 141, 2P-0404, Oct. 2009.
Shinji, "Development of novel treatment for lissencephaly through elucidation of molecular mechanism," Boshi Kenko Kyokai Shoni Igaku Josei Kenkyu Hokokusho, vol. $21^{st}$, pp. 19-22, Jun. 2010.

(Continued)

*Primary Examiner* — Adam M Weidner
(74) *Attorney, Agent, or Firm* — Foley & Lardner LLP

(57) ABSTRACT

An object of the present invention is to provide a medicament and method for treating lissencephaly patients. The present invention provides a lissencephaly therapeutic or preventive agent comprising a compound represented by the general formula (I):

[Chem 1]

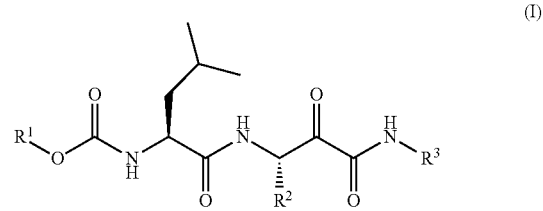

(I)

wherein $R^1$ is lower alkyl substituted with lower alkoxy, lower alkyl substituted with a heterocyclic group, a heterocyclic group, or a group represented by the formula (IIa):

[Chem 2]

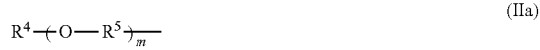

(IIa)

wherein $R^4$ is lower alkyl, $R^5$ is lower alkylene, and m is an integer of 1 to 6;

$R^2$ is lower alkyl optionally substituted with phenyl; and $R^3$ is lower alkyl optionally substituted with halogen, lower alkoxy, or phenyl; condensed polycyclic hydrocarbon; or hydrogen.

11 Claims, 24 Drawing Sheets

(56) References Cited

OTHER PUBLICATIONS

Sorimachi, "Diseases caused by calpain deficiency," Medical Science Digest, vol. 36, No. 3, pp. 706-710, vol. 36, No. 3, Mar. 2010.
Shumueli et al., "Platelet-Activating Factor (PAF) Acetylhydrolase Activity, LIS1 Expression, and Seizures," Journal of Neuroscience Research, vol. 57, pp. 176-184, 1999.
Morris et al., "The lissencephaly gene product Lis1, a protein involved in neuronal migration, interacts with a nuclear movement protein, NudC," Current Biology, vol. 8, pp. 603-606, 1998.
Reiner et al., "Lissencephaly Gene (LIS1) Expression in the CNS Suggests a Role in Neuronal Migration," The Journal of Neuroscience, vol. 15, No. 5, pp. 3730-3738, May 1995.
International Search Report issued in application No. PCT/JP2011/078000 on Dec. 27, 2011.
Komura et al., "A Novel Calpain Inhibitor, ((1S)-1((((1S)-1-Benzyl-3-Cyclopropylamino-2,3-DI-Oxopropyl)Annino) Carbonyl)-3-Methylbutyl) Carbamic Acid 5-Methoxy-3-Oxapentyl Ester, Protects Neuronal Cells From Cerebral Ischemia-Induced Damage in Mice," Neuroscience, vol. 157, pp. 309-318, 2008.
Takahashi et al., "Retinal distribution of SNJ-1945 by micro-autoradiography," The $18^{th}$ International Congress for Eye Research, P432, Sep. 24-29, 2008, Bejing, China.
Toba et al., "Post-natal Treatment by a blood-brain-barrier permeable calpain inhibitor, SNJ1945 rescued defective function in lissencephaly", Scientific Reports, vol. 3, Article No. 1224, Feb. 6, 2013, 10 pages.
Yamada et al., "Therapeutic Intervention for Genetic Disease by the Augmented Recycling of Target Proteins"; Editorial, Future Neurology, vol. 5, Issue 1, Jan. 2010, pp. 5-8.
Office Action issued on May 27, 2014 in U.S. Appl. No. 13/988,843 (US 2013/0244945).
Office Action issued on Oct. 29, 2014 in U.S. Appl. No. 13/988,843 (US 2013/0244945).
Office Action issued on May 14, 2015 in U.S. Appl. No. 13/988,843 (US 2013/0244945).
Notice of Allowance issued on Nov. 25, 2015 in U.S. Appl. No. 13/988,843 (US 2013/0244945).
Notice of Allowance issued on Mar. 15, 2016 in U.S. Appl. No. 13/988,843 (US 2013/0244945).

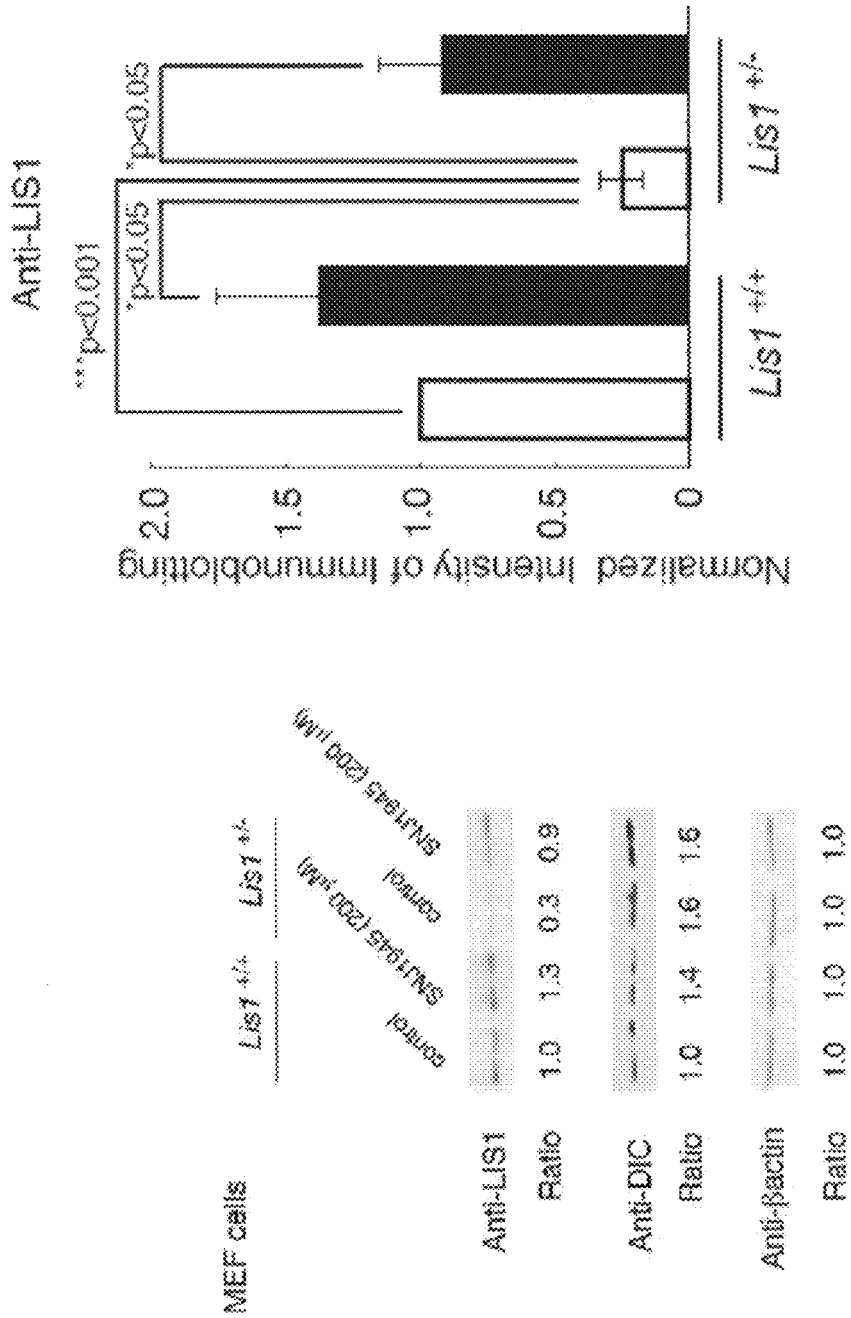

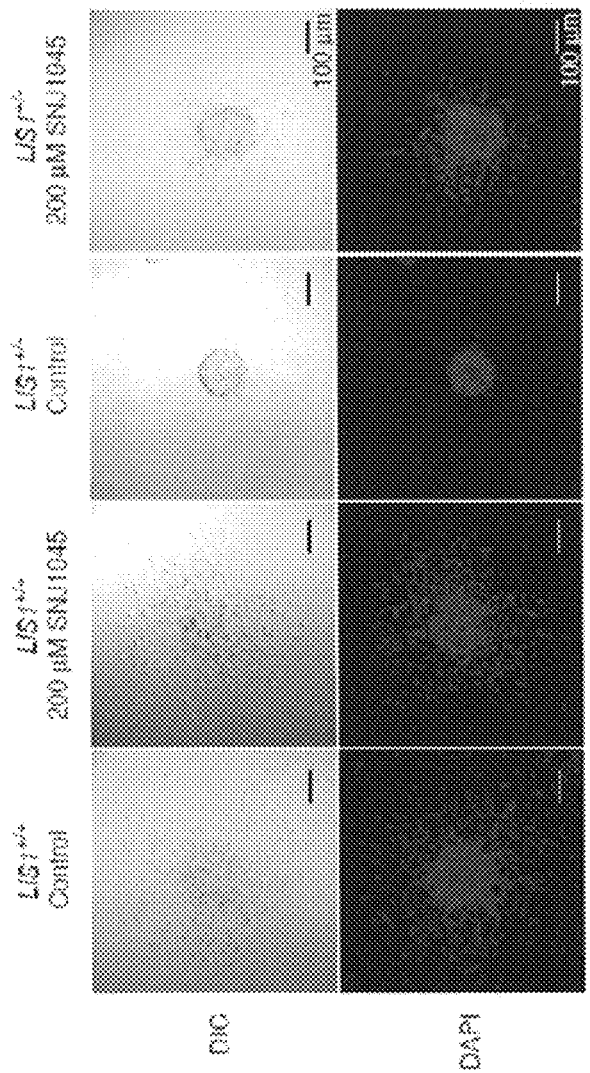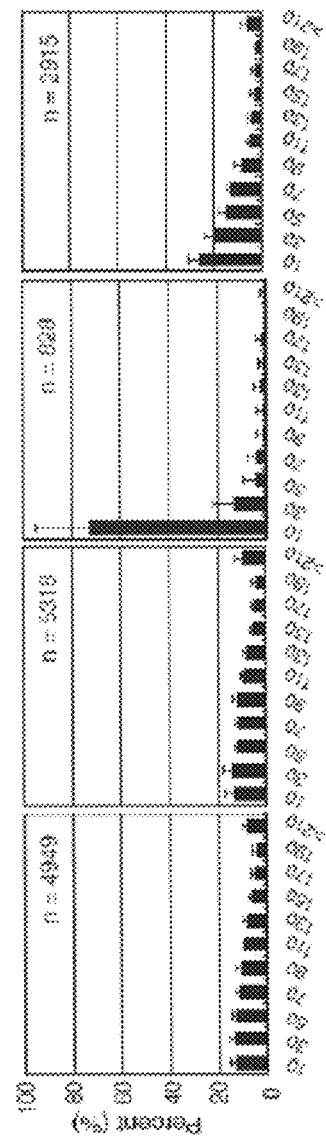
FIG. 5A
FIG. 5B

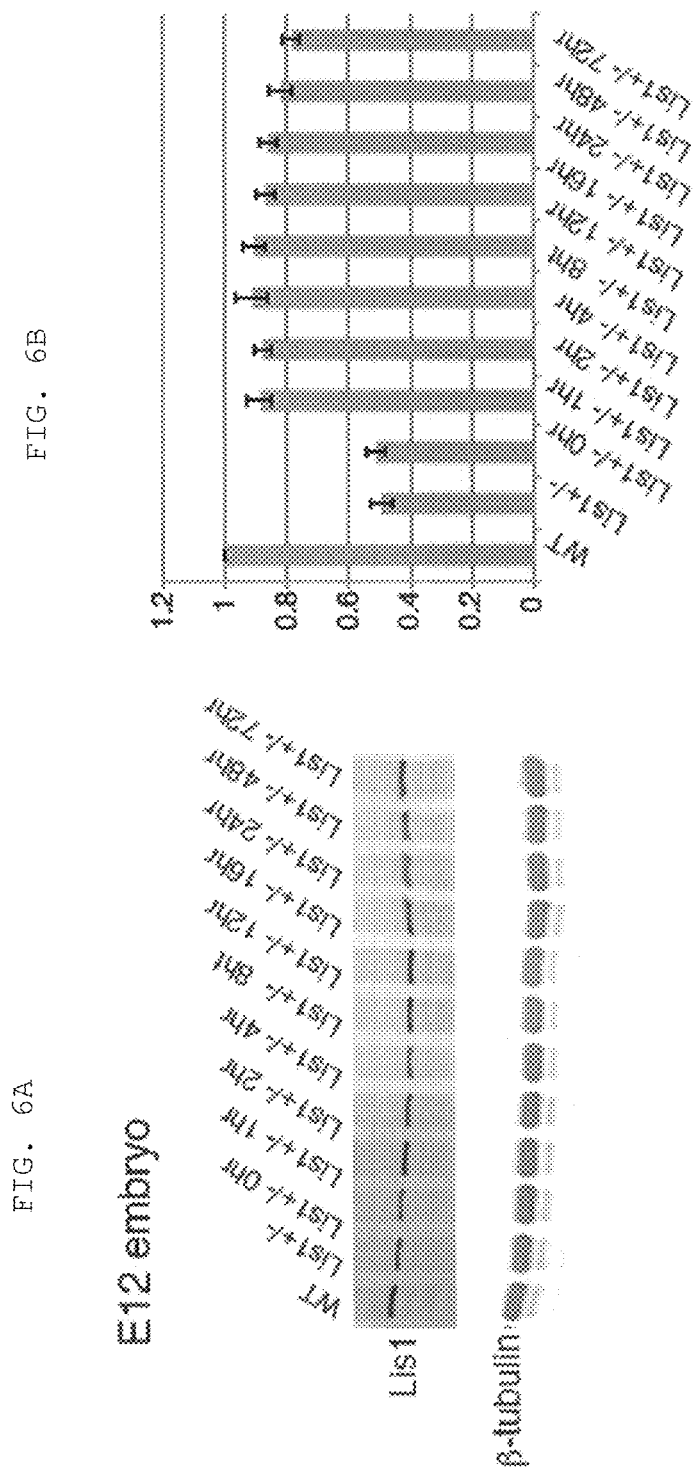

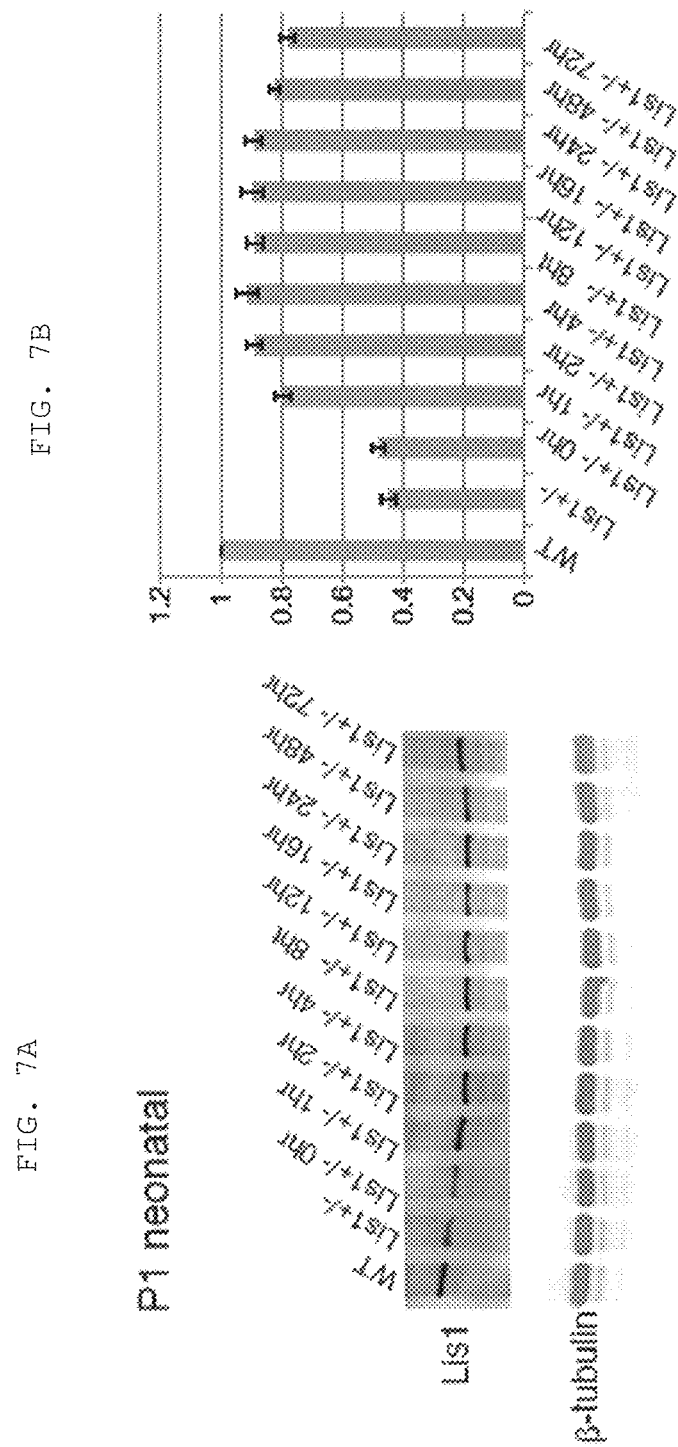

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial
<220> FEATURE:
<223> OTHER INFORMATION: PCR primer

<400> SEQUENCE: 1
```

```
tctaaaatag ttatcctttg ttac                                    24

<210> SEQ ID NO 2
<211> LENGTH: 24
<212> TYPE: DNA
<213> ORGANISM: Artificial
<220> FEATURE:
<223> OTHER INFORMATION: PCR primer

<400> SEQUENCE: 2
aggtgaataa aggaacactg taca                                    24

<210> SEQ ID NO 3
<211> LENGTH: 15
<212> TYPE: DNA
<213> ORGANISM: Homo sapiens

<400> SEQUENCE: 3
gactctgtac aggac                                              15

<210> SEQ ID NO 4
<211> LENGTH: 15
<212> TYPE: DNA
<213> ORGANISM: Homo sapiens

<400> SEQUENCE: 4
gactctgtat aggac                                              15
```

LISSENCEPHALY THERAPEUTIC AGENT

CROSS REFERENCE TO RELATED APPLICATIONS

This application is a continuation-in-part of U.S. patent application Ser. No. 13/988,843, filed May 22, 2013, as the U.S. national stage entry of PCT/JP2011/078000, filed Nov. 28, 2011, and claims priority to Japanese Application No. 2010-264763, filed Nov. 29, 2010, and Japanese Application No. 2011-220480, filed Oct. 4, 2011. The contents of each of these applications are incorporated herein by reference in their entireties.

TECHNICAL FIELD

The present invention relates to a lissencephaly therapeutic agent, and more particularly to a lissencephaly therapeutic agent comprising a compound represented by the following general formula (I)

[Chem. 1]

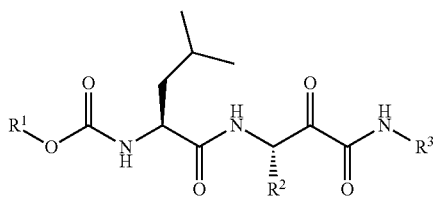

(I)

wherein $R^1$ is lower alkyl substituted with lower alkoxy, lower alkyl substituted with a heterocyclic group, a heterocyclic group, or a group represented by formula (IIa)

[Chem. 2]

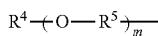

(IIa)

wherein $R^4$ is lower alkyl, $R^5$ is lower alkylene, and m is an integer of 1 to 6;

$R^2$ is lower alkyl optionally substituted with phenyl; and $R^3$ is lower alkyl optionally substituted with halogen, lower alkoxy, or phenyl; condensed polycyclic hydrocarbon; or hydrogen.

BACKGROUND ART

Lissencephaly is a brain malformation characterized by the lack of gyri and the smooth cerebral surface, and in which abnormal layering of the neurons is observed. Lissencephaly patients display severe mental retardation, epileptic strokes, or the like, and their vital prognosis is poor. Lissencephaly patients generally die during their neonatal stage or during early childhood; some, however, live beyond their fifth birthday. The incidence of lissencephaly is about one in 15,000. The clinical diagnosis of lissencephaly is made by diagnostic imaging, such as MRI or CT. A medical specialist interprets images, and identifies gyri abnormalities to make a diagnosis.

About 60% of lissencephaly is presumably attributed to defective neuronal migration caused by heterozygous mutation of Pafah1b1 (LIS1) gene. Specifically, it is assumed that decreased LIS1 protein expression inhibits anterograde transport of cytoplasmic dynein, causing cytoplasmic dynein to localize at the centrosome. This then appears to cause defective neuronal migration, thereby resulting in abnormal layering of the central nervous system (i.e., onset of lissencephaly).

Although lissencephaly is an intractable disease for which an effective treatment has not yet been established, a recent breakthrough report is expected to lead to a treatment therefor (NPL 1). The report shows that, in experiments using cells with LIS1 gene heterozygous mutation (Lis1+/−), treatment of the cells with calpain inhibitor ALLN (Calpain Inhibitor I: the structure thereof is N-Acetyl-Leu-Leu-Nle-CHO (Calbiochem: 208719-25MG)) has increased LIS1 protein expression and restored neuronal migration. Moreover, the report suggests that intraperitoneal administration of ALLN to mice pregnant with Lis1$^{+/-}$ embryonic mice may provide symptomatic improvement in the embryonic mice with lissencephaly.

However, the report only indicates the possibility of ameliorating lissencephaly at the cellular level or embryonic level, and its actual application in clinical practice has remained difficult. This is because the common type of lissencephaly in humans is a sporadic type caused by mutation, and there is little chance that other family members will inherit the disease; thus, in most cases, the diagnosis of lissencephaly is made for the first time after birth, and postnatal treatment is accordingly required.

Additionally, ALLN is a highly toxic compound; thus, has been difficult to use ALLN for the purpose of medical treatment.

Therefore, a therapeutic agent and method capable of even treating newborn babies and infants who have been diagnosed with lissencephaly (i.e., capable of treating lissencephaly patients after birth) has been desired.

The compound represented by general formula (I) above and the method for preparing the compound are described in PTL 1, which also discloses that the compound is usable as a calpain inhibitor.

CITATION LIST

Patent Literature

PTL 1: JP2006-76989A

Non-Patent Literature

NPL 1: Masami Yamada et al., Nature Medicine 15, 1202-1207 (2009)

SUMMARY OF INVENTION

Technical Problem

An object of the present invention is to provide a medicament and method for preventing lissencephaly or treating lissencephaly patients (in particular, lissencephaly patients after birth).

Solution to Problem

The present inventors surprisingly found that administration of the compound represented by the above general formula (I) can treat lissencephaly not only during the fetal period but also after birth, and that the compound has low toxicity. The present invention has been accomplished upon further studies based on these findings.

That is, the present invention includes, for example, lissencephaly therapeutic or preventive agents, etc., according to the following items:

Item A-1. A lissencephaly therapeutic or preventive agent comprising a compound represented by the general formula (I):

[Chem 3]

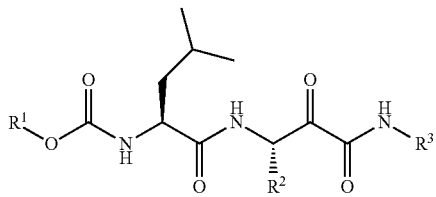

(I)

wherein $R^1$ is lower alkyl substituted with lower alkoxy, lower alkyl substituted with a heterocyclic group, a heterocyclic group, or a group represented by the formula (IIa):

[Chem 4]

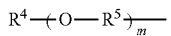

(IIa)

wherein $R^4$ is lower alkyl, $R^5$ is lower alkylene, and m is an integer of 1 to 6;
$R^2$ is lower alkyl optionally substituted with phenyl; and
$R^3$ is lower alkyl optionally substituted with halogen, lower alkoxy, or phenyl; condensed polycyclic hydrocarbon; or hydrogen.

Item A-2. The lissencephaly therapeutic or preventive agent according to item A-1, wherein $R^1$ is a group represented by the formula (IIa):

[Chem 5]

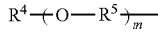

(IIa)

wherein $R^4$ is lower alkyl, $R^5$ is lower alkylene, and m is an integer of 1 to 6.

Item A-3. The lissencephaly therapeutic or preventive agent according to item A-1, wherein $R^1$ is a group represented by the formula (IIb):

[Chem 6]

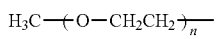

(IIb)

wherein n is an integer of 1 to 6.

Item A-4. The lissencephaly therapeutic or preventive agent according to item A-1, wherein the heterocyclic group that is a substituent for the lower alkyl represented by $R^1$ is pyridyl optionally having lower alkyl.

Item A-5. The lissencephaly therapeutic or preventive agent according to item A-1, wherein the heteroatom of the heterocyclic group represented by $R^1$ is oxygen.

Item A-6. The lissencephaly therapeutic or preventive agent according to any one of items A-1 to A-5, wherein the lower alkyl represented by $R^3$ is cyclopropyl.

Item A-7. The lissencephaly therapeutic or preventive agent according to item A-1, wherein the compound represented by the general formula (I) is ((1S)-1-((((1S)-1-benzyl-2,3-dioxo-3-(cyclopropylamino)propyl)amino)carbonyl)-3-methylbutyl)carbamic acid 2-methoxyethyl ester, ((1S)-1-((((1S)-1-benzyl-2,3-dioxo-3-(cyclopropylamino)propyl)amino)carbonyl)-3-methylbutyl)carbamic acid 5-methoxy-3-oxapentyl ester, ((1S)-1-((((1S)-1-benzyl-2,3-dioxo-3-(cyclopropylamino)propyl)amino)carbonyl)-3-methylbutyl)carbamic acid 8-methoxy-3,6-dioxaoctyl ester, ((1S)-1-((((1S)-1-benzyl-2,3-dioxo-3-(cyclopropylamino)propyl)amino)carbonyl)-3-methylbutyl)carbamic acid 11-methoxy-3,6,9-trioxaundecanyl ester, ((1S)-1-((((1S)-1-benzyl-3-(cyclopropylamino)-2,3-dioxopropyl)amino)carbonyl)-3-methylbutyl)carbamic acid 2-(pyridin-2-yl)ethyl ester, or ((1S)-1-((((1S)-1-benzyl-2,3-dioxo-3-(cyclobutylamino)propyl)amino)carbonyl)-3-methylbutyl)carbamic acid 5-methoxy-3-oxapentyl ester.

Item A-8. The lissencephaly therapeutic or preventive agent according to any one of items A-1 to A-7, which is an oral preparation, injection, or intravenous drip.

Item A-9. The lissencephaly therapeutic or preventive agent according to any one of items A-1 to A-8, wherein the compound represented by the general formula (I) is used such that about 50 to about 1,200 mg of the compound is administered to a lissencephaly patient or a pregnant woman once every two to five days.

Item B-1. A method for treating lissencephaly comprising administering a compound (or a pharmaceutical composition comprising the compound) represented by the general formula (I):

[Chem 7]

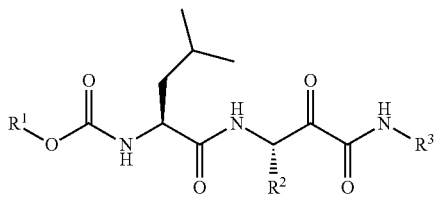

(I)

wherein $R^1$ is lower alkyl substituted with lower alkoxy, lower alkyl substituted with a heterocyclic group, a heterocyclic group, or a group represented by the formula (IIa):

[Chem 8]

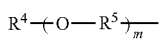

(IIa)

wherein $R^4$ is lower alkyl, $R^5$ is lower alkylene, and m is an integer of 1 to 6;
$R^2$ is lower alkyl optionally substituted with phenyl; and
$R^3$ is lower alkyl optionally substituted with halogen, lower alkoxy, or phenyl; condensed polycyclic hydrocarbon; or hydrogen;
to a lissencephaly patient or a pregnant woman who is carrying a lissencephaly fetus; or a method for preventing lissencephaly comprising administering the compound (or the pharmaceutical composition) to a pregnant woman.

Item B-2. The method for treating or preventing lissencephaly according to item B-1, wherein $R^1$ is a group represented by the formula (IIa):

[Chem 9]

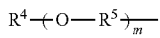
(IIa)

wherein $R^4$ is lower alkyl, $R^5$ is lower alkylene, and m is an integer of 1 to 6.

Item B-3. The method for treating or preventing lissencephaly according to item B-1, wherein $R^1$ is a group represented by the formula (IIb):

[Chem 10]

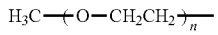
(IIb)

wherein n is an integer of 1 to 6.

Item B-4. The method for treating or preventing lissencephaly according to item B-1, wherein the heterocyclic group that is a substituent for the lower alkyl represented by $R^1$ is pyridyl optionally having lower alkyl.

Item B-5. The method for treating or preventing lissencephaly according to item B-1, wherein the heteroatom of the heterocyclic group represented by $R^1$ is oxygen.

Item B-6. The lissencephaly therapeutic or preventive agent according to any one of items B-1 to B-5, wherein the lower alkyl represented by $R^3$ is cyclopropyl.

Item B-7. The method for treating or preventing lissencephaly according to item B-1, wherein the compound represented by the general formula (I) is ((1S)-1-((((1S)-1-benzyl-2,3-dioxo-3-(cyclopropylamino)propyl)amino)carbonyl)-3-methylbutyl)carbamic acid 2-methoxyethyl ester, ((1S)-1-((((1S)-1-benzyl-2,3-dioxo-3-(cyclopropylamino)propyl)amino)carbonyl)-3-methylbutyl)carbamic acid 5-methoxy-3-oxapentyl ester, ((1S)-1-((((1S)-1-benzyl-2,3-dioxo-3-(cyclopropylamino)propyl)amino)carbonyl)-3-methylbutyl)carbamic acid 8-methoxy-3,6-dioxaoctyl ester, ((1S)-1-((((1S)-1-benzyl-2,3-dioxo-3-(cyclopropylamino)propyl)amino)carbonyl)-3-methylbutyl)carbamic acid 11-methoxy-3,6,9-trioxaundecanyl ester, ((1S)-1-((((1S)-1-benzyl-3-(cyclopropylamino)-2,3-dioxopropyl)amino)carbonyl)-3-methylbutyl)carbamic acid 2-(pyridin-2-yl)ethyl ester, or ((1S)-1-((((1S)-1-benzyl-2,3-dioxo-3-(cyclobutylamino)propyl)amino)carbonyl)-3-methylbutyl)carbamic acid 5-methoxy-3-oxapentyl ester.

Item B-8. The method for treating or preventing lissencephaly according to any one of items B-1 to B-7, wherein the administration is oral administration or intravascular administration (preferably intravenous administration).

Item B-9. The method for treating or preventing lissencephaly according to any one of items B-1 to B-8, wherein the compound represented by the general formula (I) is used such that about 50 to about 1,200 mg of the compound is administered to a lissencephaly patient once every two to five days.

Item C-1. A compound for use in the treatment or prevention of lissencephaly, or a pharmaceutical composition comprising the compound; the compound being represented by the general formula (I):

[Chem 11]

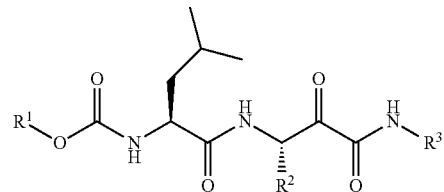
(I)

wherein $R^1$ is lower alkyl substituted with lower alkoxy, lower alkyl substituted with a heterocyclic group, a heterocyclic group, or a group represented by the formula (IIa):

[Chem 12]

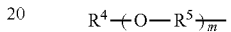
(IIa)

wherein $R^4$ is lower alkyl, $R^5$ is lower alkylene, and m is an integer of 1 to 6;

$R^2$ is lower alkyl optionally substituted with phenyl; and $R^3$ is lower alkyl optionally substituted with halogen, lower alkoxy, or phenyl; condensed polycyclic hydrocarbon; or hydrogen.

Item C-2. The compound or pharmaceutical composition according to item C-1, wherein $R^1$ is a group represented by the formula (IIa):

[Chem 13]

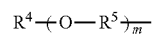
(IIa)

wherein $R^4$ is lower alkyl, $R^5$ is lower alkylene, and m is an integer of 1 to 6.

Item C-3. The compound or pharmaceutical composition according to item C-1, wherein $R^1$ is a group represented by the formula (IIb):

[Chem 14]

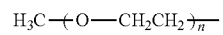
(IIb)

wherein n is an integer of 1 to 6.

Item C-4. The compound or pharmaceutical composition according to item C-1, wherein the heterocyclic group that is a substituent for the lower alkyl represented by $R^1$ is pyridyl optionally having lower alkyl.

Item C-5. The compound or pharmaceutical composition according to item C-1, wherein the heteroatom of the heterocyclic group represented by $R^1$ is oxygen.

Item C-6. The compound or pharmaceutical composition according to any one of items C-1 to C-5, wherein the lower alkyl represented by $R^3$ is cyclopropyl.

Item C-7. The compound or pharmaceutical composition according to item C-1, wherein the compound represented by the general formula (I) is ((1S)-1-((((1S)-1-benzyl-2,3-dioxo-3-(cyclopropylamino)propyl)amino)carbonyl)-3-methylbutyl)carbamic acid 2-methoxyethyl ester, ((1S)-1-((((1S)-1-benzyl-2,3-dioxo-3-(cyclopropylamino)propyl)

amino)carbonyl)-3-methylbutyl)carbamic acid 5-methoxy-3-oxapentyl ester, ((1S)-1-((((1S)-1-benzyl-2,3-dioxo-3-(cyclopropylamino)propyl)amino)carbonyl)-3-methylbutyl)carbamic acid 8-methoxy-3,6-dioxaoctyl ester, ((1S)-1-((((1S)-1-benzyl-2,3-dioxo-3-(cyclopropylamino)propyl)amino)carbonyl)-3-methylbutyl)carbamic acid 11-methoxy-3,6,9-trioxaundecanyl ester, ((1S)-1-((((1S)-1-benzyl-3-(cyclopropylamino)-2,3-dioxopropyl)amino)carbonyl)-3-methylbutyl)carbamic acid 2-(pyridin-2-yl)ethyl ester, or ((1S)-1-((((1S)-1-benzyl-2,3-dioxo-3-(cyclobutylamino)propyl)amino)carbonyl)-3-methylbutyl)carbamic acid 5-methoxy-3-oxapentyl ester.

Item C-8. The compound or pharmaceutical composition according to any one of items C-1 to C-7, which is administered via oral administration or intravascular administration (preferably intravenous administration).

Item C-9. The compound or pharmaceutical composition according to any one of items C-1 to C-8, wherein the compound represented by the general formula (I) is used such that about 50 to about 1,200 mg of the compound is administered to a lissencephaly patient or a pregnant woman once every two to five days.

Item D-1. Use of a compound in the production of a medicament for treating or preventing lissencephaly, the compound being represented by the general formula (I):

[Chem 15]

(I)

wherein $R^1$ is lower alkyl substituted with lower alkoxy, lower alkyl substituted with a heterocyclic group, a heterocyclic group, or a group represented by the formula (IIa):

[Chem 16]

$$R^4\!\!-\!\!(\!O\!-\!R^5\!)_{\overline{m}}$$

(IIa)

wherein $R^4$ is lower alkyl, $R^5$ is lower alkylene, and m is an integer of 1 to 6;
$R^2$ is lower alkyl optionally substituted with phenyl; and
$R^3$ is lower alkyl optionally substituted with halogen, lower alkoxy, or phenyl; condensed polycyclic hydrocarbon; or hydrogen.

Item D-2. The use according to item D-1, wherein $R^1$ is a group represented by the formula (IIa):

[Chem 17]

$$R^4\!\!-\!\!(\!O\!-\!R^5\!)_{\overline{m}}$$

(IIa)

wherein $R^4$ is lower alkyl, $R^5$ is lower alkylene, and m is an integer of 1 to 6.

Item D-3. The use according to item D-1, wherein $R^1$ is a group represented by the formula (IIb):

[Chem 18]

$$H_3C\!\!-\!\!(\!O\!-\!CH_2CH_2\!)_{\overline{n}}$$

(IIb)

wherein n is an integer of 1 to 6.

Item D-4. The use according to item D-1, wherein the heterocyclic group that is a substituent for the lower alkyl represented by $R^1$ is pyridyl optionally having lower alkyl.

Item D-5. The use according to item D-1, wherein the heteroatom of the heterocyclic group represented by $R^1$ is oxygen.

Item D-6. The use according to any one of items D-1 to D-5, wherein the lower alkyl represented by $R^3$ is cyclopropyl.

Item D-7. The use according to item D-1, wherein the compound represented by the general formula (I) is ((1S)-1-((((1S)-1-benzyl-2,3-dioxo-3-(cyclopropylamino)propyl)amino)carbonyl)-3-methylbutyl)carbamic acid 2-methoxyethyl ester, ((1S)-1-((((1S)-1-benzyl-2,3-dioxo-3-(cyclopropylamino)propyl)amino)carbonyl)-3-methylbutyl)carbamic acid 5-methoxy-3-oxapentyl ester, ((1S)-1-((((1S)-1-benzyl-2,3-dioxo-3-(cyclopropylamino)propyl)amino)carbonyl)-3-methylbutyl)carbamic acid 8-methoxy-3,6-dioxaoctyl ester, ((1S)-1-((((1S)-1-benzyl-2,3-dioxo-3-(cyclopropylamino)propyl)amino)carbonyl)-3-methylbutyl)carbamic acid 11-methoxy-3,6,9-trioxaundecanyl ester, ((1S)-1-((((1S)-1-benzyl-3-(cyclopropylamino)-2,3-dioxopropyl)amino)carbonyl)-3-methylbutyl)carbamic acid 2-(pyridin-2-yl)ethyl ester, or ((1S)-1-((((1S)-1-benzyl-2,3-dioxo-3-(cyclobutylamino)propyl)amino)carbonyl)-3-methylbutyl)carbamic acid 5-methoxy-3-oxapentyl ester.

Item D-8. The use according to any one of items D-1 to D-7, wherein the medicament is an oral preparation, injection, or intravenous drip.

Item D-9. The use according to any one of items D-1 to D-8, wherein the medicament is used such that about 50 to about 1,200 mg of the compound represented by the general formula (I) is administered to a lissencephaly patient or a pregnant woman once every two to five days.

((1S)-1-((((1S)-1-benzyl-2,3-dioxo-3-(cyclopropylamino)propyl)amino)carbonyl)-3-methylbutyl)carbamic acid 5-methoxy-3-oxapentyl ester is also called SNJ-1945.

Advantageous Effects of Invention

The use of the lissencephaly therapeutic agent of the present invention allows treatment of lissencephaly, which has been difficult to treat, not only in a fetus in the mother's womb, but also in an infant after birth. More specifically, when the lissencephaly therapeutic agent of the present invention is administered either to a mother or a lissencephaly patient after birth, the decrease in LIS1 protein of the lissencephaly patient can be prevented in both cases. This results in the recovery of nerve cell migration, thereby improving the symptoms of lissencephaly.

If heterozygous mutations are found in the LIS1 gene of a fetus by prenatal genetic diagnosis, etc., which indicates a high possibility that the fetus may develop lissencephaly, the compound represented by the general formula (I) can be administered to the mother to prevent the fetus from developing lissencephaly or to treat the lissencephaly of the fetus. Even when no heterozygous mutations are found in the LIS1 gene of a fetus before birth, and when the presence of factors involved in the development of lissencephaly is not confirmed, the compound represented by the general formula (I) can be administered to the mother to prevent the child from developing lissencephaly.

That is, the compound represented by the general formula (I) can be administered to the mother to prevent lissencephaly in the fetus, regardless of the possibility that the fetus may suffer from lissencephaly.

In addition, the effect of the lissencephaly therapeutic or preventive agent of the present invention can be sustained for at least three days or more by one administration, thus reducing the burden of a subject for administration (a mother or a lissencephaly patient). Accordingly, an improvement in medication compliance can be expected.

BRIEF DESCRIPTION OF DRAWINGS

FIGS. 1A-1B show the results of analysis of the influence of SNJ-1945 on intracellular LIS protein amount. FIG. 1A shows detection of proteins by way of western blotting, and the graph in FIG. 1B shows the intensities of the bands of FIG. 1A. The results reveal that LIS protein amount was recovered by SNJ-1945 administration.

FIGS. 5A-5B show the results of analysis of the influence of SNJ-1945 on migration capability of nerve cells (cerebellar granule nerve cells). FIG. 5A shows results of observation with a fluorescence microscope of cell migration upon incubation of nerve cell aggregates, and FIG. 5B is a graph obtained by summarizing nerve cell migration on migration distance basis. The results reveal that the migration capability of nerve cells was recovered by SNJ-1945 administration.

FIGS. 6A-6B show the results of analysis of the influence of SNJ-1945 on LIS protein amount in a brain of a mouse embryo (100 μg/g:IP, embryonic period=E12, n=6). FIG. 6A shows detection of LIS protein by way of western blotting, and the graph in FIG. 6B shows the intensities of the bands of FIG. 6A.

FIGS. 7A-7B show the results of analysis of the influence of SNJ-1945 on LIS protein amount in the brain of a newborn mouse (200 μg/g:PO, newborn mouse P1, n=6). FIG. 7A shows detection of LIS protein by way of western blotting, and the graph in FIG. 7B shows the intensities of the bands of FIG. 7A.

FIG. 8A shows detection of LIS protein by way of western blotting, and the graph in FIG. 8B shows the intensities of the bands of FIG. 8A.

FIG. 9A shows the results of staining of brain tissue by the TUNNEL method, and the graph in FIG. 9B shows proportions of stained cells based on the total number of stained cells in FIG. 9A.

FIG. 10 shows a graph showing changes in duration of stay for mice in multiple groups during repeated rotor rod tests.

FIG. 11 shows a comparison graph in terms of total duration of stay among mice in multiple groups.

FIG. 23A shows the results of western blotting. FIG. 23B shows the intensities of the bands detected by the western blotting.

DESCRIPTION OF EMBODIMENTS

Figure 2B:
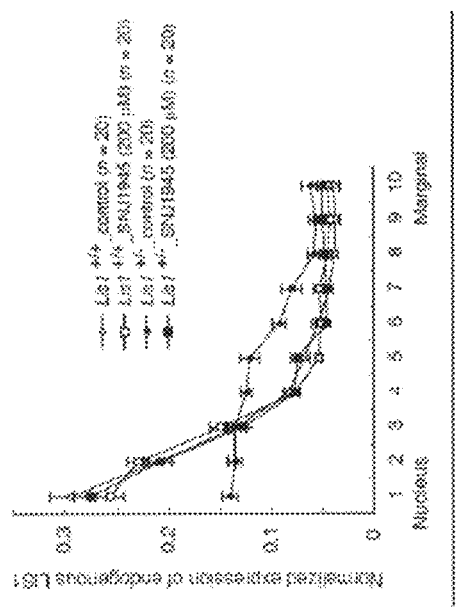
FIGS. 2A-2B show the results of analysis of the influence of SNJ-1945 on intracellular LIS protein localization. The results reveal that LIS protein localization was recovered by SNJ-1945 administration.

The present invention is described in more detail below.

In the general formula (I) described above, $R^1$ may be lower alkyl substituted with lower alkoxy, or lower alkyl substituted with a heterocyclic group. That is, $R^1$ may be lower alkyl, which is substituted with lower alkoxy or a heterocyclic group. The lower alkyl is preferably $C_{1-6}$ (1, 2, 3, 4, 5, or 6) linear or branched alkyl, such as methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1-ethyl-2-methylpropyl, or 1,1,2-trimethyl propyl. More preferred among these is linear or branched alkyl having 2 or 3 carbon atoms, and particularly preferred is ethyl.

The lower alkoxy that is a substituent for the lower alkyl represented by $R^1$ is preferably $C_{1-6}$ (1, 2, 3, 4, 5, or 6) lower alkoxy. That is, the lower alkyl substituted with lower alkoxy represented by $R^1$ is preferably lower alkyl substituted with $C_{1-6}$ lower alkoxy. Examples of the $C_{1-6}$ lower alkoxy include methoxy, ethoxy, propoxy, isopropoxy, butoxy, isobutoxy, sec-butoxy, tert-butoxy, pentyloxy, isopentyloxy, neopentyloxy, tert-pentyloxy, 1-methylbutoxy, 2-methylbutoxy, 1,2-dimethylpropoxy, hexyloxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1-ethyl-2-methylpropoxy, and 1,1,2-trimethylpropoxy. Preferred among these are methoxy and ethoxy.

The alkoxy is optionally substituted with lower alkoxy on the carbon that forms the alkoxy. The lower alkoxy that is a substituent is further optionally substituted with lower alkoxy. Such substitution may be repeated several times. That is, $R^1$ may also be a group represented by the formula (IIa):

[Chem 19]

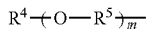

(IIa)

wherein $R^4$ is lower alkyl, $R^5$ is lower alkylene, and m is an integer of 1 to 6.

A more preferable group is represented by the formula (IIb):

[Chem 20]

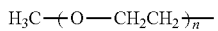

(IIb)

wherein n is an integer of 1 to 6.

The lower alkyl represented by $R^4$ in the formula (IIa) is preferably $C_{1-6}$ (1, 2, 3, 4, 5, or 6) linear or branched alkyl, such as methyl, ethyl, propyl, isopropyl, butyl, isobutyl, sec-butyl, or tert-butyl. Preferred among these are methyl, isopropyl, and tert-butyl, and more preferred is methyl.

The lower alkylene represented by $R^5$ in the formula (IIa) is preferably $C_{1-4}$ (1, 2, 3, or 4) alkylene, such as methylene, ethylene, trimethylene, or tetramethylene; among which ethylene is more preferred. The lower alkylene represented by $R^5$ is optionally substituted with, for example, lower alkyl (in particular, $C_{1-6}$ linear or branched alkyl), such as methyl or ethyl.

m in the formula (IIa) is an integer of 1 to 6 (1, 2, 3, 4, 5, or 6), and preferably an integer of 2 to 5. n in the formula (IIb) is an integer of 1 to 6 (1, 2, 3, 4, 5, or 6), preferably an integer of 1 to 5, and more preferably an integer of 2 to 5.

The heterocyclic group that is a substituent for the lower alkyl represented by $R^1$ is preferably pyridyl optionally having lower alkyl (i.e., optionally substituted with lower alkyl). More specifically, the lower alkyl substituted with a heterocyclic group represented by $R^1$ is preferably lower alkyl substituted with pyridyl optionally having lower alkyl. Examples of the pyridyl include 2-pyridyl, 3-pyridyl, and 4-pyridyl. The lower alkyl that the pyridyl optionally has is preferably $C_{1-3}$ lower alkyl, such as methyl, ethyl, propyl, or isopropyl. When the pyridyl has lower alkyl, the lower alkyl is preferably, but not limited to, located at the 5- or 6-position of the pyridyl (i.e., the hydrogen at the 5- or 6-position of the pyridyl is substituted with the lower alkyl).

$R^1$ may also be a heterocyclic group. Examples of the heterocyclic group represented by $R^1$ include 5- to 7-membered aromatic groups containing one to three atoms independently selected from the group consisting of sulfur, oxygen, and nitrogen; and partially or fully reduced, saturated heterocyclic groups. Specific examples thereof include furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl, pyrazinyl, morpholinyl, thiomorpholinyl, pyrrolidinyl, pyrrolinyl, imidazolidinyl, pyrazolidinyl, piperidinyl, piperazinyl, oxazolidinyl, isoxazolidinyl, thiazolidinyl, pyrazolidinyl, tetrahydrofuranyl, tetrahydropyranyl, tetrahydrothiophenyl, and the like. Preferred among these are saturated heterocyclic groups, more preferred are 5- to 6-membered saturated heterocyclic groups containing oxygen atoms, even more preferred are 1-, 2-, or 3-tetrahydrofuranyl and 1-, 2-, 3-, or 4-tetrahydropyranyl, and most preferred are 3-tetrahydrofuranyl and 4-tetrahydropyranyl.

Examples of the lower alkyl represented by $R^2$ include those mentioned as examples of lower alkyl substituted with lower alkoxy, or lower alkyl substituted with a heterocyclic group represented by $R^1$; among which methyl, ethyl, or isobutyl is preferred. The lower alkyl represented by $R^2$ is preferably substituted with phenyl. Preferable examples of the lower alkyl substituted with phenyl represented by $R^2$ are benzyl and phenylethyl.

The lower alkyl represented by $R^3$ is preferably $C_{1-6}$ (1, 2, 3, 4, 5, or 6) linear or branched alkyl, such as methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1-ethyl-2-methylpropyl, or 1,1,2-trimethylpropyl. Linear or branched alkyl having 2 or 3 carbon atoms is more preferred. The lower alkyl represented by $R^3$ may also be cycloalkyl. Examples of the cycloalkyl include cyclopropyl, cyclobutyl, cyclopentyl, cyclohexyl, and the like; among which cyclopropyl or cyclobutyl is preferred.

This lower alkyl is optionally substituted with halogen, such as fluorine, chlorine, or bromine; among which fluorine is preferred. When the lower alkyl is substituted with halogen, $R^3$ is preferably trifluoromethyl or 2,2,2-trifluoroethyl.

Examples of the lower alkyl substituted with lower alkoxy represented by $R^3$ include those mentioned as examples of the lower alkyl substituted with lower alkoxy represented by $R^1$. Among these, $C_{1-6}$ (1, 2, 3, 4, 5, or 6) lower alkoxy substituted with methoxy or ethoxy is preferred. Examples of the lower alkyl substituted with phenyl represented by $R^3$ include those mentioned as examples of the lower alkyl substituted with phenyl represented by $R^2$.

The condensed polycyclic hydrocarbon represented by $R^3$ is, for example, indanyl, indenyl, naphthyl, anthranil, pentalenyl, or azulenyl; among which indanyl is preferred.

The compounds to be contained in the lissencephaly therapeutic or preventive agent of the present invention may be various solvates, crystalline polymorphs, or prodrugs of the compounds.

The above compounds can be synthesized, for example, by the following method. Some of the compounds are known compounds (see PTL 1 mentioned above).

compound (V)). The addition and removal of the protecting group can be carried out by a known method. Examples of the protecting group include formyl, optionally substituted $C_{1-6}$ alkylcarbonyl (e.g., acetyl and propionyl), optionally substituted phenylcarbonyl, optionally substituted $C_{1-6}$ alkyl-oxycarbonyl (e.g., methoxycarbonyl, ethoxycarbonyl, and tert-butoxycarbonyl), optionally substituted phenyloxycarbonyl, optionally substituted $C_{7-10}$ aralkyloxycarbonyl (e.g., phenyl-$C_{1-4}$ alkyloxycarbonyl, such as benzyloxycarbonyl), and the like. Usable examples of their substituents include halogen (e.g., fluorine, chlorine, bromine, and

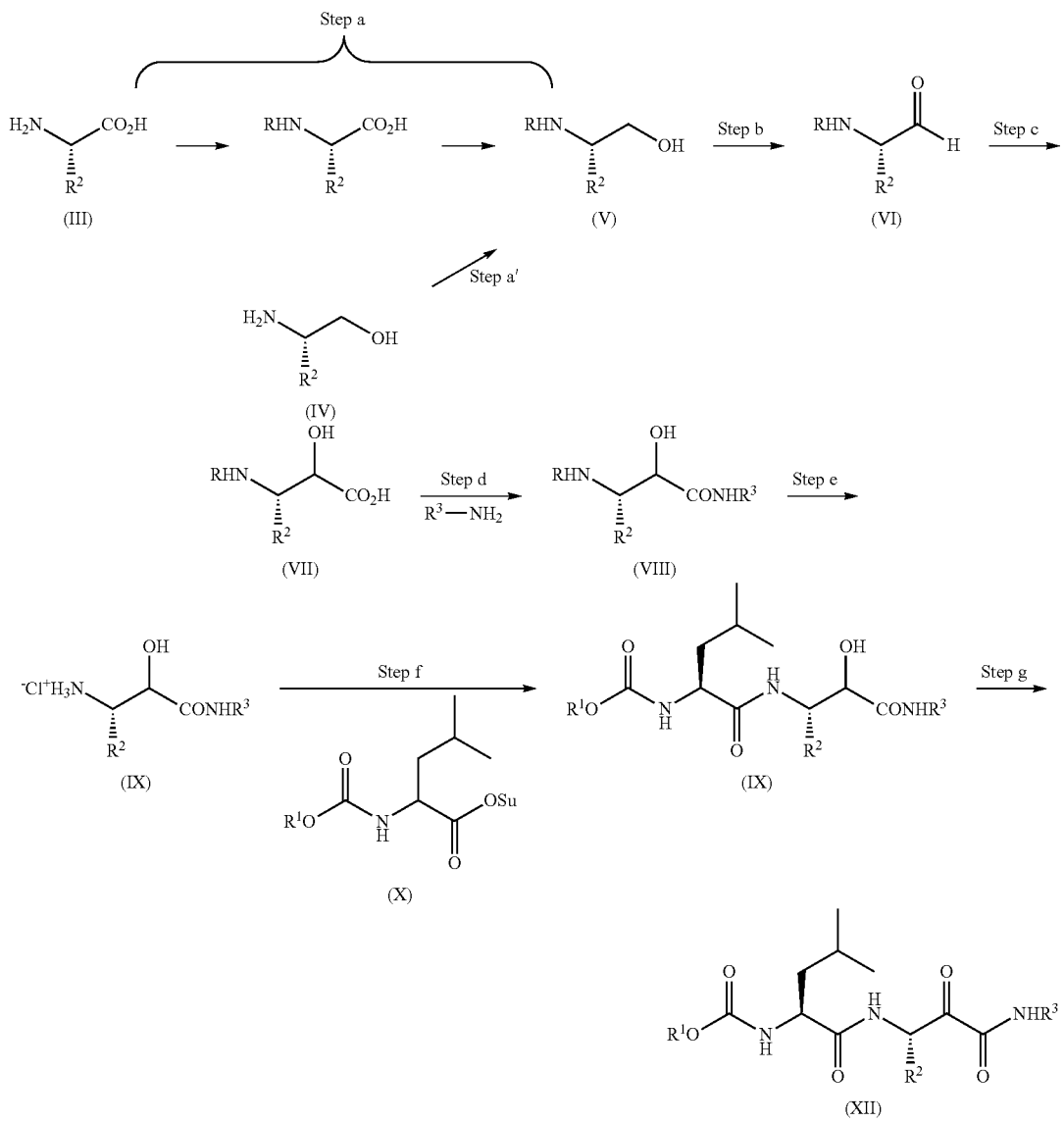

[Chem 21]

wherein R is a protecting group, and the other groups are as defined above.

Step a comprises adding a protecting group to the amino group of an amino acid represented by the formula (III) to convert it to a mixed acid anhydride, and reducing the mixed acid anhydride with a reducing agent to obtain a compound represented by the formula (V) (hereinafter referred to as iodine), nitro, and the like. The number of substituents is about 1 to 3. The most preferable protecting group is tert-butoxycarbonyl (Boc).

Examples of the reducing agent used in the above reaction include lithium aluminum hydride, sodium borohydride, sodium bis(2-methoxyethoxy)aluminum hydride, and the like; among which sodium borohydride is preferred. The reaction temperature is in the range of −40° C. to 30° C., and preferably −20° C. to 0° C.

The compound (V) can also be obtained by similarly adding an aforementioned amino-protecting group to an amino alcohol represented by the formula (IV) (step a').

Step b comprises oxidizing the compound (V) with dimethyl sulfoxide (DMSO) in the presence of an activating agent for DMSO to obtain a compound represented by the formula (VI) (hereinafter referred to as compound (VI)). The DMSO oxidation can be carried out by a known method. For example, the compound (V) is dissolved in DMSO alone or in a mixture of DMSO and a solvent that does not inhibit the oxidation (e.g., tetrahydrofuran, dichloromethane, chloroform, ethyl acetate, benzene, or ether), and diisopropylethylamine is added thereto generally in an amount of about 1 to 10 times by mole per mole of the compound (V). The amount of DMSO used in the above reaction is about 1 to about 20 mL based on 1 g of the compound (V). As the activating agent for DMSO, a sulfur trioxide-pyridine complex, oxalyl chloride, dicyclohexylcarbodiimide, acetic anhydride, or the like can be advantageously used. A sulfur trioxide-pyridine complex is particularly preferred.

Step c comprises treating the compound (VI) with sodium hydrogen sulfite, reacting the resulting product with sodium cyanide to obtain a cyanohydrin compound, hydrolyzing the cyanohydrin compound in the presence of an acid or alkali catalyst without purification to obtain a diastereomer mixture of α-hydroxy-β-amino acid, and re-adding an aforementioned amino-protecting group to the amino group of the α-hydroxy-R-amino acid in a similar manner, thereby producing a compound represented by the formula (VII) (hereinafter referred to as compound (VII)) as a diastereomer mixture.

The hydrolysis reaction is carried out by heating or by heating under reflux using an acid (e.g., hydrochloric acid, sulfuric acid, acetic acid, or formic acid) or an alkali (e.g., sodium hydroxide, potassium hydroxide, or barium hydroxide). The heating temperature is about 50 to about 100° C. As the solvent, a mixture of water and an organic solvent (e.g., dioxane or tetrahydrofuran) is preferably used.

Step d comprises condensing the compound (VII) with various amines to obtain a compound represented by the formula (VIII) (hereinafter referred to as compound (VIII)).

A preferable amine can be suitably selected depending on the target compound. Examples of amines include ethylamine, propylamine, cyclopropylamine, butylamine, cyclobutylamine, methoxyethylamine, 2-phenoxyethylamine, 2-aminoindane, 2,2,2-trifluoroethylamine, and the like.

The condensation reaction is preferably carried out in the presence of a dehydration condensing agent, such as 1-ethyl-3-(3-dimethylaminopropyl)carbodiimide hydrochloride or N,N-dicyclohexylcarbodiimide. Examples of the organic solvent used in the condensation reaction include N,N-dimethylformamide, DMSO, tetrahydrofuran, dichloromethane, methanol, ethanol, benzene, toluene, ethyl acetate, and mixtures thereof; among which N,N-dimethylformamide is preferred. The reaction temperature is within the range of ice-cooling to room temperature.

Step e comprises deprotecting the amino-protecting group of the compound (VIII) under acidic conditions with hydrochloric acid to obtain an amine hydrochloride represented by the formula (IX) (hereinafter referred to as compound (IX)). The deprotection of the amino-protecting group can be carried out by a known method. For example, the compound (VIII) is dissolved in a commonly used organic solvent, and the mixture is stirred in the presence of an acid to remove the amino-protecting group. Examples of the acid include hydrochloric acid, trifluoroacetic acid, p-toluenesulfonic acid, and the like. Alternatively, a commercially available hydrochloric acid-ethyl acetate solution or hydrochloric acid-dioxane solution can be used to remove the amino-protecting group. The reaction temperature is within the range of ice-cooling to room temperature.

Step f comprises condensing the compound (IX) with a compound represented by the formula (X) (hereinafter referred to as compound (X)) in the presence of triethylamine to obtain a compound represented by the formula (XI) (hereinafter referred to as compound (XI)).

The compound (X) can be produced, for example, according to the following general reaction route.

[Chem 22]

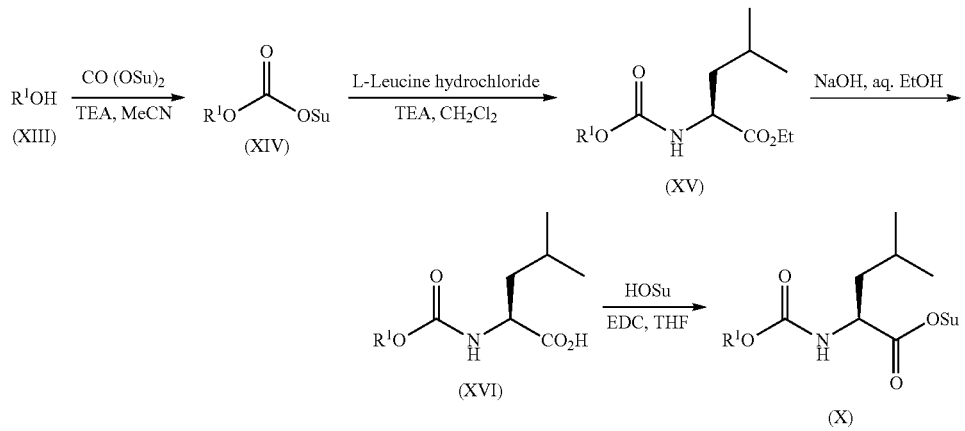

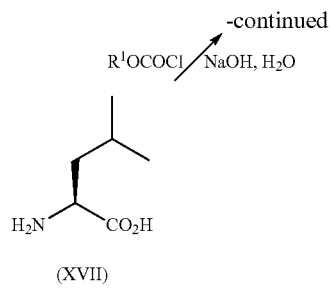

wherein each group is as defined above.

An alcohol represented by the formula (XIII) (hereinafter referred to as compound (XIII)) is reacted with di(N-succinimidyl) carbonate to obtain a mixed carbonate ester represented by the formula (XIV). The mixed carbonate ester is then condensed with L-leucine ethyl ester hydrochloride in the presence of triethylamine to obtain a compound represented by the formula (XV). Alkali saponification of the compound (XV) yields a compound represented by the formula (XVI) (hereinafter referred to as compound (XVI)). Alternatively, the compound (XVI) can be obtained by direct reaction between L-leucine and chloroformate. The compound (XVI) is reacted with hydroxysuccinimide (HOSu) to obtain a succinimide ester represented by the formula (X) (hereinafter referred to as compound (X)).

Step g comprises oxidizing the compound (XI) to obtain a compound represented by the formula (XII) (hereinafter referred to as compound (XII)). The oxidation reaction is carried out by a known method, such as oxidation classified as chromic acid oxidation, including pyridinium dichromate (PDC) oxidation, pyridinium chlorochromate (PCC) oxidation, Jones oxidation, and Collins oxidation; oxidation classified as DMSO oxidation, including Swern oxidation, DMSO/sulfur trioxide-pyridine complex oxidation, DMSO/dicyclohexylcarbodiimide oxidation, and DMSO/oxalyl chloride oxidation; Dess-Martin oxidation using a Dess-Martin reagent (Dess-Martin periodinane); hypohalous acid oxidation; or N-halogenocarboxylic acid amide oxidation; among which Dess-Martin oxidation is particularly preferred. When Dess-Martin oxidation is employed, the compound (XI) is dissolved in a commonly used organic solvent, and a Dess-Martin reagent is added thereto. Examples of the commonly used organic solvent include commonly used solvents that do not adversely affect the reaction, and mixtures of such solvents, such as dichloromethane, N,N-dimethylformamide, DMSO, tetrahydrofuran, methanol, ethanol, benzene, toluene, and ethyl acetate; among which dichloromethane is preferred. The amount of Dess-Martin reagent used is about 1 to 20-fold molar equivalents, preferably 1- to 3-fold molar equivalents, of the compound (XI). The reaction temperature is not particularly limited, and is within the range of ice-cooling to room temperature. The thus-obtained compound (XII) can be separated and purified by a known method, such as concentration, concentration under reduced pressure, solvent extraction, crystallization, recrystallization, solvent transfer, or chromatography. The compound (XII) is represented by the general formula (I).

Each of the above steps is carried out in the presence of a commonly used solvent that does not adversely affect the reaction, or a mixture of such solvents. Examples of the solvent that does not adversely affect the reaction include dichloromethane, N,N-dimethylformamide, DMSO, tetrahydrofuran, methanol, ethanol, benzene, toluene, ethyl acetate, and the like.

Among the compounds represented by the general formula (I) produced by the above-described method, for example, the following compounds are preferably contained in the lissencephaly therapeutic or preventive agent of the present invention: ((1S)-1-((((1S)-1-benzyl-2,3-dioxo-3-(ethylamino)propyl)amino)carbonyl)-3-methylbutyl)carbamic acid 2-methoxyethyl ester (compound 1; the structural formula is shown below),

[Chem 23]

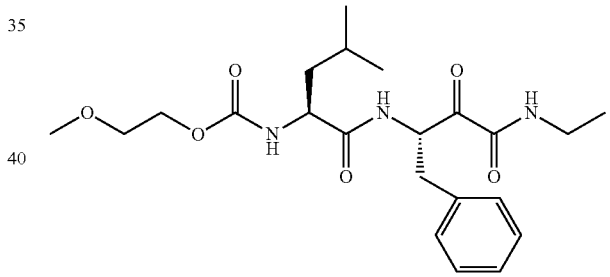

((1S)-1-((((1S)-1-benzyl-2,3-dioxo-3-(ethylamino)propyl)amino)carbonyl)-3-methylbutyl)carbamic acid (3S)-tetrahydrofuran-3-yl ester (compound 2; the structural formula is shown below),

[Chem 24]

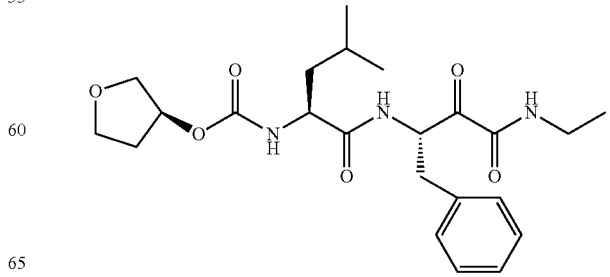

((1S)-1-((((1S)-1-benzyl-2,3-dioxo-3-(ethylamino)propyl)amino)carbonyl)-3-methylbutyl) carbamic acid tetrahydro-4H-pyran-4-yl ester (compound 3; the structural formula is shown below),

[Chem 25]

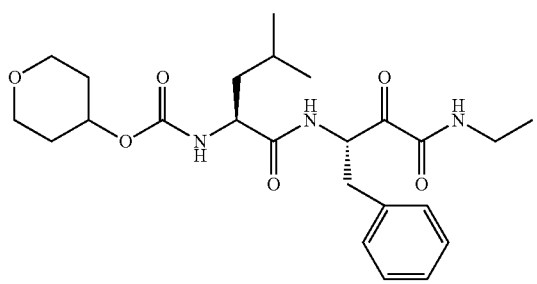

((1S)-1-((((1S)-1-benzyl-2,3-dioxo-3-(cyclopropylamino)propyl)amino)carbonyl)-3-methylbutyl)carbamic acid 2-methoxyethyl ester (compound 4; the structural formula is shown below),

[Chem 26]

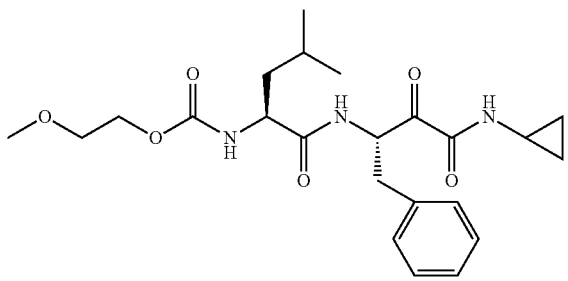

((1S)-1-((((1S)-1-benzyl-3-(cyclopropylamino)-2,3-dioxopropyl)amino)carbonyl)-3-methylbutyl)carbamic acid (3S)-tetrahydrofuran-3-yl ester (compound 5; the structural formula is shown below),

[Chem 27]

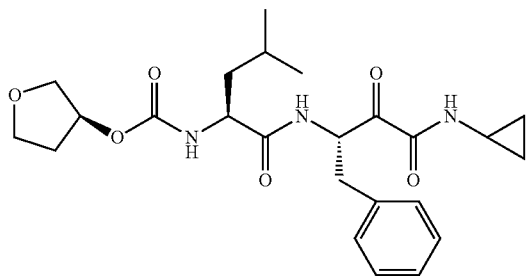

((1S)-1-((((1S)-1-benzyl-3-cyclopropylamino-2,3-dioxopropyl)amino)carbonyl)-3-methylbutyl)carbamic acid tetrahydro-4H-pyran-4-yl ester (compound 6; the structural formula is shown below),

[Chem 28]

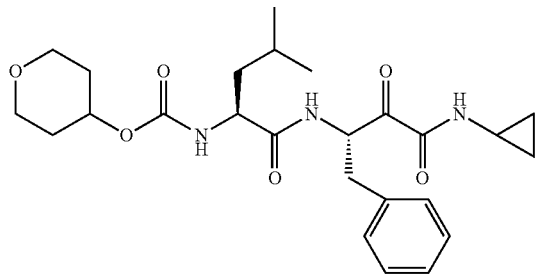

((1S)-1-((((1S)-1-benzyl-2,3-dioxo-3-(propylamino)propyl)amino)carbonyl)-3-methylbutyl)carbamic acid 2-methoxyethyl ester (compound 7; the structural formula is shown below),

[Chem 29]

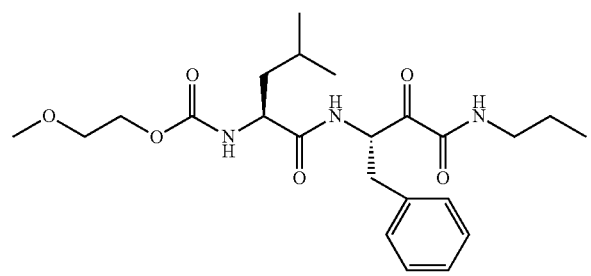

((1S)-1-((((1S)-1-benzyl-2,3-dioxo-3-(cyclobutylamino)propyl)amino)carbonyl)-3-methylbutyl)carbamic acid 2-methoxyethyl ester (compound 8; the structural formula is shown below),

[Chem 30]

((1S)-1-((((1S)-1-benzyl-3-butylamino-2,3-dioxopropyl)amino)carbonyl)-3-methylbutyl)carbamic acid 2-methoxyethyl ester (compound 9; the structural formula is shown below),

[Chem 31]

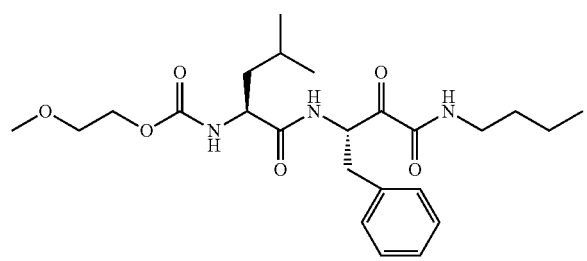

((1S)-1-((((1S)-1-benzyl-2,3-dioxo-3-(2,2,2-trifluoroethyl-amino)propyl)amino)carbonyl)-3-methylbutyl)carbamic acid 2-methoxyethyl ester (compound 10; the structural formula is shown below),

[Chem 32]

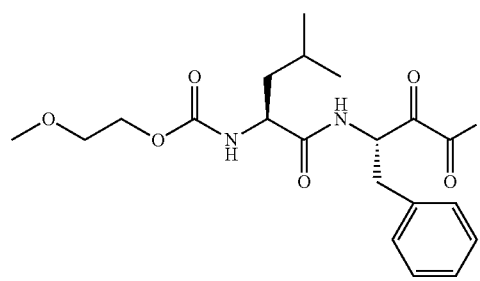

((1S)-1-((((1S)-1-benzyl-2,3-dioxo-3-(2-indanylamino)propyl)amino)carbonyl)-3-methylbutyl)carbamic acid 2-methoxyethyl ester (compound 11; the structural formula is shown below),

[Chem 33]

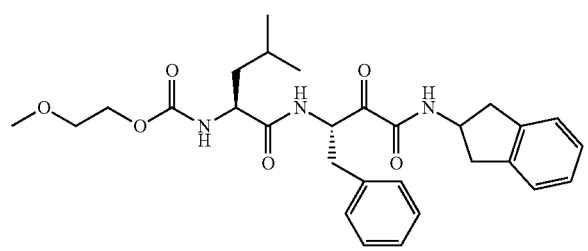

((1S)-1-((((1S)-1-benzyl-2,3-dioxo-3-(2-methoxyethyl-amino)propyl)amino)carbonyl)-3-methylbutyl)carbamic acid 2-methoxyethyl ester (compound 12; the structural formula is shown below),

[Chem 34]

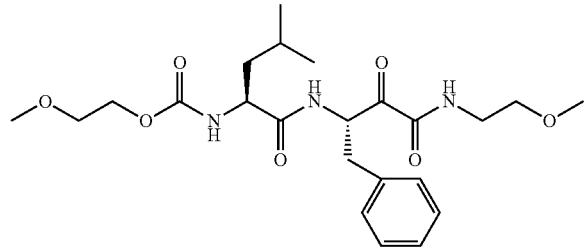

((1S)-1-((((1S)-2, 3-dioxo-3-ethylamino-1-(phenylethyl)propyl)amino)carbonyl)-3-methylbutyl) carbamic acid 2-methoxyethyl ester (compound 13; the structural formula is shown below),

[Chem 35]

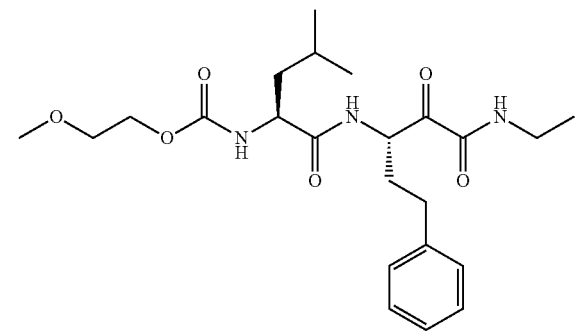

((1S)-1-((((1S)-2,3-dioxo-3-ethylamino-1-(phenylethyl)propyl)amino)carbonyl)-3-methylbutyl) carbamic acid (3S)-tetrahydrofuran-3-yl ester (compound 14; the structural formula is shown below),

[Chem 36]

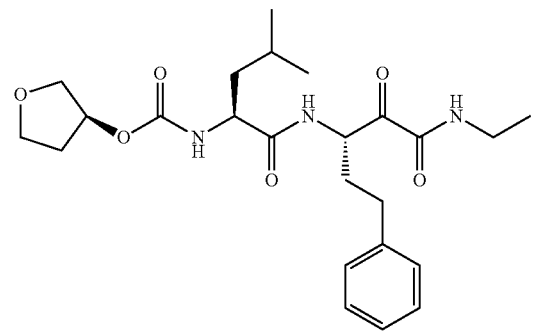

((1S)-1-((((1S)-2,3-dioxo-3-cyclopropylamino-1-(phenylethyl)propyl)amino)carbonyl)-3-methylbutyl) carbamic acid 2-methoxyethyl ester (compound 15; the structural formula is shown below),

[Chem 37]

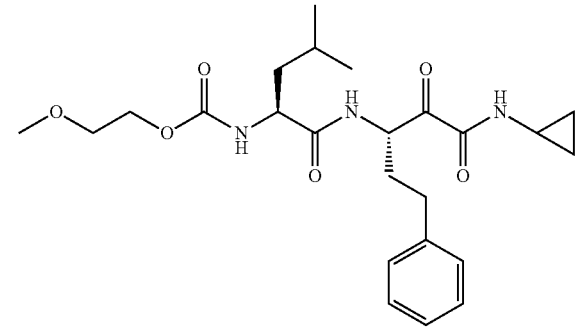

((1S)-1-((((1S)-2,3-dioxo-3-cyclopropylamino-1-(phenylethyl)propyl)amino)carbonyl)-3-methylbutyl) carbamic acid (3S)-tetrahydrofuran-3-yl ester (compound 16; the structural formula is shown below),

[Chem 38]

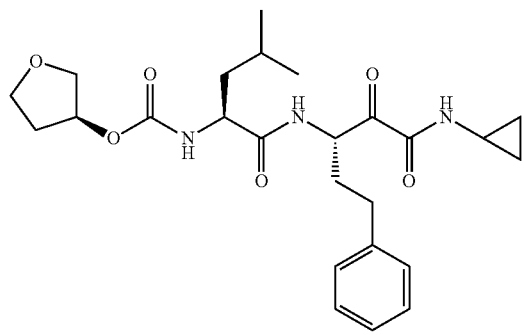

((1S)-1-((((1S)-1-benzyl-2,3-dioxo-3-(cyclopropylamino)propyl)amino)carbonyl)-3-methylbutyl) carbamic acid 5-methoxy-3-oxapentyl ester (compound 17; the structural formula is shown below),

[Chem 39]

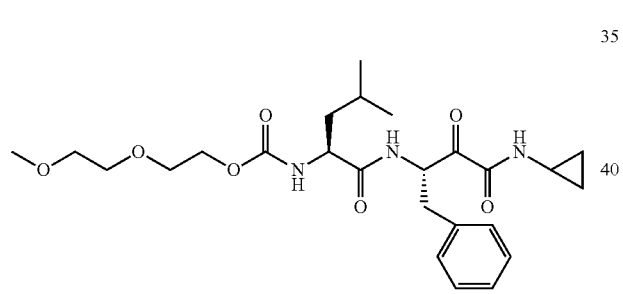

((1S)-1-((((1S)-1-benzyl-2,3-dioxo-3-(cyclopropylamino)propyl)amino)carbonyl)-3-methylbutyl)carbamic acid 8-methoxy-3,6-dioxaoctyl ester (compound 18; the structural formula is shown below),

[Chem 40]

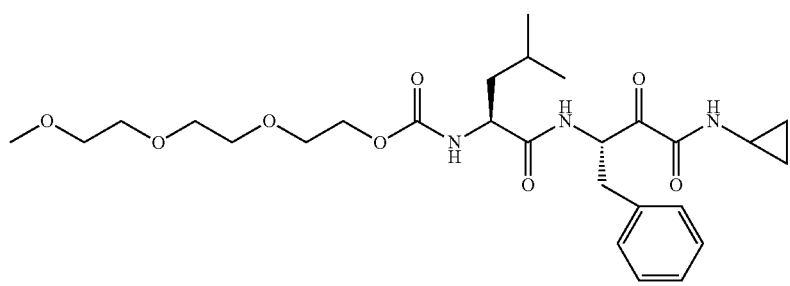

((1S)-1-((((1S)-1-benzyl-2,3-dioxo-3-(cyclopropylamino)propyl)amino)carbonyl)-3-methylbutyl)carbamic acid 11-methoxy-3,6,9-trioxaundecanyl ester (compound 19; the structural formula is shown below),

[Chem 41]

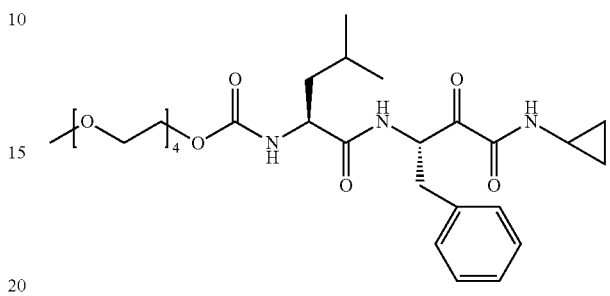

((1S)-1-((((1S)-1-benzyl-2, 3-dioxo-3-(cyclopropylamino)propyl)amino)carbonyl)-3-methylbutyl)carbamic acid 14-methoxy-3,6,9,12-tetraoxatetradecanyl ester (compound 20; the structural formula is shown below),

[Chem 42]

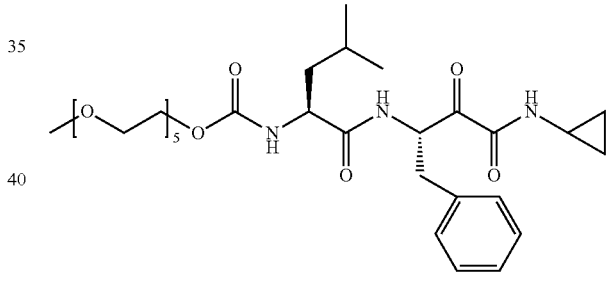

((1S)-1-((((1S)-2, 3-dioxo-1-(2-methylpropyl)-3-(2-phenoxyethyl)aminopropyl)amino)carbonyl)-3-methylbutyl) carbamic acid 2-methoxyethyl ester (compound 21; the structural formula is shown below),

[Chem 43]

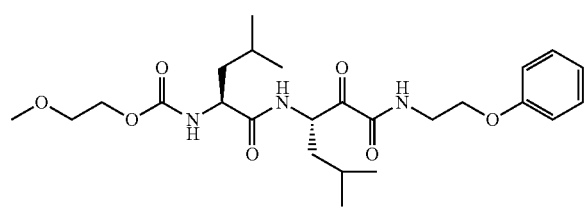

(((1S)-1-(((((1S)-2,3-dioxo-1-(2-methylpropyl)-3-(2-phenoxyethyl)aminopropyl)amino)carbonyl)-3-methylbutyl) carbamic acid 5-methoxy-3-oxapentyl ester (compound 22; the structural formula is shown below),

[Chem 44]

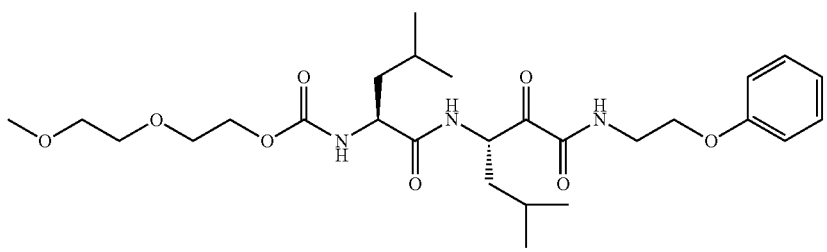

(((1S)-1-(((((1RS)-3-amino-1-benzyl-2,3-dioxopropyl) amino)carbonyl)-3-methylbutyl)carbamic acid 5-methoxy-3-oxapentyl ester (compound 23; the structural formula is shown below),

[Chem 45]

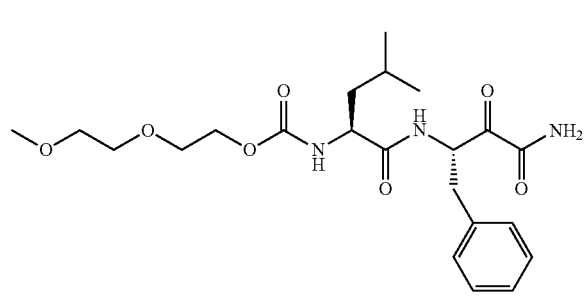

(((1S)-1-(((((1S)-1-benzyl-3-(cyclopropylamino)-2,3-dioxopropyl)amino)carbonyl)-3-methylbutyl)carbamic acid 2-(pyridin-2-yl)ethyl ester (compound 24; the structural formula is shown below),

[Chem 46]

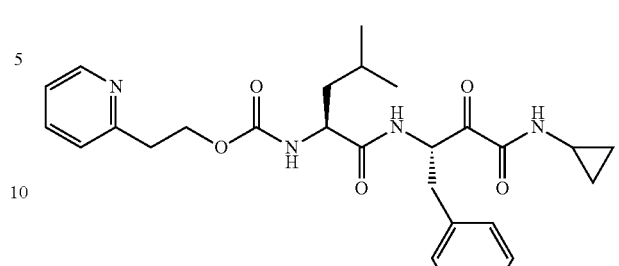

(((1S)-1-(((((1S)-1-benzyl-3-(cyclopropylamino)-2,3-dioxopropyl)amino)carbonyl)-3-methylbutyl)carbamic acid 2-(6-methylpyridin-2-yl)ethyl ester (compound 25; the structural formula is shown below),

[Chem 47]

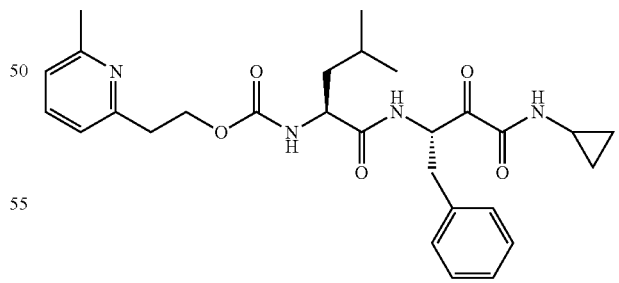

(((1S)-1-(((((1S)-1-benzyl-3-(cyclopropylamino)-2,3-dioxopropyl)amino)carbonyl)-3-methylbutyl)carbamic acid 2-(5-ethylpyridin-2-yl)ethyl ester (compound 26; the structural formula is shown below),

[Chem 48]

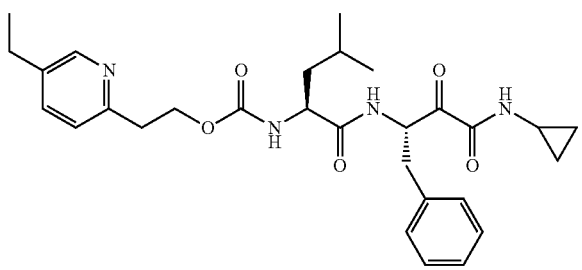

((1S)-1-((((1S)-1-benzyl-3-(cyclopropylamino)-2,3-dioxopropyl)amino)carbonyl)-3-methylbutyl)carbamic acid 2-tert-butoxyethyl ester (compound 27; the structural formula is shown below),

[Chem 49]

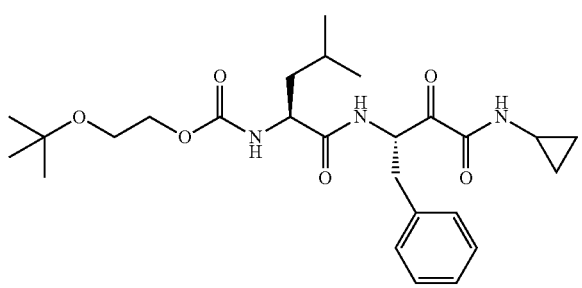

and
((1S)-1-((((1S)-1-benzyl-3-(cyclopropylamino)-2,3-dioxopropyl)amino)carbonyl)-3-methylbutyl)carbamic acid 2-isopropoxyethyl ester (compound 28; the structural formula is shown below).

[Chem 50]

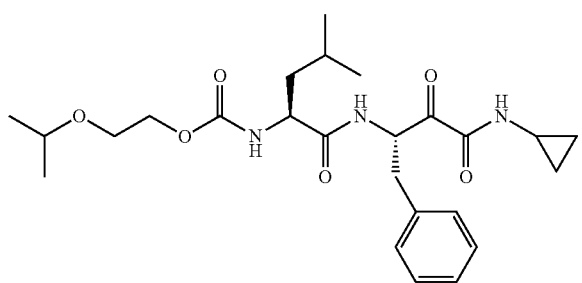

More preferred among these are the compounds 4, 17, 18, 19, and 24; and still more preferred is the compound 17.

PTL 1 (JP2006-76989A) mentioned above discloses the specific production methods and physical properties of the compounds 1 to 28.

These compounds have excellent calpain inhibitory activity, as shown in PTL 1, and can be preferably used as active ingredients of the lissencephaly therapeutic or preventive agent of the present invention.

The use of the lissencephaly therapeutic or preventive agent of the present invention allows treatment of lissencephaly, which has been difficult to treat, not only in a fetus in the mother's womb, but also in an infant after birth. More specifically, when the lissencephaly therapeutic agent of the present invention is administered either to a mother or a lissencephaly patient after birth, the decrease in LIS1 protein of the lissencephaly patient can be prevented in both cases. This results in the recovery of nerve cell migration, thereby improving the symptoms of lissencephaly.

If heterozygous mutations are found in the LIS1 gene of a fetus by prenatal genetic diagnosis, etc., which indicates a high possibility that the fetus may develop lissencephaly, the compound represented by the general formula (I) can be administered to the mother to prevent the fetus from developing lissencephaly or to treat the lissencephaly of the fetus. (If the diagnosis indicates that the fetus has developed lissencephaly, the compound represented by the general formula (I) is used for "treatment"; otherwise, the compound is used for "prevention." However, it is difficult to diagnose whether a fetus has developed lissencephaly; the administration of the compound represented by the general formula (I) to the mother is generally regarded as "prevention.") Even when no heterozygous mutations are found in the LIS1 gene of a fetus before birth, and when the presence of factors involved in the development of lissencephaly is not confirmed, the compound represented by the general formula (I) can be administered to the mother to prevent the child from developing lissencephaly. That is, the compound represented by the general formula (I) can be administered to the mother to prevent lissencephaly in the fetus, regardless of the possibility that the fetus may suffer from lissencephaly.

The lissencephaly therapeutic or preventive agent of the present invention can be used not only for humans, but also for non-human mammals (e.g., rats, mice, rabbits, cattle, pigs, dogs, and cats).

In addition, the above compounds are advantageous for treating or preventing lissencephaly, because they are excellent in tissue transfer and absorbability, are able to pass through the blood brain barrier, are significantly less toxic, and are highly safe. These advantages make the lissencephaly therapeutic or preventive agent of the present invention, which comprises such a compound, favorable. The lissencephaly therapeutic or preventive agent of the present invention can be administered systemically or locally. Systemic administration includes oral administration, and parenteral administration, such as intravenous injection, subcutaneous injection, and intramuscular injection. Local administration includes transdermal administration, mucosal administration, intranasal administration, ocular administration, etc.

The lissencephaly therapeutic or preventive agent of the present invention may comprise only the above compound, or may be in the form of a pharmaceutical composition comprising the compound and a pharmaceutically acceptable carrier or additive, etc. That is, the present invention also includes a pharmaceutical composition comprising the above compound and a pharmaceutically acceptable carrier or additive, etc. The pharmaceutical composition may contain other pharmacologically active substances and pharmaceutically acceptable optional components, to the extent that the effect of the present invention is not impaired. A person skilled in the art can suitably select such carriers, additives, optional components, other pharmacologically active substances, etc., depending on the purpose, and can also suitably determine their amounts and other conditions.

When the lissencephaly therapeutic or preventive agent of the present invention is in the form of a pharmaceutical composition, its dosage form includes, but is not limited thereto, solid preparations (e.g., powders, granules, tablets, capsules, and suppositories), liquid preparations (e.g., syrups, injections, intravenous drips, eye drops, and nasal drops), and the like.

Among these, preparations that can be orally administered (oral preparations), injections, and drops are preferred. These can be produced by a known method.

For example, in the production of granules or tablets, any dosage form can be prepared with the use of pharmaceutically acceptable additives, such as excipients (e.g., lactose, sucrose, glucose, starch, crystalline cellulose, hydroxypropyl methyl cellulose, hydroxyethyl cellulose, hydroxypropyl cellulose, carboxymethyl cellulose, and methyl cellulose), lubricants (e.g., magnesium stearate, talc, stearic acid, and calcium stearate), disintegrators (e.g., starch, carmellose sodium, and calcium carbonate), or binders (e.g., starch paste, hydroxypropylcellulose solution, carmellose solution, gum arabic solution, gelatin solution, and sodium alginate solution). Further, the granules and tablets may be coated with a suitable coating agent (e.g., gelatin, sucrose, gum arabic, or carnauba wax) or a suitable enteric coating agent (e.g., cellulose acetate phthalate, methacrylic copolymer, hydroxypropylcellulose phthalate, or carboxymethylethylcellulose).

In the production of capsules, a known excipient, such as magnesium stearate, calcium stearate, talc, or light silicic acid anhydride, all of which can improve flowability and lubricity; crystalline cellulose and lactose, both of which can increase flowability under pressure; an aforementioned disintegrator; or the like is suitably selected; then mixed or granulated homogenously with the compound of the present invention; and filled in capsules. Alternatively, the granulated products may be coated with a suitable coating agent, and then filled in capsules, or may be encapsulated with a suitable capsule base (e.g., gelatin) having increased plasticity endowed with addition of glycerin, sorbitol, or the like. The capsules may contain, if necessary, coloring agents, preservatives (e.g., sulfur dioxide, and parabens such as methyl parahydroxybenzoate, ethyl parahydroxybenzoate, and propyl parahydroxybenzoate), and the like. The capsules may be in the form of enteric-coated capsules, gastro-resistant capsules, or release-controlled capsules, as well as general capsules. Enteric-coated capsules can be prepared by encapsulating the compound of the present invention coated with an enteric coating agent, or a mixture of the compound of the present invention and an aforementioned suitable excipient, into regular capsules. Alternatively, they can be prepared by encapsulating the compound of the present invention or a mixture of the compound of the present invention and an aforementioned suitable excipient into capsules coated with an enteric coating agent or capsules made from an enteric polymer as a base material.

In the production of suppositories, suppository bases (e.g., cacao butter and macrogol) can be suitably selected and used.

In the production of syrups, stabilizers (e.g., sodium edetate), suspending agents (e.g., gum arabic and carmellose), corrigents (e.g., simple syrup and glucose), perfumes, and the like can be suitably used. A person skilled in the art can suitably select such optional components depending on the purpose, and can also suitably determine their amounts and other conditions.

Injections, intravenous drips, eye drops, or nasal drops of the present invention can be produced by dissolving or dispersing the above compound in a solution suitably containing pharmaceutically acceptable additives, such as isotonic agents (e.g., sodium chloride, potassium chloride, glycerin, mannitol, sorbitol, boric acid, borax, glucose, and propylene glycol), buffers (e.g., phosphate buffer, acetate buffer, borate buffer, carbonate buffer, citrate buffer, Tris buffer, glutamate buffer, and epsilon-aminocaproic acid buffer), preservatives (e.g., methyl parahydroxybenzoate, ethyl parahydroxybenzoate, propyl parahydroxybenzoate, chlorobutanol, benzyl alcohol, benzalkonium chloride, sodium dehydroacetate, sodium edetate, boric acid, and borax), thickeners (e.g., hydroxyethylcellulose, hydroxypropylcellulose, polyvinyl alcohol, and polyethylene glycol), stabilizers (e.g., sodium hydrogen sulfite, sodium thiosulfate, sodium edetate, sodium citrate, ascorbic acid, and dibutylhydroxytoluene), and pH adjusters (e.g., hydrochloric acid, sodium hydroxide, phosphoric acid, and acetic acid). A person skilled in the art can suitably select such pharmaceutically acceptable additives depending on the purpose, and can also suitably determine their amounts and other conditions.

Although the amount of additives in the above-mentioned injections, eye drops, or nasal drops depends on the type and application of additives to be added, the additive content may be determined so that the purpose of the additives can be achieved.

The dosage of the lissencephaly therapeutic or preventive agent of the present invention depends on the degree of lissencephaly progression in the patient to be administered, age, administration route, and other conditions; for example, the amount of the above compound, which is an active ingredient of the therapeutic agent of the present invention, is about 0.1 to about 2,000 mg, and preferably about 1 to about 1,500 mg, per day. In particular, in the case of oral administration or intravascular administration (preferably intravenous administration), the dosage per day is, for example, about 10 to about 1,500 mg, preferably about 20 to about 1,500 mg, more preferably about 50 to about 1,200 mg, and even more preferably about 100 to about 1,000 mg. The lissencephaly therapeutic or preventive agent of the present invention may be administered in several divided doses (preferably 1, 2, or 3 doses) per day, for example. When the lissencephaly therapeutic agent of the present invention is administered to a patient after birth (i.e., when it is used as a lissencephaly therapeutic agent after birth), the timing of administration may be anywhere between immediately after birth to death; however, in terms of therapeutic effects, it is preferable to initiate the administration as early as possible (if possible, immediately after diagnosis of lissencephaly). Similarly, when the agent of the present invention is administered to the mother to treat the fetus (or prevent the fetus from developing the disease), it is also preferable to initiate the administration as early as possible after the fetus is diagnosed as lissencephaly (or highly probable lissencephaly). When the agent of the present invention is administered for the purpose of prevention without examining whether the fetus has developed lissencephaly, the administration may be initiated after pregnancy is confirmed. The dosage to the mother may be, for example, the same as the above-mentioned dosage, and a person skilled in the art can suitably select the dosage within the above-mentioned range, depending on the conditions of the patient or mother.

The lissencephaly therapeutic or preventive agent of the present invention characteristically shows a relatively long-term effect once administered. For example, the effect is expected to be obtained by administering the agent comprising about 50 to about 1,200 mg, and preferably about 100 to about 1,000 mg, of the above compound once every two to five days (preferably three days).

The amount of the above compound, which is an active ingredient of the lissencephaly therapeutic or preventive agent of the present invention, is not particularly limited. For example, the amount of the compound may be 0.01 to 100 wt. %, and preferably 0.1 to 99 wt. %, based on the entire therapeutic or preventive agent.

The present invention also provides a method for treating or preventing lissencephaly, comprising administering the lissencephaly therapeutic agent of the present invention to a lissencephaly patient or a mother, as described above. This method is specifically performed by administering the lissencephaly therapeutic or preventive agent of the present invention. The conditions for the method, including the target for administration, the route and time of administration, and the dosage of the above compound, which is an active ingredient, are as described above.

In addition, the above compound contained in the lissencephaly therapeutic or preventive agent of the present invention is also advantageous in that its toxicity is particularly lower than other calpain inhibitors, and that side effects are relatively lower. Moreover, since other calpain inhibitors cannot pass through the blood brain barrier when administered after birth, the lissencephaly therapeutic effect can hardly be obtained. The lissencephaly therapeutic agent of the present invention is also excellent in this regard.

EXAMPLES

The present invention is described below in more detail. However, the scope of the present invention is not limited to the following Examples. In the following study, well-known textbooks in this field (e.g., Molecular Cloning: A Laboratory Manual (Cold Spring Harbor Laboratory Press), *Kyoushouten Kenbikyou Katsuyou Protocol* [Protocol for Practical Use of Confocal Microscope](Yodosha Company Limited), *Tanpakushitsu Jikken Handbook* [Handbook for Experiments on Proteins](Yodosha Company Limited), and *Nou Shinkei Kenkyu no Susumekata* [How to Proceed with Research on Brain and Nerves](Yodosha Company Limited)) may appropriately be referred to for basic operations, etc.

Synthesis of Each Compound

Compounds 1 to 28 were synthesized to obtain crystals according to the method disclosed in Patent Literature 1 above. Specifically, the synthesis was performed in the following manner. In the analytical values of the following compounds, the melting point was measured using a Yanaco MP-500V (uncorrected). Nuclear magnetic resonance spectra (NMR) were recorded on a Varian Gemini 2000 (300 MHz). Matrix-assisted laser desorption/ionization time-of-flight mass spectra (MALDI-TOF MS) were obtained on a PerSeptive Voyager DE Mass Spectrometer. The mass numbers were corrected with a standard substance (α-cyano-4-hydroxycinnamic acid). The ratio is a volume ratio.

Reference Example 1

N-((2-Methoxyethoxy)carbonyl)-L-leucine N-hydroxysuccinimide ester (1) L-Leucine (25 g, 0.19 mol) was dissolved in a 2M aqueous sodium hydroxide solution (0.12 L), to which chloroformic acid 2-methoxyethyl ester (30 g, 0.22 mol) and a 1M aqueous sodium hydroxide solution were simultaneously and slowly added under ice-cold conditions. This solution was stirred at room temperature for 18 hours, followed by dilution with water (600 mL) and washing with diethyl ether (2×200 mL). The aqueous layer was cooled in an ice bath, and the pH was adjusted to 3 with 6M hydrochloric acid. This solution was extracted with ethyl acetate (5×150 mL). The organic layer was dehydrated with anhydrous magnesium sulfate and concentrated in vacuo to yield N-((2-methoxyethoxy)carbonyl)-L-leucine (41 g, 92%) as a colorless oil.

(2) N-((2-Methoxyethoxy)carbonyl)-L-leucine (20 g, 86 mmol) and N-hydroxysuccinimide (13 g, 0.11 mmol) were dissolved in tetrahydrofuran (200 mL), and a suspension of 1-ethyl-3-(3-dimethylaminopropyl)carbodiimide hydrochloride (21 g, 0.11 mol) in dichloromethane (200 mL) was added thereto. This solution was stirred at room temperature for 18 hours and concentrated in vacuo. The residue was dissolved in ethyl acetate (300 mL), and the solution was washed with 1M hydrochloric acid, saturated aqueous sodium hydrogen carbonate solution, and saturated saline solution, dehydrated with anhydrous magnesium sulfate, and concentrated in vacuo to yield the title compound (27 g, 95%) as a colorless oil.

$^1$H-NMR (300 MHz, DMSO-$d_6$) δ0.89 (d, 3H, J=6.6), 0.93 (d, 3H, J=6.6), 1.57-1.84 (m, 3H), 2.81 (s, 4H), 3.26 (s, 3H), 3.51 (t, 2H, J=4.7), 4.10 (t, 2H, J=4.7), 4.40 (m, 1H), 8.04 (d, 1H, J=8.1).

Reference Example 2

N-(((3S)-Tetrahydrofuran-3-yloxy)carbonyl)-L-leucine N-hydroxysuccinimide ester (1) N,N'-Disuccinimidyl carbonate (4.3 g, 17 mmol) and triethylamine (4.4 g, 17 mmol, 4.8 mL) were added at room temperature to a solution of (S)-3-hydroxytetrahydrofuran (1.0 g, 11 mmol) in acetonitrile (50 mL) with stirring. This solution was stirred at room temperature for 18 hours, and concentrated in vacuo. A saturated aqueous sodium hydrogen carbonate solution (100 mL) was added to the residue, and the mixture was extracted with ethyl acetate (200 mL). The organic layer was washed with a saturated saline solution, dehydrated with anhydrous magnesium sulfate, and concentrated in vacuo to quantitatively yield N-succinimidyl (3S)-3-tetrahydrofuranyl carbonate (2.6 g) as a brown oil.

(2) A solution of N-succinimidyl (3S)-3-tetrahydrofuranyl carbonate (2.6 g, 11 mmol) in dichloromethane (20 mL) was added to a solution of L-leucine ethyl ester hydrochloride (2.7 g, 14 mmol) and triethylamine (2.9 g, 28 mmol) in dichloromethane (50 mL). This reaction solution was stirred at room temperature for 18 hours, and concentrated in vacuo. The residue was dissolved in ethyl acetate (200 mL), and the solution was washed with 1M hydrochloric acid, saturated aqueous sodium hydrogen carbonate solution, and saturated saline solution, dehydrated with anhydrous magnesium sulfate, and concentrated in vacuo. The residue was washed with hexane to yield N-(((3S)-tetrahydrofuran-3-yloxy)carbonyl)-L-leucine ethyl ester (3.1 g, 98%) as a white solid.

(3) A 1M aqueous sodium hydroxide solution (33 mL) was added to a solution of N-(((3S)-tetrahydrofuran-3-yloxy)carbonyl)-L-leucine ethyl ester (2.9 g, 11 mmol) in ethanol (100 mL). This solution was stirred for 3 hours under ice-cold conditions, after which the pH was adjusted to 3 with hydrochloric acid. Ethanol was distilled off in vacuo, and the residue was extracted with ethyl acetate. The organic layer was washed with 1M hydrochloric acid and saturated saline solution, dehydrated with anhydrous magnesium sulfate, and concentrated in vacuo. The residue was crystallized from a liquid mixture of ethyl acetate and hexane mixture, thereby yielding N-(((3S)-tetrahydrofuran-3-yloxy)carbonyl)-L-leucine (2.6 g, 85%) as a colorless crystal.

Melting point: 94.9-96.0° C.

(4) The reaction was performed as in Reference Example 1 (2) by using N-(((3S)-tetrahydrofuran-3-yloxy)carbonyl)-L-leucine in place of N-((2-methoxyethoxy)carbonyl)-L-leucine, thereby yielding the title compound as a colorless oil.

$^1$H-NMR (300 MHz, DMSO-$d_6$) δ0.89 (d, 3H, J=6.0), 0.92 (d, 3H, J=6.3), 1.55-1.82 (m, 3H), 1.88 (m, 1H), 2.12 (m, 1H), 2.81 (s, 4H), 3.64-3.84 (m, 4H), 4.39 (m, 1H), 5.15 (m, 1H), 8.04 (d, 1H, J=7.8).

Reference Example 3

N-((Tetrahydro-4H-pyran-4-yloxy)carbonyl)-L-leucine N-hydroxysuccinimide ester (1) The reaction was performed as in Reference Example 2 (1) by using 4-hydroxytetrahydro-4H-pyran in place of (S)-3-hydroxytetrahydrofuran, thereby yielding N-Succinimidyl tetrahydro-4H-pyran-4-ylcarbonate as a brown oil.

(2) The reaction was performed as in Reference Example 2 (2) by using N-succinimidyl tetrahydro-4H-pyran-4-ylcarbonate in place of N-succinimidyl (3S)-3-tetrahydrofuranyl carbonate, thereby yielding N-((tetrahydro-4H-pyran-4-yloxy)carbonyl)-L-leucine ethyl ester as a colorless solid.

(3) The reaction was performed as in Reference Example 2 (3) by using N-((tetrahydro-4H-pyran-4-yloxy)carbonyl)-L-leucine ethyl ester in place of N-(((3S)-tetrahydrofuran-3-yloxy)carbonyl)-L-leucine ethyl ester, thereby yielding N-((tetrahydro-4H-pyran-4-yloxy)carbonyl)-L-leucine as a colorless solid.

(4) The reaction was performed as in Reference Example 1 (2) by using N-((tetrahydro-4H-pyran-4-yloxy)carbonyl)-L-leucine in place of N-((2-methoxyethoxy)carbonyl)-L-leucine, thereby yielding the title compound as a colorless solid.

$^1$H-NMR (300 MHz, DMSO-d) δ0.89 (d, 3H, J=6.0), 0.92 (d, 3H, J=6.3), 1.43-1.93 (m, 7H), 2.80 (s, 4H), 3.42 (m, 2H), 3.78-3.82 (m, 2H), 4.39 (m, 1H), 4.72 (m, 1H), 7.94 (d, 1H, J=7.8).

Reference Example 4

N-((5-Methoxy-3-oxapentyloxy)carbonyl)-L-leucine N-hydroxysuccinimide ester (1) The reaction was performed as in Reference Example 2 (1) by using diethylene glycol monomethyl ether in place of (S)-3-hydroxytetrahydrofuran, thereby yielding 5-methoxy-3-oxapentyl N-succinimidyl carbonate as a colorless oil.

(2) The reaction was performed as in Reference Example 2 (2) by using 5-methoxy-3-oxapentyl N-succinimidyl carbonate in place of N-succinimidyl (3S)-3-tetrahydrofuranyl carbonate, thereby yielding N-((5-methoxy-3-oxapentyloxy)carbonyl)-L-leucine ethyl ester as a colorless oil.

(3) The reaction was performed as in Reference Example 2 (3) by using N-((5-methoxy-3-oxapentyloxy)carbonyl)-L-leucine ethyl ester in place of N-(((3S)-tetrahydrofuran-3-yloxy)carbonyl)-L-leucine ethyl ester, thereby yielding N-((5-methoxy-3-oxapentyloxy)carbonyl)-L-leucine as a colorless oil.

(4) The reaction was performed as in Reference Example 1 (2) by using N-((5-methoxy-3-oxapentyloxy)carbonyl)-L-leucine in place of N-((2-methoxyethoxy)carbonyl)-L-leucine, thereby yielding the title compound as a colorless oil.

$^1$H-NMR (300 MHz, DMSO-$d_6$) δ0.90 (dd, 6H, J=9.5, 6.5), 1.56-1.80 (m, 3H), 2.80 (s, 4H), 3.24 (s, 3H), 3.41-3.46 (m, 2H), 3.50-3.54 (m, 2H), 3.56-3.60 (m, 2H), 4.08-4.11 (m, 2H), 4.39 (m, 1H), 8.05 (d, 1H, J=7.8).

Reference Example 5

N-((8-Methoxy-3,6-dioxaoctyloxy)carbonyl)-L-leucine N-hydroxysuccinimide ester (1) The reaction was performed as in Reference Example 2 (1) by using triethylene glycol monomethyl ether in place of (S)-3-hydroxytetrahydrofuran, thereby yielding 8-methoxy-3,6-dioxaoctyl N-succinimidyl carbonate as a colorless oil.

(2) The reaction was performed as in Reference Example 2 (2) by using 8-methoxy-3,6-dioxaoctyl N-succinimidyl carbonate in place of N-succinimidyl (3S)-3-tetrahydrofuranyl carbonate, thereby yielding N-((8-methoxy-3,6-dioxaoctyloxy)carbonyl)-L-leucine ethyl ester as a colorless oil.

(3) The reaction was performed as in Reference Example 2 (3) by using N-((8-methoxy-3,6-dioxaoctyloxy)carbonyl)-L-leucine ethyl ester in place of N-(((3S)-tetrahydrofuran-3-yloxy)carbonyl)-L-leucine ethyl ester, thereby yielding N-((8-methoxy-3,6-dioxaoctyloxy)carbonyl)-L-leucine as a colorless oil.

(4) The reaction was performed as in Reference Example 1 (2) by using N-((8-methoxy-3,6-dioxaoctyloxy)carbonyl)-L-leucine in place of N-((2-methoxyethoxy)carbonyl)-L-leucine, thereby yielding the title compound as a colorless oil.

$^1$H-NMR (300 MHz, DMSO-$d_6$) δ0.89 (d, 3H, J=6.3), 0.92 (d, 3H, J=6.3), 1.56-1.82 (m, 3H), 2.81 (s, 4H), 3.24 (s, 3H), 3.43 (m, 2H), 3.52 (m, 6H), 3.59 (m, 2H), 4.10 (m, 2H), 4.40 (m, 1H), 8.06 (d, 1H, J=7.8).

Reference Example 6

N-((11-Methoxy-3,6,9-trioxaundecanyloxy)carbonyl)-L-leucine N-hydroxysuccinimide ester (1) The reaction was performed as in Reference Example 2 (1) by using tetraethylene glycol monomethyl ether in place of (S)-3-hydroxytetrahydrofuran, thereby yielding 11-methoxy-3,6,9-trioxaundecanyl N-succinimidyl carbonate as a colorless oil.

(2) The reaction was performed as in Reference Example 2 (2) by using 11-methoxy-3,6,9-trioxaundecanyl N-succinimidyl carbonate in place of N-succinimidyl (3S)-3-tetrahydrofuranyl carbonate, thereby yielding N-((11-methoxy-3,6,9-trioxaundecanyloxy)carbonyl)-L-leucine ethyl ester as a colorless oil.

(3) The reaction was performed as in Reference Example 2 (3) by using N-((11-methoxy-3,6,9-trioxaundecanyloxy)carbonyl)-L-leucine ethyl ester in place of N-(((3S)-tetrahydrofuran-3-yloxy)carbonyl)-L-leucine ethyl ester, thereby yielding N-((11-methoxy-3,6,9-trioxaundecanyloxy)carbonyl)-L-leucine as a colorless oil.

(4) The reaction was performed as in Reference Example 1 (2) by using N-((11-methoxy-3,6,9-trioxaundecanyloxy)carbonyl)-L-leucine in place of N-((2-methoxyethoxy)carbonyl)-L-leucine, thereby yielding the title compound as a colorless oil.

$^1$H-NMR (300 MHz, DMSO-d$_6$) δ0.91 (dd, 6H, J=9.3, 6.3), 1.56-1.77 (m, 3H), 2.81 (s, 4H), 3.24 (s, 3H), 3.41-3.44 (m, 2H), 3.49-3.52 (m, 10H), 3.59 (t, 2H, J=4.7), 4.08-4.11 (m, 2H), 4.38 (m, 1H), 8.06 (d, 1H, J=7.8).

Reference Example 7

N-((14-Methoxy-3,6,9,12-tetraoxatetradecanyloxy) carbonyl)-L-leucine N-hydroxysuccinimide ester (1) The reaction was performed as in Reference Example 2 (1) by using pentaethylene glycol monomethyl ether in place of (S)-3-hydroxytetrahydrofuran, thereby yielding 14-methoxy-3,6,9,12-tetraoxa tetradecanyl N-succinimidyl carbonate as a colorless oil.

(2) The reaction was performed as in Reference Example 2 (2) by using 14-methoxy-3,6,9,12-tetraoxa tetradecanyl N-succinimidyl carbonate in place of N-succinimidyl (3S)-3-tetrahydrofuranyl carbonate, thereby yielding N-((14-methoxy-3,6,9,12-tetraoxatetradecanyloxy)carbonyl)-L-leucine ethyl ester as a colorless oil.

(3) The reaction was performed as in Reference Example 2 (3) by using N-((14-methoxy-3,6,9,12-tetraoxatetradecanyloxy)carbonyl)-L-leucine ethyl ester) in place of N-(((3S)-tetrahydrofuran-3-yloxy)carbonyl)-L-leucine ethyl ester, thereby yielding N-((14-methoxy-3,6,9,12-tetraoxatetradecanyloxy)carbonyl)-L-leucine as a colorless oil.

(4) The reaction was performed as in Reference Example 1 (2) by using N-((14-methoxy-3,6,9,12-tetraoxatetradecanyloxy)carbonyl)-L-leucine in place of N-((2-methoxyethoxy)carbonyl)-L-leucine, thereby yielding the title compound as a colorless oil.

$^1$H-NMR (300 MHz, DMSO-d$_6$) δ0.89 (d, 3H, J=6.6), 0.92 (d, 3H, J=6.3), 1.57-1.82 (m, 3H), 2.81 (s, 4H), 3.24 (s, 3H), 3.43 (m, 2H), 3.51 (m, 14H), 3.59 (m, 2H), 4.10 (m, 2H), 4.40 (m, 1H), 8.05 (d, 1H, J=7.8).

Reference Example 8

(3S)-3-Amino-N-ethyl-2-hydroxy-4-phenylbutanamide hydrochloride (1) A solution of di-t-butyldicarbonate (140 g, 0.67 mol) in tetrahydrofuran (500 mL) and a 1M aqueous sodium hydroxide solution (660 mL) were simultaneously and slowly added to a solution of L-phenylalaninol (50 g, 66 mmol) in tetrahydrofuran (1.3 L) and water (630 mL) under ice-cold conditions. This solution was stirred at room temperature for 18 hours, and the organic solvent was distilled off in vacuo, after which ethyl acetate (1 L) was added thereto. This solution was washed with 1M hydrochloric acid, saturated aqueous sodium hydrogen carbonate solution, and saturated saline solution, dehydrated with anhydrous magnesium sulfate, and concentrated in vacuo. The obtained white solid was recrystallized from a liquid mixture of ethyl acetate/hexane (1:10), thereby yielding N-(tert-butoxycarbonyl)-L-phenylalaninol (70 g, 84%) as a colorless crystal.

(2) N-(tert-Butoxycarbonyl)-L-phenylalaninol (69 g, 0.28 mol) was dissolved in DMSO (280 mL) and dichloromethane (140 mL), and this solution was cooled in an ice bath. Then, N,N-diisopropylethylamine (110 g, 0.82 mol) and a suspension of purified sulfur trioxide pyridine complex (130 g, 0.82 mol) in DMSO (100 mL) were added thereto. This solution was stirred for 1 hour under ice-cold conditions. The reaction solution was diluted with ethyl acetate (1.5 L), washed with 1M hydrochloric acid, saturated aqueous sodium hydrogen carbonate solution, and saturated saline solution, dehydrated with anhydrous magnesium sulfate, and concentrated in vacuo. The residue was crystallized from a liquid mixture of ethyl acetate/hexane mixture, thereby yielding N-(tert-butoxycarbonyl)-L-phenylalaninal (53 g, 77%) as a colorless crystal.

(3) N-(tert-Butoxycarbonyl)-L-phenylalaninal (17 g, 67 mmol) was dissolved in methanol (100 mL), and the solution was cooled to 5° C. Sodium bisulfite (7.0 g, 67 mmol) was dissolved in water (150 mL) and cooled to 5° C. The solution was added to an aldehyde solution, and the mixture was stirred at 5° C. for 18 hours. Sodium cyanide (4.0 g, 81 mmol) was dissolved in water (100 mL), and added with ethyl acetate (300 mL) to the above reaction mixture. The reaction solution was stirred at room temperature for 5 hours. The organic layer was separated, dehydrated with anhydrous magnesium sulfate, and concentrated in vacuo to yield cyanohydrin as a colorless oil. The cyanohydrin was dissolved in dioxane (250 mL) and concentrated hydrochloric acid (250 mL), followed by the addition of anisole (10 mL). This solution was gently refluxed for 18 hours. The reaction solution was cooled to room temperature and then concentrated in vacuo to yield a brown semi-solid substance. The brown semi-solid substance was dissolved in water (100 mL) and washed with diethyl ether (3×50 mL). The aqueous layer was then applied to a column of Dowex 50×8 (100 to 200 mesh, H+ type; 25×1.8 cm), washed with water until the pH reached 5.5, and eluted with 2M ammonia water (about 1.5 L). The eluted ammonia water was concentrated in vacuo to yield (3S)-3-amino-2-hydroxy-4-phenylbutyric acid (12 g, 88%) as a white solid.

(4) (3S)-3-Amino-2-hydroxy-4-phenylbutyric acid (11 g, 56.34 mmol) was dissolved in a 1M aqueous sodium hydroxide solution (70 mL), and a solution of di-t-butyldicarbonate (12 g, 57 mmol) in dioxane (70 mL) was added thereto. The solution was stirred at room temperature for 18 hours while the pH was maintained between 10 and 11 by the addition of a 1M aqueous sodium hydroxide solution. The mixture was diluted with water (600 mL) and washed with diethyl ether (2×200 mL). While the aqueous layer was cooled in an ice bath, the pH was adjusted to 2 by the addition of 1M hydrochloric acid. Then, the mixture was extracted with diethyl ether (3×250 mL). The organic layer was dehydrated with anhydrous magnesium sulfate, followed by concentration to yield (3S)-3-(tert-butoxycarbonylamino)-2-hydroxy-4-phenylbutyric acid (12 g, 72%) as a colorless solid of a diastereomeric mixture.

(5) (3S)-3-(tert-butoxycarbonylamino)-2-hydroxy-4-phenylbutyric acid (6.3 g, 21 mmol) and 1-hydroxybenzotriazole (3.0 g, 22.4 mmol) were dissolved in DMF (45 mL), and cooled in an ice bath. Thereafter, 1-ethyl-3-(3-dimethylaminopropyl)carbodiimide hydrochloride (4.6 g, 24 mmol) was added thereto, and an aqueous ethylamine solution (3.0 mL) was further added thereto. The solution was stirred for 18 hours. The solution was then diluted with ethyl acetate (200 mL), washed with 1M hydrochloric acid, saturated aqueous sodium hydrogen carbonate solution, and saturated saline solution, dehydrated with anhydrous magnesium sulfate, and concentrated in vacuo, thereby yielding ((1S)-1-benzyl-3-ethylamino-2-hydroxy-3-oxopropyl)carbamic acid 1,1-dimethylethyl ester (5.8 g, 84%) as a white solid.

(6) ((1S)-1-benzyl-3-ethylamino-2-hydroxy-3-oxopropyl)carbamic acid 1,1-dimethylethyl ester (5.5 g, 17 mmol) was dissolved in 4N hydrochloric acid/dioxane solution (65 mL), and the solution was stirred at room temperature for 3 hours. This solution was concentrated in vacuo to quantitatively yield the title compound (4.4 g) as a white solid.

Melting point: 162.8-163.3° C. (Major), $^1$H-NMR (300 MHz, DMSO-$d_6$) δ1.02 (t, 3H, J=7.2), 2.93 (m, 2H), 3.05-3.20 (m, 2H), 3.60 (m, 1H), 3.88 (m, 1H), 6.75 (d, 1H, J=6.0), 7.19-7.37 (m, 5H), 8.08 (m, 1H), 8.17 (br s, 3H). (Minor), $^1$H-NMR (300 MHz, DMSO-$d_6$) δ0.97 (t, 3H, J=7.4), 2.80 (d, 2H, J=6.9), 3.00 (m, 2H), 3.69 (m, 1H), 4.26 (m, 1H), 6.53 (d, 1H, J=5.4), 7.19-7.37 (m, 5H), 8.03 (t, 1H, J=5.7), 8.17 (br s, 3H).

Reference Example 9

(3S)-3-Amino-N-cyclopropyl-2-hydroxy-4-phenylbutanamide hydrochloride

The reaction was performed as in Reference Example 8 (5) by using cyclopropylamine in place of an aqueous ethylamine solution, thereby yielding ((1S)-1-benzyl-3-cyclopropylamino-2-hydroxy)-3-oxopropyl)carbamic acid 1,1-dimethylethyl ester as a white solid.

The reaction was performed as in Reference Example 8 (6) by using ((1S)-1-benzyl-3-cyclopropylamino-2-hydroxy-3-oxopropyl)carbamic acid 1,1-dimethylethyl ester in place of ((1S)-1-benzyl-3-ethylamino-2-hydroxy-3-oxopropyl)carbamic acid 1,1-dimethylethyl ester, thereby yielding the title compound as a white solid.

Melting point: 162.9-163.3° C. $^1$H-NMR (300 MHz, DMSO-$d_6$) δ0.44 (m, 2H), 0.57 (m, 2H), 2.50 (m, 0.5H), 2.65 (m, 0.5H), 2.82 (d, 1H, J=6.9), 2.94 (m, 1H), 3.60 (m, 0.5H), 3.70 (m, 0.5H), 3.87 (m, 0.5H), 4.26 (d, 0.5H, J=2.4), 6.45 (br s, 0.5H), 6.69 (br s, 0.5H), 7.23-7.35 (m, 5H), 7.99 (d, 0.5H, J=4.2), 8.08 (br s, 1.5H), 8.09 (d, 0.5H, J=4.5), 8.23 (br s, 1.5H).

Reference Example 10

(3S)-3-Amino-2-hydroxy-4-phenyl-N-propylbutanamide hydrochloride

The reaction was performed as in Reference Example 8 (5) by using propylamine in place of an aqueous ethylamine solution, thereby yielding ((1S)-1-benzyl-2-hydroxy-3-oxo-3-(propylamino)propyl)carbamic acid 1,1-dimethylethyl ester as a white solid.

The reaction was performed as in Reference Example 8 (6) by using ((1S)-1-benzyl-2-hydroxy-3-oxo-3-(propylamino)propyl)carbamic acid 1,1-dimethylethyl ester in place of ((1S)-1-benzyl-3-ethylamino-2-hydroxy-3-oxopropyl)carbamic acid 1,1-dimethylethyl ester, thereby yielding the title compound as a white solid.

Melting point: 127.8-129.5° C. $^1$H-NMR (300 MHz, DMSO-$d_6$) δ0.82 (m, 3H), 1.35-1.47 (m, 2H), 2.82 (m, 0.5H), 2.95 (m, 3H), 3.09 (m, 0.5H), 3.58 (m, 0.5H), 3.70 (m, 0.5H), 3.92 (m, 0.5H), 4.31 (m, 0.5H), 6.55 (d, 0.5H, J=4.8), 6.77 (d, 0.5H, J=6.6), 7.21-7.36 (m, 5H), 7.98-8.15 (m, 2.5H), 8.24 (br s, 1.5H).

Reference Example 11

(3S)-3-Amino-N-cyclobutyl-2-hydroxy-4-phenylbutanamide hydrochloride

The reaction was performed as in Reference Example 8 (5) by using cyclobutylamine in place of an aqueous ethylamine solution, thereby yielding ((1S)-1-benzyl-3-cyclobutylamino-2-hydroxy-3-oxopropyl)carbamic acid 1,1-dimethylethyl ester as a white solid.

The reaction was performed as in Reference Example 8 (6) by using ((1S)-1-benzyl-3-cyclobutylamino-2-hydroxy-3-oxopropyl)carbamic acid 1,1-dimethylethyl ester in place of ((1S)-1-benzyl-3-ethylamino-2-hydroxy-3-oxopropyl) carbamic acid 1,1-dimethylethyl ester, thereby yielding the title compound as a white solid.

Melting point: 162.5-163.7° C. $^1$H-NMR (300 MHz, DMSO-$d_6$) δ1.59 (m, 2H), 1.88-2.18 (m, 4H), 2.80 (d, 1H, J=6.6), 2.91 (m, 1H), 3.58 (m, 0.5H), 3.69 (m, 0.5H), 3.87 (m, 0.5H), 4.08 (m, 0.5H), 4.16-4.24 (m, 1H), 6.50 (d, 0.5H, J=5.4), 6.72 (d, 0.5H, J=6.0), 7.21-7.33 (m, 5H), 8.05 (br s, 1.5H), 8.19 (d, 0.5H, J=7.8), 8.20 (br s, 1.5H), 8.29 (d, 0.5H, J=8.1).

Reference Example 12

(3S)-3-Amino-N-butyl-2-hydroxy-4-phenylbutanamide hydrochloride

The reaction was performed as in Reference Example 8 (5) by using butylamine in place of an aqueous ethylamine solution, thereby yielding ((1S)-1-benzyl-3-butylamino-2-hydroxy-3-oxopropyl)carbamic acid 1,1-dimethylethyl ester as a white solid.

The reaction was performed as in Reference Example 8 (6) by using ((1S)-1-benzyl-3-butylamino-2-hydroxy-3-oxopropyl)carbamic acid 1,1-dimethylethyl ester in place of ((1S)-1-benzyl-3-ethylamino-2-hydroxy-3-oxopropyl)carbamic acid 1,1-dimethylethyl ester, thereby yielding the title compound as a white solid.

Melting point: 141.0-141.4° C. $^1$H-NMR (300 MHz, DMSO-$d_6$) δ0.86 (m, 3H), 1.16-1.47 (m, 4H), 2.80 (m, 0.5H), 2.99 (m, 3H), 3.13 (m, 0.5H), 3.57 (m, 0.5H), 3.70 (m, 0.5H), 3.92 (m, 0.5H), 4.30 (m, 0.5H), 6.53 (br s, 0.5H), 6.77 (d, 0.5H, J=6.6), 7.19-7.39 (m, 5H), 7.97-8.15 (m, 2.5H), 8.22 (s, 1.5H).

Reference Example 13

(3S)-3-Amino-2-hydroxy-4-phenyl-N-(2,2,2-trifluoroethyl) butanamide hydrochloride The reaction was performed as in Reference Example 8 (5) by using 2,2,2-trifluoroethylamine in place of an aqueous ethylamine solution, thereby yielding ((1S)-1-benzyl-2-hydroxy-3-oxo-3-(2,2,2-trifluoroethylamino)propyl)carbamic acid 1,1-dimethylethyl ester as a white solid.

The reaction was performed as in Reference Example 8 (6) by using ((1S)-1-benzyl-2-hydroxy-3-oxo-3-(2,2,2-trifluoroethylamino)propyl)carbamic acid 1,1-dimethylethyl ester in place of ((1S)-1-benzyl-3-ethylamino-2-hydroxy-3-oxopropyl)carbamic acid 1,1-dimethylethyl ester, thereby yielding (3S)-3-amino-2-hydroxy-4-phenyl-N-(2,2,2-trifluoroethyl)butanamide hydrochloride as a white solid.

Melting point: 103.0-108.5° C. $^1$H-NMR (300 MHz, DMSO-$d_6$) δ2.71-2.85 (m, 1H), 2.88-2.97 (m, 1H), 3.60-3.82 (m, 2.5H), 3.91-4.05 (m, 1H), 4.45 (m, 0.5H), 6.75 (d, 0.5H, J=5.7), 6.98 (d, 0.5H, J=6.3), 7.20-7.35 (m, 5H), 8.12 (br s, 1.5H), 8.25 (br s, 1.5H), 8.70 (m, 1H).

Reference Example 14

(3S)-3-Amino-2-hydroxy-N-(2-indanyl)-4-phenylbutanamide hydrochloride

The reaction was performed as in Reference Example 8 (5) by using 2-aminoindan in place of an aqueous ethylamine solution, thereby yielding ((1S)-1-benzyl-3-(2-indanylamino)-2-hydroxy-3-oxopropyl)carbamic acid 1,1-dimethylethyl ester as a white solid.

The reaction was performed as in Reference Example 8 (6) by using ((1S)-1-benzyl-3-(2-indanylamino)-2-hydroxy-3-oxopropyl)carbamic acid 1,1-dimethylethyl ester in place of ((1S)-1-benzyl-3-ethylamino-2-hydroxy-3-oxopropyl) carbamic acid 1,1-dimethylethyl ester, thereby yielding (3S)-3-amino-2-hydroxy-N-(2-indanyl)-4-phenylbutanamide hydrochloride as a white solid.

Melting point: 183.0-184.8° C. $^1$H-NMR (300 MHz, DMSO-$d_6$) δ2.76-2.96 (m, 4H), 3.01-3.18 (m, 2H), 3.62 (m, 0.5H), 3.74 (m, 0.5H), 3.92 (m, 0.5H), 4.25-4.39 (m, 1H), 4.49 (m, 0.5H), 6.48 (d, 0.5H, J=5.7), 6.72 (d, 0.5H, J=5.7), 7.13-7.35 (m, 9H), 8.15 (m, 3.5H), 8.26 (d, 0.5H, J=7.2).

Reference Example 15

(3S)-3-Amino-2-hydroxy-N-(2-methoxyethyl)-4-phenylbutanamide hydrochloride

The reaction was performed as in Reference Example 8 (5) by using methoxyethylamine in place of an aqueous ethylamine solution, thereby obtaining ((1S)-1-benzyl-2-hydroxy-3-(2-methoxyethyl)-3-oxopropyl)carbamic acid 1,1-dimethylethyl ester as a white solid.

The reaction was performed as in Reference Example 8 (6) by using ((1S)-1-benzyl-2-hydroxy-3-(2-methoxyethyl)-3-oxopropyl)carbamic acid 1,1-dimethylethyl ester in place of ((1S)-1-benzyl-3-ethylamino-2-hydroxy-3-oxopropyl) carbamic acid 1,1-dimethylethyl ester, thereby obtaining (3S)-3-amino-2-hydroxy-N-(2-methoxyethyl)-4-phenylbutanamide hydrochloride as a white solid.

Melting point: 113.9-117.7° C. $^1$H-NMR (300 MHz, DMSO-$d_6$) δ2.82 (d, 1H, J=6.6), 2.95 (m, 1H), 3.10-3.19 (m, 2H), 3.22 (s, 1.5H), 3.23 (s, 1.5H), 3.28-3.34 (m, 2H), 3.57 (m, 0.5H), 3.70 (m, 0.5H), 3.92 (m, 0.5H), 4.32 (m, 0.5H), 6.59 (d, 0.5H, J=4.5), 6.87 (d, 0.5H, J=6.0), 7.22-7.36 (m, 5H), 7.92 (t, 0.5H, J=5.7), 7.98 (t, 0.5H, J=5.1), 8.09 (br s, 1.5H), 8.24 (br s, 1.5H).

Reference Example 16

(3S)-3-Amino-N-ethyl-2-hydroxy-5-phenylpentanamide hydrochloride (1) N-Methylmorpholine (7.2 g, 72 mmol) and isobutyl chlorocarbonate (9.8 g, 72 mmol) were added to a solution of Boc-L-homophenylalanine (20 g, 72 mmol) in dimethoxyethane (100 mL) under ice-cold conditions. After one hour stirring, the reaction solution was filtered, and the filtrate was cooled in an ice bath. Thereafter, an aqueous solution (10 mL) of sodium borohydride (4.1 g, 107 mmol) was added thereto, followed by further addition of water (300 mL). The resulting precipitate was collected by filtration and washed with water and methanol to yield N-(tert-butoxycarbonyl)-L-homophenylalaninol (15 g, 79%) as a colorless crystal.

(2) The reaction was performed as in Reference Example 8 (2) by using N-(tert-butoxycarbonyl)-L-homophenylalaninol in place of N-(tert-butoxycarbonyl)-L-phenylalaninol, thereby yielding N-(tert-butoxycarbonyl)-L-homophenylalaninal as a colorless oil.

(3) The reaction was performed as in Reference Example 8 (3) by using N-(tert-butoxycarbonyl)-L-homophenylalaninal in place of N-(tert-butoxycarbonyl)-L-phenylalaninal, thereby yielding (3S)-3-amino-2-hydroxy-5-phenylpentanoic acid as a white solid.

(4) The reaction was performed as in Reference Example 8 (4) by using (3S)-3-amino-2-hydroxy-5-phenylpentanoic acid in place of (3S)-3-amino-2-hydroxy-4-phenylbutyric acid, thereby yielding (3S)-3-(tert-butoxycarbonylamino)-2-hydroxy-5-phenylpentanoic acid as a colorless oil.

(5) The reaction was performed as in Reference Example 8 (5) by using (3S)-3-(tert-butoxycarbonylamino)-2-hydroxy-5-phenylpentanoic acid in place of (3S)-3-(tert-butoxycarbonylamino)-2-hydroxy-4-phenylbutyric acid, thereby yielding ((1S)-3-ethylamino-2-hydroxy-3-oxo-1-(phenylethyl)propyl)carbamic acid 1,1-dimethylethyl ester as a white solid.

(6) The reaction was performed as in Reference Example 8 (6) by using ((1S)-3-ethylamino-2-hydroxy-3-oxo-1-(phenylethyl)propyl)carbamic acid 1,1-dimethylethyl ester in place of ((1S)-1-benzyl-3-ethylamino-2-hydroxy-3-oxopropyl)carbamic acid 1,1-dimethylethyl ester, thereby yielding (3S)-3-amino-N-ethyl-2-hydroxy-5-phenylpentanamide hydrochloride as a white solid.

Melting point: 134.4-134.9° C. $^1$H-NMR (300 MHz, DMSO-$d_6$) δ0.99-1.06 (m, 3H), 1.65-1.96 (m, 2H), 2.54-2.76 (m, 2H), 3.07-3.23 (m, 2H), 4.15 (br s, 0.5H), 4.25 (br s, 0.5H), 6.44 (br s, 0.5H), 6.55 (br s, 0.5H), 7.17-7.33 (m, 5H), 7.99 (br s, 1.5H), 8.15 (t, 1H, J=6.2), 8.23 (br s, 1.5H).

Reference Example 17

(3S)-3-Amino-N-cyclopropyl-2-hydroxy-5-phenylpentanamide hydrochloride

The reaction was performed as in Reference Example 16 (5) by using cyclopropylamine in place of an aqueous ethylamine solution, thereby yielding ((1S)-3-cyclopropylamino-2-hydroxy-3-oxo-1-(phenylethyl)propyl)carbamic acid 1,1-dimethylethyl ester as a white solid.

The reaction was performed as in Reference Example 16 (6) by using ((1S)-3-cyclopropylamino-2-hydroxy-3-oxo-1-(phenylethyl)propyl)carbamic acid 1,1-dimethylethyl ester in place of ((1S)-1-benzyl-3-ethylamino-2-hydroxy-3-oxopropyl)carbamic acid 1,1-dimethylethyl ester, thereby yielding (3S)-3-amino-N-cyclopropyl-2-hydroxy-5-phenylpentanamide hydrochloride as a white solid.

Melting point: 140.2-141.3° C. $^1$H-NMR (300 MHz, DMSO-$d_6$) δ0.46-0.64 (m, 4H), 1.64-1.99 (m, 2H), 2.54-2.78 (m, 3H), 3.35 (m, 1H), 4.13 (br s, 0.5H), 4.26 (br s, 0.5H), 6.37 (br s, 0.5H), 6.51 (br s, 0.5H), 7.17-7.33 (m, 5H), 8.05 (br s, 1.5H), 8.15 (d, 0.5H, J=4.5), 8.20 (d, 0.5H, J=4.8), 8.27 (br s, 1.5H).

Reference Example 18

(3S)-3-Amino-2-hydroxy-5-methyl-N-(2-phenoxyethyl)hexanamide hydrochloride (1) The reaction was performed as in Reference Example 8 (1) by using L-leucinol in place of L-phenylalaninol, thereby yielding N-(tert-butoxycarbonyl)-L-leucinol (70 g, 84%) as a colorless oil.

(2) The reaction was performed as in Reference Example 8 (2) by using N-(tert-butoxycarbonyl)-L-leucinol in place of N-(tert-butoxycarbonyl)-L-phenylalaninol, thereby yielding N-(tert-butoxycarbonyl)-L-leucinal as a colorless oil.

(3) The reactions were performed as in Reference Examples 8 (3) and 8 (4), by using N-(tert-butoxycarbonyl)-

L-leucinal in place of N-(tert-butoxycarbonyl)-L-phenylalaninal, thereby yielding (3S)-3-(tert-butoxycarbonylamino)-2-hydroxy-5-methyl hexanoic acid as a colorless oil.

(4) The reaction was performed as in Reference Example 8 (5) by using (3S)-3-(tert-butoxycarbonylamino)-2-hydroxy-5-methyl hexanoic acid in place of (3S)-3-(tert-butoxycarbonylamino)-2-hydroxy-4-phenylbutyric acid, and by using 2-phenoxyethylamine in place of an aqueous ethylamine solution, thereby yielding ((1S)-2-hydroxy-1-(2-methylpropyl)-3-oxo-3-(2-phenoxyethyl)aminopropyl carbamic acid 1,1-dimethylethyl ester as a colorless oil.

(5) The reaction was performed as in Reference Example 8 (6) by using ((1S)-2-hydroxy-1-(2-methylpropyl)-3-oxo-3-(2-phenoxyethyl)aminopropyl)carbamic acid 1,1-dimethylethyl ester in place of ((1S)-1-benzyl-3-ethylamino-2-hydroxy-3-oxopropyl)carbamic acid 1,1-dimethylethyl ester, thereby yielding the title compound as a white solid.

Melting point: 93.6-96.2° C. $^1$H-NMR (300 MHz, DMSO-$d_6$) δ0.71-0.89 (m, 6H), 1.35-1.47 (m, 2H), 1.72 (m, 1H), 3.48-3.54 (m, 4H), 4.00-4.07 (m, 2H), 4.12 (d, 0.5H, J=3.6), 4.33 (d, 0.5H, J=1.8), 6.91-6.96 (m, 3H), 7.27-7.32 (m, 2H), 7.95 (br s, 1.5H), 8.19-8.29 (m, 2.5H).

Reference Example 19

3-Amino-2-hydroxy-5-phenylpentanamide hydrochloride

The reaction was performed as in Reference Example 8 (5) by using ammonia gas in place of an aqueous ethylamine solution, thereby yielding (1-benzyl-3-amino-2-hydroxy-3-oxopropyl)carbamic acid 1,1-dimethylethyl ester as a white solid.

The reaction was performed as in Reference Example 8 (6) by using (1-benzyl-3-amino-2-hydroxy-3-oxopropyl) carbamic acid 1,1-dimethylethyl ester in place of ((1S)-1-benzyl-3-ethylamino-2-hydroxy-3-oxopropyl)carbamic acid 1,1-dimethylethyl ester, thereby yielding the title compound as a white solid.

$^1$H-NMR (300 MHz, DMSO-$d_6$) δ2.82 (m, 1H), 2.93 (m, 1H), 3.61 (m, 1H), 3.85 (m, 0.5H), 4.26 (m, 0.5H), 6.48 (d, 0.5H, J=4.8), 6.75 (d, 0.5H, J=5.7), 7.24-7.35 (m, 5H), 7.52 (m, 2H), 8.04 (brs, 1.5H), 8.17 (brs, 1.5H).

Reference Example 20

N-((2-(Pyridin-2-yl)ethyl)carbonyl)-L-leucine N-hydroxysuccinimide ester (1) The reaction was performed as in Reference Example 2 (1) by using (2-pyridyl)ethanol in place of (S)-3-hydroxytetrahydrofuran, thereby yielding N-succinimidyl 2-(pyridin-2-yl)ethyl carbonate as a brown oil.

(2) The reaction was performed as in Reference Example 2 (2) by using N-succinimidyl 2-(pyridin-2-yl)ethyl carbonate in place of N-succinimidyl(3S)-3-tetrahydrofuranyl carbonate, thereby yielding N-((2-(pyridin-2-yl)ethyloxy)carbonyl)-L-leucine ethyl ester as a colorless oil.

(3) The reaction was performed as in Reference Example 2 (3) by using N-((2-(pyridin-2-yl)ethyloxy)carbonyl)-L-leucine ethyl ester in place of N-(((3S)-tetrahydrofuran-3-yloxy)carbonyl)-L-leucine ethyl ester, thereby yielding N-((2-(pyridin-2-yl)ethyloxy)carbonyl)-L-leucine as a white solid.

(4) The reaction was performed as in Reference Example 1 (2) by using N-((2-(pyridin-2-yl)ethyloxy)carbonyl)-L-leucine) in place of N-((2-methoxyethoxy)carbonyl)-L-leucine, thereby yielding the title compound as a colorless oil.

$^1$H-NMR (300 MHz, DMSO-$d_6$) δ0.82-0.91 (m, 6H), 1.42-1.76 (m, 3H), 2.76-2.81 (m, 4H), 3.00-3.06 (m, 2H), 4.30-4.40 (m, 3H), 7.23 (dd, 1H, J=7.1, 5.3), 7.30 (d, 1H, J=7.8), 7.71 (m, 1H), 7.90 (d, 1H, J=8.1), 8.50 (d, 1H, J=4.5).

Reference Example 21

N-((2-(6-Methylpyridin-2-yl)ethyloxy)carbonyl)-L-leucine N-hydroxysuccinimide ester (1) The reaction was performed as in Reference Example 2 (1) by using 2-(6-methyl-2-pyridyl)ethanol in place of (S)-3-hydroxytetrahydrofuran, thereby yielding N-succinimidyl 2-(6-methylpyridin-2-yl)ethyl carbonate as a brown oil.

(2) The reaction was performed as in Reference Example 2 (2) by using N-succinimidyl 2-(6-methylpyridin-2-yl)ethyl carbonate in place of N-succinimidyl (3S)-3-tetrahydrofuranyl carbonate, thereby yielding N-((2-(6-methylpyridin-2-yl)ethyloxy)carbonyl)-L-leucine ethyl ester as a colorless oil.

(3) The reaction was performed as in Reference Example 2 (3) by using N-((2-(6-methylpyridin-2-yl)ethyloxy)carbonyl)-L-leucine ethyl ester in place of N-(((3S)-tetrahydrofuran-3-yloxy)carbonyl)-L-leucine ethyl ester, thereby yielding N-((2-(6-methylpyridin-2-yl)ethyloxy)carbonyl)-L-leucine as a colorless oil.

(4) The reaction was performed as in Reference Example 1 (2) by using N-((2-(6-methylpyridin-2-yl)ethyloxy)carbonyl)-L-leucine in place of N-((2-methoxyethyloxy)carbonyl)-L-leucine, thereby yielding the title compound as a colorless oil.

$^1$H-NMR (300 MHz, DMSO-$d_6$) δ0.83-0.92 (m, 6H), 1.49-1.77 (m, 3H), 2.43 (s, 3H), 2.81 (s, 4H), 2.99 (t, 2H, J=6.5), 4.29-4.42 (m, 3H), 7.07-7.09 (m, 2H), 7.58 (t, 1H, J=7.7), 7.91 (d, 1H, J=8.4).

Reference Example 22

N-((2-(5-Ethylpyridin-2-yl)ethyloxy)carbonyl)-L-leucine N-hydroxysuccinimide ester (1) The reaction was performed as in Reference Example 2 (1) by using (5-ethylpyridin-2-yl)ethanol in place of (S)-3-hydroxytetrahydrofuran, thereby yielding N-succinimidyl 2-(5-ethylpyridin-2-yl)ethyl carbonate as a brown oil.

(2) The reaction was performed as in Reference Example 2 (2) by using N-succinimidyl 2-(5-ethylpyridin-2-yl)ethyl carbonate in place of N-succinimidyl(3S)-3-tetrahydrofuranyl carbonate, thereby yielding N-((2-(5-ethylpyridin-2-yl) ethyloxy)carbonyl)-L-leucine ethyl ester as a colorless oil.

(3) The reaction was performed as in Reference Example 2 (3) by using N-((2-(5-ethylpyridin-2-yl)ethyloxy)carbonyl)-L-leucine ethyl ester in place of N-(((3S)-tetrahydrofuran-3-yloxy)carbonyl)-L-leucine ethyl ester, thereby yielding N-((2-(5-ethylpyridin-2-yl)ethyloxy)carbonyl)-L-leucine as a colorless oil.

(4) The reaction was performed as in Reference Example 1 (2) by using N-((2-(5-ethylpyridin-2-yl)ethyloxy)carbonyl)-L-leucine in place of N-((2-methoxyethoxy)carbonyl)-L-leucine, thereby yielding the title compound as a colorless oil.

$^1$H-NMR (300 MHz, DMSO-d$_6$) δ0.75-0.92 (m, 6H), 1.12-1.25 (m, 3H), 1.36-1.72 (m, 3H), 2.54-2.63 (m, 2H), 2.81-2.83 (m, 4H), 2.96-3.02 (m, 2H), 4.04 (m, 1H), 4.29-4.37 (m, 2H), 7.21 (d, 1H, J=7.8), 7.53 (m, 1H), 7.90 (d, 1H, J=7.8), 8.34 (m, 1H).

Reference Example 23

N-((2-tert-Butoxyethyloxy)carbonyl)-L-leucine N-hydroxysuccinimide ester (1) The reaction was performed as in Reference Example 2 (1) by using ethylene glycol tert-butyl ether in place of (S)-3-hydroxytetrahydrofuran, thereby yielding N-succinimidyl 2-tert-butoxyethyl carbonate as a colorless oil.

(2) The reaction was performed as in Reference Example 2 (2) by using N-succinimidyl 2-tert-butoxyethyl carbonate in place of N-succinimidyl (3S)-3-tetrahydrofuranyl carbonate, thereby yielding N-((2-tert-butoxyethyloxy)carbonyl)-L-leucine ethyl ester as a colorless oil.

(3) The reaction was performed as in Reference Example 2 (3) by using N-((2-tert-butoxyethyloxy)carbonyl)-L-leucine ethyl ester in place of N-(((3S)-tetrahydrofuran-3-yloxy)carbonyl)-L-leucine ethyl ester, thereby yielding N-((2-tert-butoxyethyloxy)carbonyl)-L-leucine as a colorless oil.

(4) The reaction was performed as in Reference Example 1 (2) by using N-((2-tert-butoxyethyloxy)carbonyl)-L-leucine in place of N-((2-methoxyethyloxy)carbonyl)-L-leucine, thereby yielding the title compound as a colorless oil.

$^1$H-NMR (300 MHz, DMSO-d$_6$) δ0.89 (d, 3H, J=6.3), 0.92 (d, 3H, J=6.3), 1.13 (s, 9H), 1.61 (m, 1H), 1.74 (m, 2H), 2.81 (s, 4H), 3.48 (t, 2H, J=4.7), 4.04 (m, 2H), 4.40 (m, 1H), 8.00 (d, 1H, J=7.8).

Reference Example 24

N-((2-Isopropoxyethyloxy)carbonyl)-L-leucine N-hydroxysuccinimide ester (1) The reaction was performed as in Reference Example 2 (1) by using ethylene glycol isopropyl ether in place of (S)-3-hydroxytetrahydrofuran, thereby yielding N-succinimidyl 2-isopropoxyethyl carbonate as a colorless oil.

(2) The reaction was performed as in Reference Example 2 (2) by using N-succinimidyl 2-isopropoxyethyl carbonate in place of N-succinimidyl (3S)-3-tetrahydrofuranyl carbonate, thereby yielding N-((2-isopropoxyethyloxy)carbonyl)-L-leucine ethyl ester as a colorless oil.

(3) The reaction was performed as in Reference Example 2 (3) by using N-((2-isopropoxyethyloxy)carbonyl)-L-leucine ethyl ester in place of N-(((3S)-tetrahydrofuran-3-yloxy)carbonyl)-L-leucine ethyl ester, thereby yielding N-((2-isopropoxyethyloxy)carbonyl)-L-leucine as a colorless oil.

(4) The reaction was performed as in Reference Example 1 (2) by using N-((2-isopropoxyethyloxy)carbonyl)-L-leucine in place of N-((2-methoxyethyloxy)carbonyl)-L-leucine, thereby yielding the title compound as a colorless oil.

$^1$H-NMR (300 MHz, DMSO-d$_6$) δ0.89 (d, 3H, J=6.6), 0.92 (d, 3H, J=6.3), 1.08 (d, 6H, J=6.3), 1.61 (m, 1H), 1.74 (m, 2H), 2.81 (s, 4H), 3.53 (m, 2H), 3.57 (m, 1H), 4.07 (m, 2H), 4.40 (m, 1H), 8.02 (d, 1H, J=7.8).

Production Example 1

((1S)-1-((((1S)-1-Benzyl-2,3-dioxo-3-(ethylamino) propyl)amino)carbonyl)-3-methylbutyl) carbamic acid 2-methoxyethyl ester (Compound 1)

[Chem. 51]

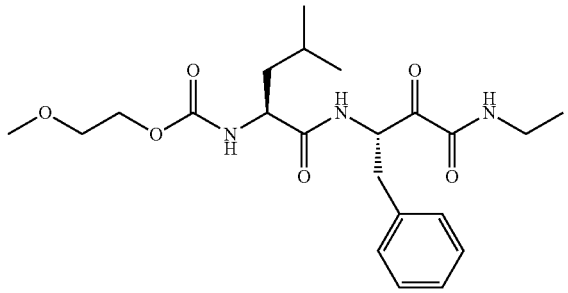

Triethylamine (1.1 g, 11 mmol) was added to a solution of the compound of Reference Example 1 (1.2 g, 3.6 mmol) and the compound of Reference Example 8 (1.0 g, 4.0 mmol) in DMF. This solution was stirred at room temperature for 18 hours and concentrated in vacuo. The residue was dissolved in ethyl acetate, and the solution was washed with 1M hydrochloric acid, saturated aqueous sodium hydrogen carbonate solution, and saturated saline solution, dehydrated with anhydrous magnesium sulfate, and concentrated in vacuo. The resulting solid was washed with a liquid mixture of ethyl acetate/hexane (1:9) to yield ((1S)-1-((((1S)-1-benzyl-3-ethylamino-2-hydroxy-3-oxopropyl)amino)carbonyl)-3-methylbutyl)carbamic acid 2-methoxyethyl ester (0.75 g, 47%) as a white solid. A Dess-Martin reagent (1.0 g, 2.4 mmol) was added to a solution of ((1S)-1-((((1S)-1-benzyl-3-ethylamino-2-hydroxy-3-oxopropyl)amino)carbonyl)-3-methylbutyl)carbamic acid 2-methoxyethyl ester (0.7 g, 1.6 mmol) in dichloromethane (70 mL), and the resulting solution was stirred at room temperature for 18 hours. Thereafter, a 10% aqueous sodium thiosulfate solution (35 mL) and a saturated aqueous sodium hydrogen carbonate solution (35 mL) were added thereto, and the mixture was stirred at room temperature for 30 minutes. The organic layer was separated, washed with 1M hydrochloric acid, saturated aqueous sodium hydrogen carbonate solution, and saturated saline solution, dehydrated with anhydrous magnesium sulfate, and concentrated in vacuo. The residue was crystallized from a liquid mixture of ethyl acetate/hexane to yield the title compound (0.62 g, 88%) as a colorless crystal.

Melting point: 138.0-138.3° C. $^1$H-NMR (300 MHz, DMSO-d$_6$) δ0.83 (d, 3H, J=7.5), 0.85 (d, 3H, J=7.2), 1.04 (t, 3H, J=7.1), 1.35 (m, 2H), 1.56 (m, 1H), 2.82 (m, 1H), 3.14 (m, 3H), 3.25 (s, 3H), 3.47 (t, 2H, J=4.5), 4.04 (m, 3H), 5.19

(m, 1H), 7.16-7.33 (m, 6H), 8.24 (d, 1H, J=7.2), 8.70 (m, 1H). MALDI-TOF-MS: $C_{22}H_{33}N_3O_6$ (M+Na)$^+$, 458.2267, Actual measurement value, 458.2361

Production Example 2

((1S)-1-((((1S)-1-Benzyl-2,3-dioxo-3-(ethylamino) propyl)amino)carbonyl)-3-methylbutyl)carbamic acid (3S)-tetrahydrofuran-3-yl ester (compound 2)

[Chem. 52]

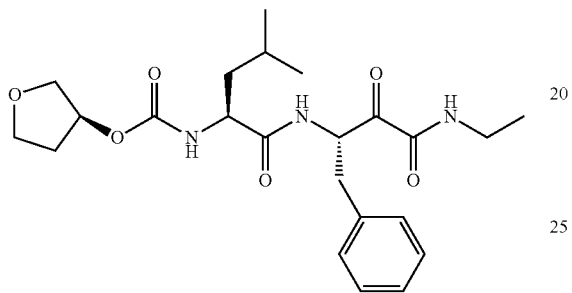

The reaction was performed as in Production Example 1 by using the compound of Reference Example 2 in place of the compound of Reference Example 1, thereby obtaining the title compound as a colorless crystal, via ((1S)-1-((((1S)-1-benzyl-3-ethylamino-2-hydroxy-3-oxopropyl)amino)carbonyl)-3-methylbutyl)carbamic acid (3S)-tetrahydrofuran-3-yl ester. Melting point: 158.9-160.7° C. $^1$H-NMR (300 MHz, DMSO-$d_6$) δ0.83 (d, 3H, J=6.6), 0.85 (d, 3H, J=6.9), 1.04 (t, 3H, J=7.1), 1.35 (m, 2H), 1.55 (m, 1H), 1.83 (m, 1H), 2.08 (m, 1H), 2.82 (m, 1H), 3.14 (m, 3H), 3.61-3.78 (m, 4H), 4.01 (m, 1H), 5.07 (m, 1H), 5.19 (m, 1H), 7.17-7.33 (m, 6H), 8.22 (d, 1H, J=7.2), 8.69 (t, 1H, J=5.7). MALDI-TOF-MS: $C_{23}H_{33}N_3O_6$ (M+H)$^+$, 448.2447, Actual measurement value, 448.2509.

Production Example 3

((1S)-1-((((1S)-1-Benzyl-2,3-dioxo-3-(ethylamino) propyl)amino)carbonyl)-3-methylbutyl)carbamic acid tetrahydro-4H-pyran-4-yl ester (compound 3)

[Chem. 53]

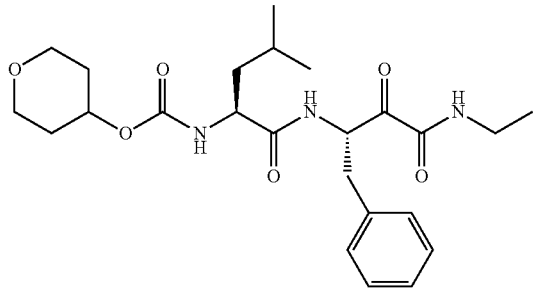

The reaction was performed as in Production Example 1 by using the compound of Reference Example 3 in place of the compound of Reference Example 1, thereby obtaining the title compound as a colorless crystal, via ((1S)-1-((((1S)-1-benzyl-3-ethylamino-2-hydroxy-3-oxopropyl)amino)carbonyl)-3-methylbutyl)carbamic acid tetrahydro-4H-pyran-4-yl ester.

Melting point: 140.0-141.8° C. $^1$H-NMR (300 MHz, DMSO-$d_6$) δ0.84 (m, 6H), 1.04 (t, 3H, J=7.2), 1.35 (m, 2H), 1.49 (m, 3H), 1.79 (m, 2H), 2.82 (m, 1H), 3.14 (m, 3H), 3.41 (m, 2H), 3.78 (m, 2H), 4.02 (m, 1H), 4.66 (m, 1H), 5.19 (m, 1H), 7.15-7.33 (m, 6H), 8.22 (d, 1H, J=7.2), 8.69 (t, 1H, J=5.7). MALDI-TOF-MS: $C_{24}H_{35}N_3O_6$ (M+Na)$^+$, 484.2424, Actual measurement value, 484.2486.

Production Example 4

((1S)-1-((((1S)-1-Benzyl-2,3-dioxo-3-(cyclopropylamino)propyl)amino)carbonyl)-3-methylbutyl)carbamic acid 2-methoxyethyl ester (compound 4)

[Chem. 54]

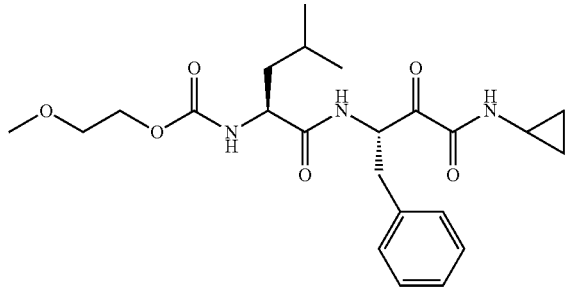

The reaction was performed as in Production Example 1 by using the compound of Reference Example 9 in place of the compound of Reference Example 8, thereby obtaining the title compound as a colorless crystal, via ((1S)-1-((((1S)-1-benzyl-3-cyclopropylamino-2-hydroxy-3-oxopropyl) amino)carbonyl)-3-methylbutyl)carbamic acid 2-methoxyethyl ester.

Melting point: 112.4-113.5° C. $^1$H-NMR (300 MHz, DMSO-d) δ0.58 (m, 2H), 0.65 (m, 2H), 0.83 (d, 3H, J=6.6), 0.85 (d, 3H, J=6.6), 1.35 (m, 2H), 1.56 (m, 1H), 2.68-2.88 (m, 2H), 3.11 (m, 1H), 3.25 (s, 3H), 3.47 (t, 2H, J=4.5), 4.04 (m, 3H), 5.17 (m, 1H), 7.17-7.34 (m, 6H), 8.25 (d, 1H, J=7.2), 8.73 (d, 1H, J=4.8). MALDI-TOF-MS: $C_{23}H_{33}N_3O_6$ (M+Na)$^+$, 470.2267, Actual measurement value, 470.2441. $[α]^{25}$+6.3° (c0.20, DMSO)

Production Example 5

((1S)-1-((((1S)-1-Benzyl-3-(cyclopropylamino)-2,3-dioxopropyl)amino)carbonyl)-3-methylbutyl)carbamic acid (3S)-tetrahydrofuran-3-yl ester (compound 5)

[Chem. 55]

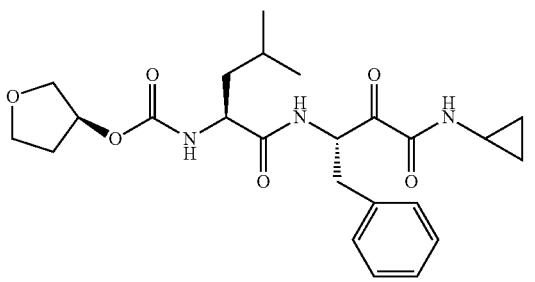

The reaction was performed as in Production Example 1 by using the compound of Reference Example 2 in place of the compound of Reference Example 1, and by using the compound of Reference Example 9 in place of the compound of Reference Example 8, thereby yielding the title compound as a colorless crystal, via ((1S)-1-((((1S)-1-benzyl-3-cyclopropylamino-2-hydroxy-3-oxopropyl)amino)carbonyl)-3-methylbutyl) carbamic acid (3S)-tetrahydrofuran-3-yl ester.

Melting point: 169.2-170.5° C. $^1$H-NMR (300 MHz, DMSO-d$_6$) δ0.58 (m, 2H), 0.65 (m, 2H), 0.83 (d, 3H, J=8.1), 0.85 (d, 3H, J=6.9), 1.34 (m, 2H), 1.55 (m, 1H), 1.83 (m, 1H), 2.08 (m, 1H), 2.79 (m, 2H), 3.12 (m, 1H), 3.61-3.80 (m, 4H), 4.02 (m, 1H), 5.08 (m, 1H), 5.17 (m, 1H), 7.22-7.35 (m, 6H), 8.24 (d, 1H, J=6.6), 8.74 (d, 1H, J=5.1). MALDI-TOF-MS: $C_{24}H_{33}N_3O_6$ (M+Na)$^+$, 482.2267, Actual measurement value, 482.2586.

Production Example 6

((1S)-1-((((1S)-1-Benzyl-3-cyclopropylamino-2,3-dioxopropyl)amino)carbonyl)-3-methylbutyl)carbamic acid tetrahydro-4H-pyran-4-yl ester (compound 6)

[Chem. 56]

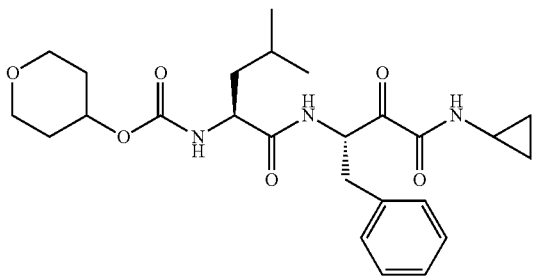

The reaction was performed as in Production Example 1 by using the compound of Reference Example 3 in place of the compound of Reference Example 1, and by using the compound of Reference Example 9 in place of the compound of Reference Example 8, thereby yielding the title compound as a colorless crystal, via ((1S)-1-((((1S)-1-benzyl-3-cyclopropylamino-2-hydroxy-3-oxopropyl)amino)carbonyl)-3-methylbutyl)carbamic acid tetrahydro-4H-pyran-4-yl ester.

Melting point: 137.0-138.2° C. $^1$H-NMR (300 MHz, DMSO-d$_6$) δ0.58 (m, 2H), 0.65 (m, 2H), 0.84 (m, 6H), 1.35 (m, 2H), 1.48 (m, 3H), 1.80 (m, 2H), 2.79 (m, 2H), 3.11 (m, 1H), 3.41 (m, 2H), 3.79 (m, 2H), 4.03 (m, 1H), 4.65 (m, 1H), 5.18 (m, 1H), 7.15-7.30 (m, 6H), 8.23 (d, 1H, J=6.9), 8.73 (d, 1H, J=5.4). MALDI-TOF-MS: $C_{25}H_{35}N_3O_6$ (M+H)$^+$, 474.2604, Actual measurement value, 474.2643.

Production Example 7

((1S)-1-((((1S)-1-Benzyl-2,3-dioxo-3-(propylamino)propyl)amino)carbonyl)-3-methylbutyl)carbamic acid 2-methoxyethyl ester (compound 7)

[Chem. 57]

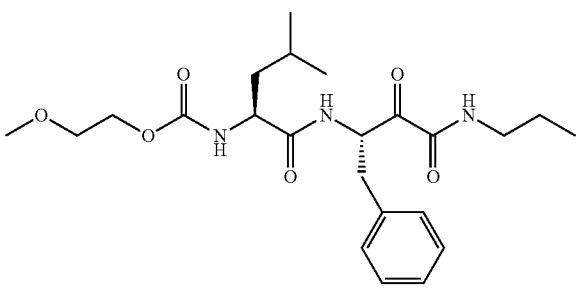

The reaction was performed as in Production Example 1 by using the compound of Reference Example 10 in place of the compound of Reference Example 8, thereby yielding the title compound as a colorless crystal, via ((1S)-1-((((1S)-1-benzyl-2-hydroxy-3-oxo-3-(propylamino)propyl)amino)carbonyl)-3-methylbutyl)carbamic acid 2-methoxyethyl ester.

Melting point: 108.8-109.9° C. $^1$H-NMR (300 MHz, DMSO-d$_6$) δ0.83 (m, 9H), 1.35 (m, 2H), 1.46 (m, 2H), 1.55 (m, 1H), 2.83 (dd, 1H, J=14.0, 9.2), 3.08 (m, 3H), 3.25 (s, 3H), 3.48 (t, 2H, J=4.4), 4.04 (m, 3H), 5.19 (m, 1H), 7.22-7.28 (m, 6H), 8.24 (d, 1H, J=6.9), 8.68 (t, 1H, J=5.6). MALDI-TOF-MS: $C_{23}H_{35}N_3O_6$ (M+H)$^+$, 450.2604, Actual measurement value, 450.2832.

Production Example 8

((1S)-1-((((1S)-1-Benzyl-2,3-dioxo-3-(cyclobutylamino)propyl)amino)carbonyl)-3-methylbutyl)carbamic acid 2-methoxyethyl ester (compound 8)

[Chem. 58]

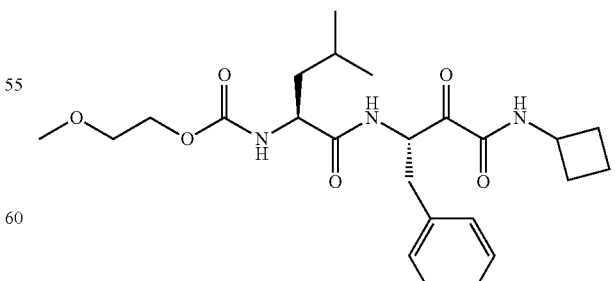

The reaction was performed as in Production Example 1 by using the compound of Reference Example 11 in place of the compound of Reference Example 8, thereby yielding the title compound as a colorless crystal, via ((1S)-1-((((1S)-1- benzyl-3-cyclobutylamino-2-hydroxy-3-oxopropyl)amino)carbonyl)-3-methylbutyl)carbamic acid 2-methoxyethyl ester.

Melting point: 114.2-115.3° C. $^1$H-NMR (300 MHz, DMSO-$d_6$) δ0.84 (m, 6H), 1.34 (m, 2H), 1.49-1.72 (m, 3H), 2.10 (m, 4H), 2.81 (dd, 1H, J=13.8, 9.3), 3.10 (m, 1H), 3.25 (s, 3H), 3.47 (m, 2H), 4.03 (m, 3H), 4.22 (m, 1H), 5.15 (m, 1H), 7.24 (m, 6H), 8.24 (d, 1H, J=7.2), 8.91 (d, 1H, J=7.8). MALDI-TOF-MS: $C_{24}H_{35}N_3O_6$ (M+Na)$^+$, 484.2424, Actual measurement value, 484.2400.

Production Example 9

((1S)-1-((((1S)-1-Benzyl-3-butylamino-2,3-dioxopropyl)amino)carbonyl)-3-methylbutyl)carbamic acid 2-methoxyethyl ester (compound 9)

[Chem. 59]

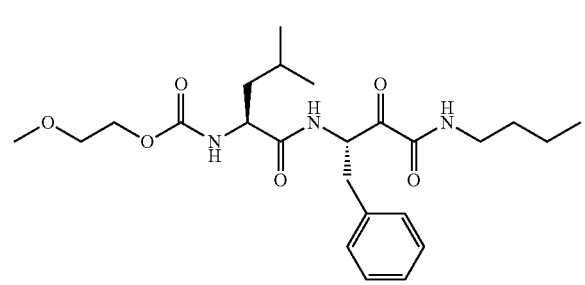

The reaction was performed as in Production Example 1 by using the compound of Reference Example 12 in place of the compound of Reference Example 8, thereby yielding the title compound as a colorless crystal, via ((1S)-1-((((1S)-1-benzyl-3-butylamino-2-hydroxy-3-oxopropyl)amino)carbonyl)-3-methylbutyl)carbamic acid 2-methoxyethyl ester.

Melting point: 94.0-95.2° C. $^1$H-NMR (300 MHz, DMSO-$d_6$) δ0.85 (m, 9H), 1.25 (m, 2H), 1.35 (m, 2H), 1.42 (m, 2H), 1.56 (m, 1H), 2.83 (dd, 1H, J=13.8, 9.0), 3.10 (m, 3H), 3.25 (s, 3H), 3.47 (t, 2H, J=4.5), 4.04 (m, 3H), 5.18 (m, 1H), 7.21-7.29 (m, 6H), 8.23 (d, 1H, J=6.6), 8.67 (t, 1H, J=6.0). MALDI-TOF-MS: $C_{24}H_{37}N_3O_6$ (M+H)$^+$, 464.2760, Actual measurement value, 464.2870.

Production Example 10

((1S)-1-((((1S)-1-Benzyl-2,3-dioxo-3-(2,2,2-trifluoroethylamino)propyl)amino)carbonyl)-3-methylbutyl)carbamic acid 2-methoxyethyl ester (compound 10)

[Chem. 60]

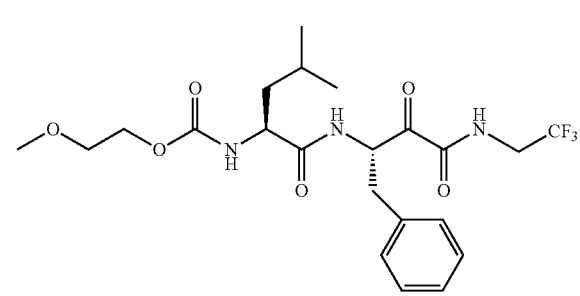

The reaction was performed as in Production Example 1 by using the compound of Reference Example 13 in place of the compound of Reference Example 8, thereby yielding the title compound as a colorless crystal, via ((1S)-1-((((1S)-1-benzyl-2-hydroxy-3-oxo-3-(2,2,2-trifluoroethylamino)propyl)amino)carbonyl)-3-methylbutyl)carbamic acid 2-methoxyethyl ester.

Melting point: 152.5-153.9° C. $^1$H-NMR (300 MHz, DMSO-$d_6$) δ0.84 (m, 6H), 1.34 (m, 2H), 1.55 (m, 1H), 2.86 (dd, 1H, J=14.0, 8.6), 3.10 (dd, 1H, J=14.1, 4.8), 3.25 (s, 3H), 3.48 (t, 2H, J=4.7), 3.90 (m, 2H), 4.04 (m, 3H), 5.14 (m, 1H), 7.21-7.31 (m, 6H), 8.34 (d, 1H, J=6.9), 9.29 (m, 1H). MALDI-TOF-MS: $C_{22}H_{30}F_3N_3O_6$ (M+H)$^+$, 490.2165, Actual measurement value, 490.2434.

Production Example 11

((1S)-1-((((1S)-1-Benzyl-2, 3-dioxo-3-(2-indanylamino)propyl)amino)carbonyl)-3-methylbutyl)carbamic acid 2-methoxyethyl ester (compound 11)

[Chem. 61]

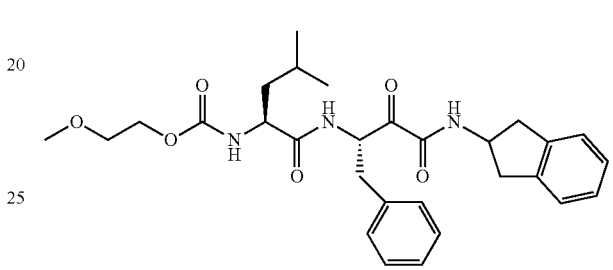

The reaction was performed as in Production Example 1 by using the compound of Reference Example 14 in place of the compound of Reference Example 8, thereby yielding the title compound as a colorless crystal, via ((1S)-1-((((1S)-1-benzyl-2-hydroxy-3-(2-indanylamino)-3-oxopropyl)amino)carbonyl)-3-methylbutyl)carbamic acid 2-methoxyethyl ester.

Melting point: 141.9-143.5° C. $^1$H-NMR (300 MHz, DMSO-$d_6$) δ0.83 (d, 3H, J=6.9), 0.86 (d, 3H, J=6.9), 1.36 (m, 2H), 1.57 (m, 1H), 2.80-2.96 (m, 3H), 3.10-3.18 (m, 3H), 3.24 (s, 3H), 3.47 (t, 2H, J=4.7), 4.04 (m, 3H), 4.50 (m, 1H), 5.19 (m, 1H), 7.13-7.30 (m, 10H), 8.29 (d, 1H, J=6.9), 8.97 (d, 1H, J=7.2). MALDI-TOF-MS: $C_{29}H_{37}N_3O_6$ (M+H)$^+$, 524.2760, Actual measurement value, 524.2810.

Production Example 12

((1S)-1-((((1S)-1-Benzyl-2,3-dioxo-3-(2-methoxyethylamino)propyl)amino)carbonyl)-3-methylbutyl)carbamic acid 2-methoxyethyl ester (compound 12)

[Chem. 62]

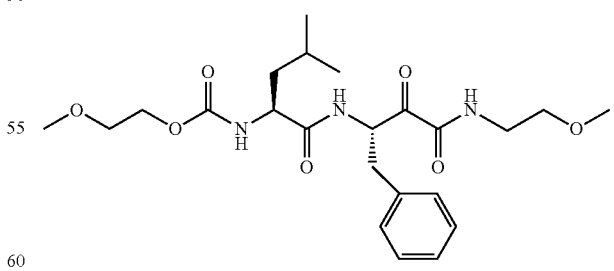

The reaction was performed as in Production Example 1 by using the compound of Reference Example 15 in place of the compound of Reference Example 8, thereby yielding the title compound as a colorless crystal, via ((1S)-1-((((1S)-1-benzyl-2-hydroxy-3-(2-methoxyethylamino)-3-oxopropyl)amino)carbonyl)-3-methylbutyl)carbamic acid 2-methoxyethyl ester.

Melting point: 127.0-127.9° C. $^1$H-NMR (300 MHz, DMSO-d$_6$) 0.83 (d, 3H, J=6.9), 0.86 (d, 3, J=6.9), 1.35 (m, 2H), 1.56 (m, 1H), 2.83 (dd, 1H, J=13.8, 9.0), 3.11 (dd, 1H, J=14.0, 4.4), 3.24 (s, 3H), 3.25 (s, 3H), 3.16-3.34 (m, 2H), 3.39 (m, 2H), 3.48 (t, 2H, J=4.5), 4.04 (m, 3H), 5.20 (m, 1H), 7.18-7.30 (m, 6H), 8.21 (d, 1H, J=6.9), 8.66 (t, 1H, J=5.4). MALDI-TOF-MS: C$_{23}$H$_{35}$N$_3$O$_7$ (M+Na)$^+$, 488.2373, Actual measurement value, 488.2680.

Production Example 13

((1S)-1-((((1S)-2,3-Dioxo-3-ethylamino-1-(phenylethyl)propyl)amino)carbonyl)-3-methylbutyl)carbamic acid 2-methoxyethyl ester (compound 13)

[Chem. 63]

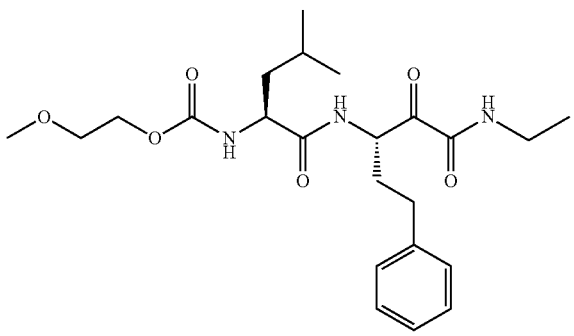

The reaction was performed as in Production Example 1 by using the compound of Reference Example 16 in place of the compound of Reference Example 8, thereby yielding the title compound as a colorless crystal, via ((1S)-1-((((1S)-3-ethylamino-2-hydroxy-3-oxo-1-(phenylethyl)propyl)amino)carbonyl)-3-methylbutyl)carbamic acid 2-methoxyethyl ester.
Melting point: 119.1-120.4° C. $^1$H-NMR (300 MHz, DMSO-d$_6$) δ0.89 (t, 6H, J=6.3), 1.03 (t, 3H, J=7.2), 1.43 (t, 2H, J=7.2), 1.61-1.85 (m, 2H), 2.07 (m, 1H), 2.56-2.74 (m, 2H), 3.07-3.17 (m, 2H), 3.25 (s, 3H), 3.49 (t, 2H, J=4.7), 4.05-4.14 (m, 3H), 4.89 (m, 1H), 7.16-7.36 (m, 5H), 7.34 (d, 1H, J=8.4), 8.33 (d, 1H, J=6.9), 8.65 (t, 1H, J=5.9). MALDI-TOF-MS: C$_{23}$H$_{35}$N$_3$O$_6$ (M+H)$^+$, 450.2604, Actual measurement value, 450.2701.

Production Example 14

((1S)-1-((((1S)-2,3-Dioxo-3-ethylamino-1-(phenylethyl)propyl)amino)carbonyl)-3-methylbutyl)carbamic acid (3S)-tetrahydrofuran-3-yl ester (compound 14)

[Chem. 64]

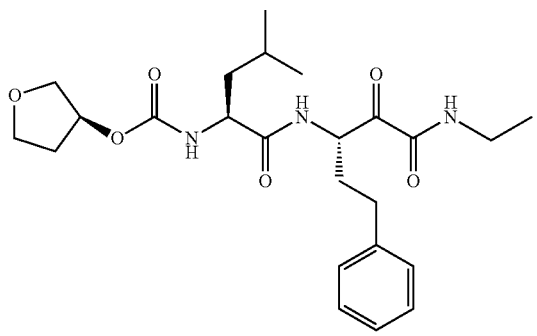

The reaction was performed as in Production Example 1 by using the compound of Reference Example 2 in place of the compound of Reference Example 1, and by using the compound of Reference Example 16 in place of the compound of Reference Example 8, thereby yielding the title compound as a colorless crystal, via ((1S)-1-((((1S)-3-ethylamino-2-hydroxy-3-oxo-1-(phenylethyl)propyl)amino)carbonyl)-3-methylbutyl)carbamic acid (3S)-tetrahydrofuran-3-yl ester.

Melting point: 111.9-114.5° C. $^1$H-NMR (300 MHz, DMSO-d) 50.89 (t, 6H, J=6.3), 1.03 (t, 3H, J=7.2), 1.43 (t, 2H, J=7.4), 1.60-1.91 (m, 3H), 2.09 (m, 2H), 2.56-2.76 (m, 2H), 3.07-3.17 (m, 2H), 3.63-3.82 (m, 4H), 4.02-4.13 (m, 1H), 4.88 (m, 1H), 5.09-5.13 (m, 1H), 7.16-7.31 (m, 5H), 7.34 (d, 1H, J=8.4), 8.34 (d, 1H, J=6.9), 8.66 (t, 1H, J=5.7). MALDI-TOF-MS: C$_{24}$H$_{35}$N$_3$O$_6$ (M+H)$^+$, 462.2604, Actual measurement value, 462.2870.

Production Example 15

((1S)-1-((((1S)-2,3-Dioxo-3-cyclopropylamino-1-(phenylethyl)propyl)amino)carbonyl)-3-methylbutyl) carbamic acid 2-methoxyethyl ester (compound 15)

[Chem. 65]

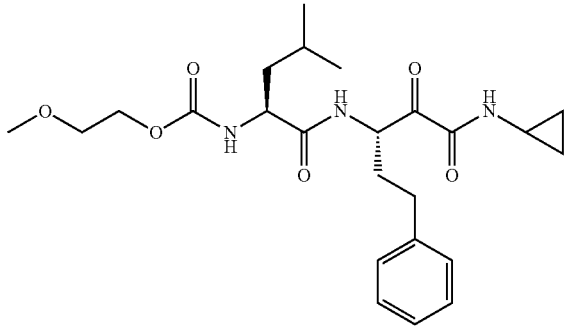

The reaction was performed as in Production Example 1 by using the compound of Reference Example 17 in place of the compound of Reference Example 8, thereby yielding the title compound as a colorless crystal, via ((1S)-1-((((1S)-3-cyclopropylamino-2-hydroxy-3-oxo-1-(phenylethyl)propyl)amino)carbonyl)-3-methylbutyl)carbamic acid 2-methoxyethyl ester.

Melting point: 109.7-111.1° C. $^1$H-NMR (300 MHz, DMSO-d$_6$) δ0.53-0.68 (m, 4H), 0.87-0.91 (m, 6H), 1.43 (t, 3H, J=7.2), 1.59-1.85 (m, 2H), 2.01-2.13 (m, 1H), 2.56-2.74 (m, 3H), 3.25 (s, 3H), 3.48-3.51 (m, 2H), 4.05-4.14 (m, 3H), 4.87 (m, 1H), 7.17-7.36 (m, 6H), 8.34 (d, 1H, J=6.6), 8.69 (d, 1H, J=5.1). MALDI-TOF-MS: C$_{24}$H$_{35}$N$_3$O$_6$ (M+H)$^+$, 462.2604, Actual measurement value, 462.2742.

Production Example 16

((1S)-1-((((1S)-2,3-Dioxo-3-cyclopropylamino))-1-(phenylethyl)propyl)amino)carbonyl)-3-methylbutyl) carbamic acid (3S)-tetrahydrofuran-3-yl ester (compound 16)

[Chem. 66]

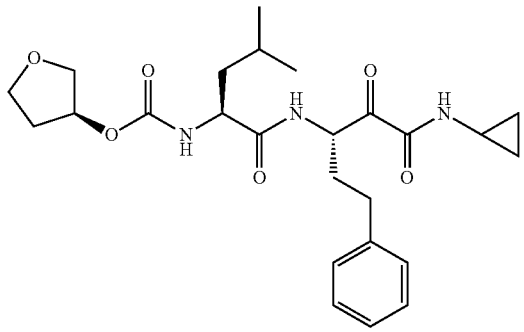

The reaction was performed as in Production Example 1 by using the compound of Reference Example 2 in place of the compound of Reference Example 1, and by using the compound of Reference Example 17 in place of the compound of Reference Example 8, thereby yielding the title compound as a colorless crystal, via ((1S)-1-((((1S)-3-cyclopropylamino-2-hydroxy-3-oxo-1-(phenylethyl)propyl)amino)carbonyl)-3-methylbutyl)carbamic acid (3S)-tetrahydrofuran-3-yl ester.

Melting point: 115.8-116.2° C. $^1$H-NMR (300 MHz, DMSO-d$_6$) δ0.56-0.59 (m, 4H), 0.88 (t, 6H, J=6.3), 1.42 (t, 2H, J=7.4), 1.60-1.91 (m, 3H), 2.09 (m, 2H), 2.56-2.76 (m, 3H), 3.63-3.81 (m, 4H), 4.05-4.13 (m, 1H), 4.87 (m, 1H), 5.09-5.13 (m, 1H), 7.20-7.35 (m, 6H), 8.34 (d, 1H, J=6.9), 8.69 (d, 1H, J=5.1). MALDI-TOF-MS: C$_{25}$H$_{35}$N$_3$O$_6$ (M+H)$^+$, 474.2604, Actual measurement value, 474.2598.

Production Example 17

((1S)-1-((((1S)-1-Benzyl-2,3-dioxo-3-(cyclopropylamino)propyl)amino)carbonyl)-3-methylbutyl)carbamic acid 5-methoxy-3-oxapentyl ester (compound 17)

[Chem. 67]

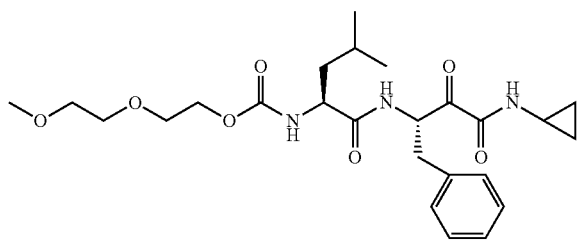

The reaction was performed as in Production Example 1 by using the compound of Reference Example 4 in place of the compound of Reference Example 1, and by using the compound of Reference Example 9 in place of the compound of Reference Example 8, thereby yielding the title compound as a colorless crystal, via ((1S)-1-((((1S)-1-benzyl-3-cyclopropylamino-2-hydroxy-3-oxopropyl)amino)carbonyl)-3-methylbutyl)carbamic acid 5-methoxy-3-oxapentyl ester.

Melting point: 127.9-128.7° C. $^1$H-NMR (300 MHz, DMSO-d$_6$) δ0.54-0.66 (m, 4H), 0.81-0.86 (m, 6H), 1.30-1.42 (m, 2H), 1.57 (m, 1H), 2.73 (m, 1H), 2.82 (dd, 1H, J=14.3, 9.2), 3.11 (dd, 1H, J=13.8, 4.2), 3.24 (s, 3H), 3.42-3.44 (m, 2H), 3.50-3.57 (m, 4H), 3.99-4.04 (m, 3H), 5.17 (m, 1H), 7.22-7.30 (m, 6H), 8.22 (d, 1H, J=6.9), 8.71 (d, 1H, J=4.8). MALDI-TOF-MS: C$_{25}$H$_{37}$N$_3$O$_7$ (M+Na)$^+$, 514.2530, Actual measurement value, 514.2944. [α]$_D^{25}$+13.9° (c0.20, DMSO)

Production Example 18

((1S)-1-((((1S)-1-Benzyl-2,3-dioxo-3-(cyclopropylamino)propyl)amino)carbonyl)-3-methylbutyl)carbamic acid 8-methoxy-3,6-dioxaoctyl ester (compound 18)

[Chem. 68]

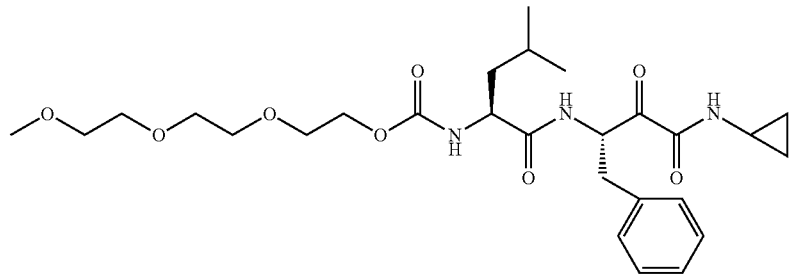

The reaction was performed as in Production Example 1 by using the compound of Reference Example 5 in place of the compound of Reference Example 1, and by using the compound of Reference Example 9 in place of the compound of Reference Example 8, thereby yielding the title compound as a colorless crystal, via ((1S)-1-((((1S)-1-benzyl-3-cyclopropylamino-2-hydroxy-3-oxopropyl)amino)carbonyl)-3-methylbutyl)carbamic acid 8-methoxy-3,6-dioxaoctyl ester.

Melting point: 116.0-117.2° C. $^1$H-NMR (300 MHz, DMSO-d$_6$) δ0.58 (m, 2H), 0.65 (m, 2H), 0.83 (d, 3H, J=7.8), 0.85 (d, 3H, J=6.9), 1.35 (m, 2H), 1.57 (m, 1H), 2.73-2.86 (m, 2H), 3.11 (m, 1H), 3.24 (s, 3H), 3.44 (m, 2H), 3.51 (m, 6H), 3.56 (t, 2H, J=4.7), 4.04 (m, 3H), 5.17 (m, 1H), 7.22-7.31 (m, 6H), 8.25 (d, 1H, J=6.9), 8.73 (d, 1H, J=5.1). MALDI-TOF-MS: C$_{27}$H$_{41}$N$_3$O$_8$ (M+Na)$^+$, 558.2792, Actual measurement value, 558.2717. [α]$_D^{25}$+2.5° (c0.20, DMSO)

Production Example 19

(((1S)-1-((((1S)-1-Benzyl-2,3-dioxo-3-(cyclopropylamino)propyl)amino)carbonyl)-3-methylbutyl)carbamic acid 11-methoxy-3,6,9-trioxaundecanyl ester (compound 19)

[Chem. 69]

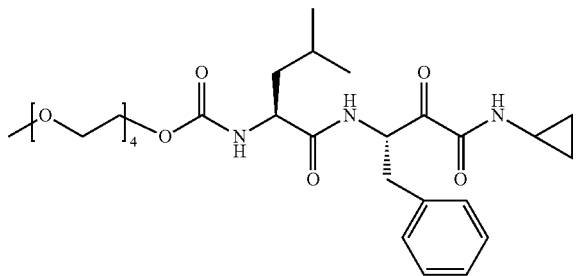

The reaction was performed as in Production Example 1 by using the compound of Reference Example 6 in place of the compound of Reference Example 1, and by using the compound of Reference Example 9 in place of the compound of Reference Example 8, thereby yielding the title compound as a colorless crystal, via ((1S)-1-((((1S)-1-benzyl-3-cyclopropylamino-2-hydroxy-3-oxopropyl)amino)carbonyl)-3-methylbutyl)carbamic acid 11-methoxy-3,6,9-trioxaundecanyl ester.

Melting point: 97.5-98.5° C. $^1$H-NMR (300 MHz, DMSO-$d_6$) δ0.54-0.66 (m, 4H), 0.81-0.86 (m, 6H), 1.32-1.37 (m, 2H), 1.56 (m, 1H), 2.73 (m, 1H), 2.82 (dd, 1H, J=14.0, 9.2), 3.11 (dd, 1H, J=14.1, 4.2), 3.24 (s, 3H), 3.41-3.44 (m, 2H), 3.50-3.51 (m, 10H), 3.54-3.57 (m, 2H), 3.99-4.08 (m, 3H), 5.16 (m, 1H), 7.22-7.31 (m, 6H), 8.25 (d, 1H, J=7.2), 8.73 (d, 1H, J=5.1). MALDI-TOF-MS: $C_{29}H_{45}N_3O_9$ (M+Na)$^+$, 602.3054, Actual measurement value, 602.3427. $[α]_D^{25}$+6.9° (c0.20, DMSO)

Production Example 20

(((1S)-1-((((1S)-1-Benzyl-2,3-dioxo-3-(cyclopropylamino)propyl)amino)carbonyl)-3-methylbutyl)carbamic acid 14-methoxy-3,6,9,12-tetraoxatetradecanyl ester (compound 20)

[Chem. 70]

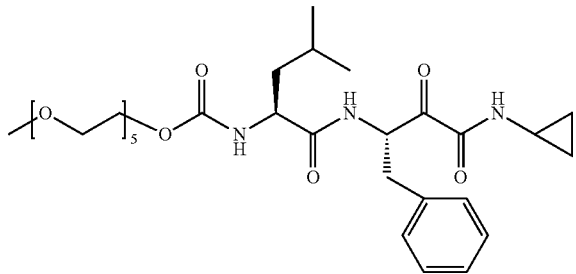

The reaction was performed as in Production Example 1 by using the compound of Reference Example 7 in place of the compound of Reference Example 1, and by using the compound of Reference Example 9 in place of the compound of Reference Example 8, thereby yielding the title compound as a colorless crystal, via ((1S)-1-((((1S)-1-benzyl-3-cyclopropylamino-2-hydroxy-3-oxopropyl)amino)carbonyl)-3-methylbutyl)carbamic acid 14-methoxy-3,6,9,12-tetraoxatetradecanyl ester.

Melting point: 98.5-99.9° C. $^1$H-NMR (300 MHz, DMSO-$d_6$) δ0.58 (m, 2H), 0.65 (m, 2H), 0.83 (d, 3H, J=6.9), 0.85 (d, 3H, J=7.8), 1.35 (m, 2H), 1.57 (m, 1H), 2.73-2.86 (m, 2H), 3.11 (m, 1H), 3.24 (s, 3H), 3.42 (m, 2H), 3.51 (m, 14H), 3.56 (t, 2H, J=3.3), 4.04 (m, 3H), 5.17 (m, 1H), 7.22-7.30 (m, 6H), 8.24 (d, 1H, J=6.9), 8.72 (d, 1H, J=4.5). MALDI-TOF-MS: $C_{31}H_{49}N_3O_{10}$ (M+Na)$^+$, 646.3316, Actual measurement value, 646.3404.

Production Example 21

(((1S)-1-((((1S)-2,3-Dioxo-1-(2-methylpropyl)-3-(2-phenoxyethyl)aminopropyl)amino)carbonyl)-3-methylbutyl)carbamic acid 2-methoxyethyl ester (compound 21)

[Chem. 71]

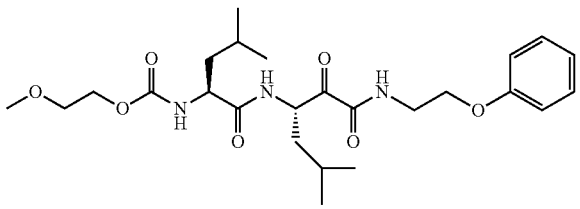

The reaction was performed as in Production Example 1 by using the compound of Reference Example 18 in place of the compound of Reference Example 8, thereby yielding the title compound as a colorless crystal, via ((1S)-1-((((1S)-2-hydroxy-1-(2-methylpropyl)-3-oxo-3-(2-phenoxyethyl)aminopropyl)amino)carbonyl)-3-methylbutyl)carbamic acid 2-methoxyethyl ester.

Melting point: 99.7-100.5° C. $^1$H-NMR (300 MHz, DMSO-$d_6$) δ0.88 (dd, 12H, J=12.0, 6.3), 1.35-1.54 (m, 4H), 1.58-1.75 (m, 2H), 3.25 (s, 3H), 3.46-3.53 (m, 4H), 4.03-4.07 (m, 5H), 5.06 (m, 1H), 6.91-6.95 (m, 3H), 7.26-7.31 (m, 3H), 8.15 (d, 1H, J=7.2), 8.81 (t, 1H, J=5.9). MALDI-TOF-MS: $C_{25}H_{39}N_3O_7$ (M+H)$^+$, 494.2866, Actual measurement value, 494.2967.

Production Example 22

((1S)-1-((((1S)-2,3-Dioxo-1-(2-methylpropyl)-3-(2-phenoxyethyl)aminopropyl)amino)carbonyl)-3-methylbutyl) carbamic acid 5-methoxy-3-oxapentyl ester (compound 22)

[Chem. 72]

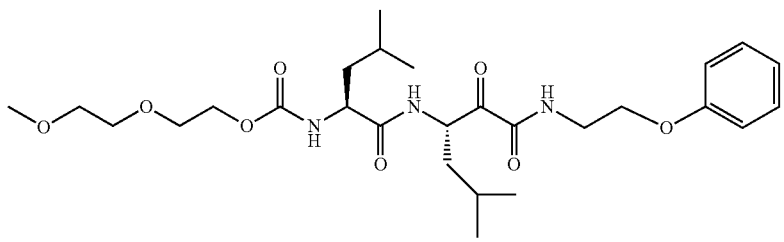

The reaction was performed as in Production Example 1 by using the compound of Reference Example 4 in place of the compound of Reference Example 1, and by using the compound of Reference Example 18 in place of the compound of Reference Example 8, thereby yielding the title compound as a colorless crystal, via ((1S)-1-((((1S)-2-hydroxy-1-(2-methylpropyl)-3-oxo-3-(2-phenoxyethyl)amino-propyl)amino)carbonyl)-3-methylbutyl)carbamic acid 5-methoxy-3-oxapentyl ester.

Melting point: 53.3-54.1° C. $^1$H-NMR (300 MHz, DMSO-$d_6$) δ0.87 (dd, 12H, J=12.2, 6.5), 1.35-1.54 (m, 4H), 1.58-1.75 (m, 2H), 3.24 (s, 3H), 3.41-3.45 (m, 2H), 3.47-3.57 (m, 6H), 4.03-4.07 (m, 5H), 5.06 (m, 1H), 6.91-6.96 (m, 3H), 7.26-7.31 (m, 3H), 8.17 (d, 1H, J=6.9), 8.83 (t, 1H, J=5.7). MALDI-TOF-MS: $C_{27}H_{43}N_3O_8$ (M+H)$^+$, 538.3128, Actual measurement value, 538.3140.

Production Example 23

((1S)-1-((((1RS)-3-Amino-1-benzyl-2,3-dioxopropyl)amino)carbonyl)-3-methylbutyl)carbamic acid 5-methoxy-3-oxapentyl ester (compound 23)

[Chem. 73]

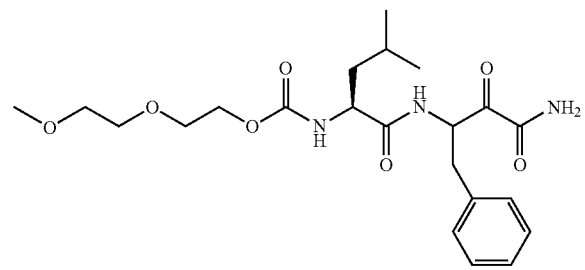

The reaction was performed as in Production Example 1 by using the compound of Reference Example 4 in place of the compound of Reference Example 1, and by using the compound of Reference Example 19 in place of the compound of Reference Example 8, thereby yielding the title compound as a colorless crystal, via ((1S)-1-((((1RS)-3-amino-1-benzyl-2-hydroxy-3-oxopropyl)amino)carbonyl)-3-methylbutyl)carbamic acid 5-methoxy-3-oxapentyl ester.

$^1$H-NMR (300 MHz, DMSO-$d_6$) δ0.77 (d, 3H, J=6.3), 0.83 (d, 1.5H, J=6.6), 0.86 (d, 1.5H, J=6.9), 1.05-1.63 (m, 3H), 2.68-2.85 (m, 1H), 3.12 (m, 1H), 3.23 (s, 3H), 3.42 (m, 2H), 3.51-3.56 (m, 4H), 4.03 (m, 3H), 5.22 (m, 1H), 7.21-7.31 (m, 6H), 7.81 (d, 1H, J=14), 8.06 (d, 1H, J=18), 8.19 (d, 0.5H, J=6.9), 8.26 (d, 0.5H, J=7.5).

Production Example 24

((1S)-1-((((1S)-1-Benzyl-3-(cyclopropylamino)-2,3-dioxopropyl)amino)carbonyl)-3-methylbutyl)carbamic acid 2-(pyridin-2-yl)ethyl ester (compound 24)

[Chem. 74]

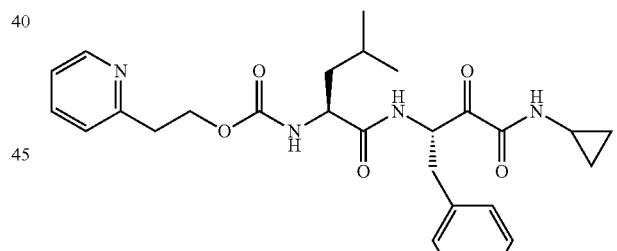

The reaction was performed as in Production Example 1 by using the compound of Reference Example 20 in place of the compound of Reference Example 1, and by using the compound of Reference Example 9 in place of the compound of Reference Example 8, thereby yielding the title compound as a colorless crystal, via (((1S)-1-((((1S)-1-benzyl-3-(cyclopropylamino)-2-hydroxy-3-oxopropyl)amino)carbonyl)-3-methylbutyl)carbamic acid 2-(pyridin-2-yl)ethyl ester.

$^1$H-NMR (300 MHz, DMSO-d) 50.58-0.66 (m, 4H), 0.83 (t, 6H, J=7.1), 1.31-1.35 (m, 2H), 1.53 (m, 1H), 2.74 (m, 1H), 2.81 (dd, 1H, J=14.1, 9.3), 3.02 (t, 2H, J=6.3), 3.11 (dd, 1H, J=14.0, 4.1), 4.01 (m, 1H), 4.28-4.32 (m, 2H), 5.17 (m, 1H), 7.14-7.34 (m, 8H), 7.75 (t, 1H, J=6.8), 8.23 (d, 1H, J=7.2), 8.51 (d, 1H, J=4.2), 8.71 (d, 1H, J=4.5).

Production Example 25

(((1S)-1-(((((1S)-1-Benzyl-3-(cyclopropylamino)-2,3-dioxopropyl)amino)carbonyl)-3-methylbutyl)carbamic acid 2-(6-methylpyridin-2-yl)ethyl ester (compound 25)

[Chem. 75]

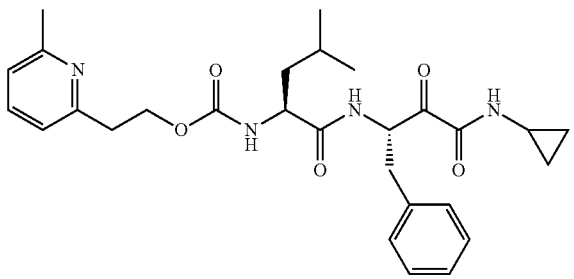

The reaction was performed as in Production Example 1 by using the compound of Reference Example 21 in place of the compound of Reference Example 1, and by using the compound of Reference Example 9 in place of the compound of Reference Example 8, thereby yielding the title compound as a colorless crystal, via (((1S)-1-(((((1S)-1-benzyl-3-(cyclopropylamino)-2-hydroxy-3-oxopropyl)amino)carbonyl)-3-methylbutyl)carbamic acid 2-(6-methylpyridin-2-yl)ethyl ester.

Melting point: 162.0-163.6° C.

$^1$H-NMR (300 MHz, DMSO-$d_6$) δ0.54-0.66 (m, 4H), 0.76-0.86 (m, 6H), 1.54 (m, 1H), 2.43 (s, 3H), 2.73-2.86 (m, 2H), 2.96 (t, 2H, J=6.5), 3.11 (m, 1H), 4.03 (m, 1H), 4.21-4.34 (m, 2H), 5.17 (m, 1H), 7.07-7.30 (m, 8H), 7.58 (t, 1H, J=7.7), 8.23 (d, 1H, J=6.9), 8.72 (d, 1H, J=4.8).

Production Example 26

(((1S)-1-(((((1S)-1-Benzyl-3-(cyclopropylamino)-2,3-dioxopropyl)amino)carbonyl)-3-methylbutyl)carbamic acid 2-(5-ethylpyridin-2-yl)ethyl ester (compound 26)

[Chem. 76]

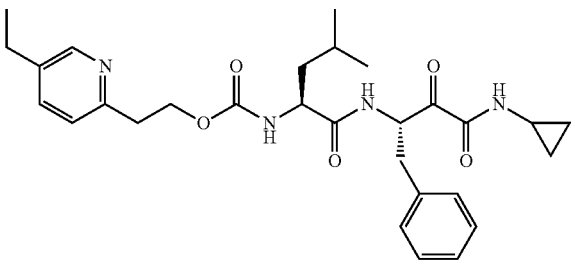

The reaction was performed as in Production Example 1 by using the compound of Reference Example 22 in place of the compound of Reference Example 1, and by using the compound of Reference Example 9 in place of the compound of Reference Example 8, thereby yielding the title compound as a colorless crystal, via (((1S)-1-(((((1S)-1-benzyl-3-(cyclopropylamino)-2-hydroxy-3-oxopropyl)amino)carbonyl)-3-methylbutyl)carbamic acid 2-(5-ethylpyridin-2-yl) ethyl ester.

Melting point: 119.9-121.0° C.

$^1$H-NMR (300 MHz, DMSO-$d_6$) δ0.58-0.66 (m, 4H), 0.75-0.85 (m, 6H), 1.17 (t, 3H, J=7.7), 1.33-1.36 (m, 2H), 1.53 (m, 1H), 2.58 (dd, 2H, J=15.5, 8.3), 2.74-2.85 (m, 2H), 2.94-2.98 (m, 2H), 3.12 (m, 1H), 4.04 (m, 1H), 4.28-4.29 (m, 2H), 5.17 (m, 1H), 7.13-7.26 (m, 7H), 7.55 (d, 1H, J=8.1), 8.22-8.35 (m, 2H), 8.75 (m, 1H).

Production Example 27

(((1S)-1-(((((1S)-1-Benzyl-3-(cyclopropylamino)-2,3-dioxopropyl)amino)carbonyl)-3-methylbutyl)carbamic acid 2-tert-butoxy ethyl ester (compound 27)

[Chem. 77]

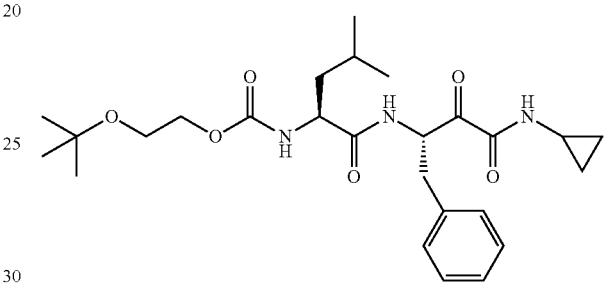

The reaction was performed as in Production Example 1 by using the compound of Reference Example 23 in place of the compound of Reference Example 1, and by using the compound of Reference Example 9 in place of the compound of Reference Example 8, thereby yielding the title compound as a colorless crystal, via (((1S)-1-(((((1S)-1-benzyl-3-(cyclopropylamino)-2-hydroxy-3-oxopropyl)amino)carbonyl)-3-methylbutyl)carbamic acid 2-tert-butoxy ethyl ester.

$^1$H-NMR (300 MHz, DMSO-$d_6$) δ0.58 (m, 2H), 0.65 (m, 2H), 0.83 (d, 3H, J=7.5), 0.85 (d, 3H, J=6.9), 1.12 (s, 9H), 1.35 (m, 2H), 1.57 (m, 1H), 2.74 (m, 1H), 2.82 (m, 1H), 3.11 (m, 1H), 3.45 (m, 2H), 3.98 (m, 3H), 5.17 (m, 1H), 7.24 (m, 6H), 8.23 (d, 1H, J=6.6), 8.71 (d, 1H, J=4.8).

Production Example 28

(((1S)-1-(((((1S)-1-Benzyl-3-(cyclopropylamino)-2,3-dioxopropyl)amino)carbonyl)-3-methylbutyl)carbamic acid 2-isopropoxyethyl ester (compound 28)

[Chem. 78]

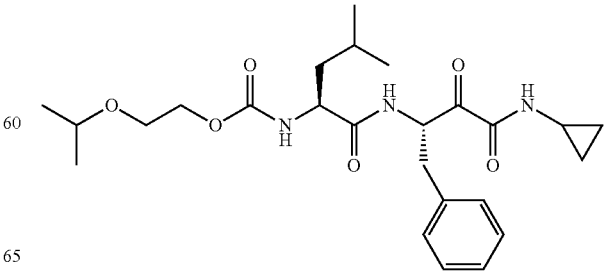

The reaction was performed as in Production Example 1 by using the compound of Reference Example 24 in place of the compound of Reference Example 1, and by using the compound of Reference Example 9 in place of the compound of Reference Example 8, thereby yielding the title compound as a colorless crystal, via (((1S)-1-((((1S)-1-benzyl-3-(cyclopropylamino)-2-hydroxy-3-oxopropyl)amino)carbonyl)-3-methylbutyl)carbamic acid 2-isopropoxyethyl ester.

$^1$H-NMR (300 MHz, DMSO-$d_6$) δ0.58 (m, 2H), 0.65 (m, 2H), 0.83 (d, 3H, J=7.2), 0.85 (d, 3H, J=6.9), 1.07 (d, 6H, J=5.7), 1.35 (m, 2H), 1.57 (m, 1H), 2.74 (m, 1H), 2.82 (m, 1H), 3.12 (m, 1H), 3.50 (m, 2H), 3.55 (m, 1H), 4.01 (m, 3H), 5.17 (m, 1H), 7.24 (m, 6H), 8.22 (d, 1H, J=6.9), 8.71 (d, 1H, J=3.6).

Measurement of Inhibitory Activity Against μ-Calpain and m-Calpain

The inhibitory activity against μ-calpain and m-calpain was assayed according to a published method (Anal. Biochem. 1993, vol. 208, p. 387-392). More specifically, 200 μL of a reaction solution containing 0.5 mg/mL casein, 50 mM Tris-HCl buffer (pH 7.4), 20 mM dithiothreitol and 1.0 nmol μ-calpain (derived from human red blood cells, Cosmo Bio Co., Ltd.) or m-calpain (derived from porcine kidney, Cosmo Bio Co., Ltd.) was added to individual 2.5 μL portions of DMSO solution containing a varying concentration of a test sample in a 96-well plate. Then, 50 μL of 20 mM aqueous calcium chloride was added thereto, and reaction was performed at 30° C. for 60 minutes. 100 μL of the reaction solution was transferred to another 96-well plate, and purified water (50 μL) and 50% aqueous solution (100 μL) of Protein Assay Dye Reagent (available from Bio-Rad Laboratories, Inc.; catalogue No. 500-600) were added thereto. The reaction mixture was allowed to stand at room temperature for 15 minutes, and its absorbance was measured at 595 nM. The absorbance of a reaction mixture prepared in the same manner as mentioned above, except that a DMSO solution containing no sample was used as a control value; and the absorbance of a reaction mixture prepared in the same manner as mentioned above, except that a 1 mM aqueous EDTA solution (50 μL) was used in place of 20 mM aqueous calcium chloride, was used as a blank value. The inhibition rate was calculated according to the following equation, and the concentration required for 50% inhibition ($IC_{50}$) was determined.

Inhibition rate (%){1−(measured value−blank test value)/(control value−blank test value)}×100

The concentrations ($IC_{50}$) are shown in Table 1 as enzyme (calpain) inhibitory activities (μM). The compounds inhibited activities of μ-calpain and m-calpain.

TABLE 1

| | enzyme inhibitory activities (μM) | |
|---|---|---|
| compound | μ-calpain | m-calpain |
| compound 1 | 0.17 | 0.11 |
| compound 2 | 0.15 | 0.11 |
| compound 3 | 0.25 | 0.16 |
| compound 4 | 0.11 | 0.10 |
| compound 5 | 0.09 | 0.05 |
| compound 6 | 0.12 | 0.13 |
| compound 7 | 0.10 | 0.07 |
| compound 8 | 0.17 | 0.08 |
| compound 9 | 0.10 | 0.14 |
| compound 10 | 0.45 | 0.34 |
| compound 11 | 0.17 | 0.12 |

TABLE 1-continued

| | enzyme inhibitory activities (μM) | |
|---|---|---|
| compound | μ-calpain | m-calpain |
| compound 12 | 0.18 | 0.11 |
| compound 13 | 0.30 | 0.20 |
| compound 14 | 0.16 | 0.20 |
| compound 15 | 0.18 | 0.14 |
| compound 16 | 0.14 | 0.10 |
| compound 17 | 0.17 | 0.10 |
| compound 18 | 0.19 | 0.12 |
| compound 19 | 0.22 | 0.17 |
| compound 20 | 0.42 | 0.19 |
| compound 21 | 0.08 | 0.11 |
| compound 22 | 0.09 | 0.16 |
| compound 23 | 0.19 | 0.18 |
| compound 24 | 0.029 | 0.017 |

Among these compounds, Compound 17 was used for the following analysis. Compound 17 is SNJ-1945. Hereunder, Compound 17 is also referred to as SNJ-1945.

The test animals and test cells used in the analysis below were prepared basically in the same manner as in the aforementioned Non-Patent Document 1 (Masami Yamada et al., Nature Medicine 15, 1202-1207 (2009)). In experiments in which test animals are killed, the test animals were anesthetized using a fatal dose of ether, and euthanized. The experiments below occasionally perform staining using DAPI, which is a well-known fluorescence pigment for nucleus staining.

Preparation of LIS1 Gene Hetero-Deficient Mice (LIS1 Heterozygous Mice)

LIS1 heterozygous mice were prepared as follows. 129S-Pafah1b1$^{tm2Awb}$/J (The Jackson Laboratory) was used as a LIS1 conditional knockout mouse. The mouse has a system for deactivating LIS1 by the insertion of loxP sequence into intron II and intron V; thus, exon III to exon VI are deleted by the Cre-loxP system. 129S-Pafah1b1$^{tm2Awb}$/J female mice were mated with homozygous EII-Cre transgenic male mice (FVB/N-Tg (EIIa-cre) C5379Lmgd/J, The Jackson Laboratory). The neo gene used for the selection of ES cells of 129S-Pafah1b1$^{tm2Awb}$/J (The Jackson Laboratory) was removed by partial reaction of Cre protein. The 129S-Pafah1b1$^{tm2Awb}$/J mice lacking the neo gene were mated with each other, thereby obtaining 129S-Pafah1b1$^{tm2Awb}$/J homozygous mice. The neo(−)129S-Pafah1b1$^{tm2Awb}$/J male homozygous mice were mated with female FVB/N-Tg (EIIa-cre) C5379Lmgd/J mice (The Jackson Laboratory), thereby obtaining LIS1 heterozygous mice.

FVB/NJcl mice purchased from CLEA Japan, Inc. were used as the wild-type mice.

Analysis of Change in LIS1 Protein Amount in Cells by SNJ-1945

Fibroblasts (MEF; mouse embryonic fibroblasts) were established from five each of LIS1 gene hetero-deficient and wild-type mice (12.5- to 14.5-day-old embryos). The fibroblasts were established as follows. Pregnant mice were killed by cervical fracture, and the mouse embryos were immediately isolated under a germ-free condition. After the heads and visceral tissues were removed with tweezers, the mouse embryos were dissected with scissors. 10 ml of Trypsin-EDTA (Gibco, 25200) was added to each dissected tissue fraction, and the resulting liquid was placed in a 50 ml plastic tube (Nunc, 373687) to be subjected to 30-minute incubation at 37° C. After incubation, 10 ml of fetal bovine serum (Equitech-Bio, Inc., SFBM30-1798) was added, followed by pipetting with a 10 ml pipette (Nunc, 159633), thereby isolating the cells. After the cells were allowed to stand at room temperature for 5 minutes, the supernatant was collected. The supernatant was then transferred to a 50 ml plastic tube (Nunc, 373687) to be subjected to centrifugation for 5 minutes at 1000 RPM, after which the supernatant was discarded. Thereafter, the cell pellet was cultured in a cell culture solution containing D-MEM (Wako, 041-29775), fetal bovine serum (Equitech-Bio, Inc., SFBM30-1798) in an amount corresponding to 10%, L-glutamine (Gibco, 25030) in an amount corresponding to 1%, and Pen-Strep (Gibco, 15140) in a 10 cm cell culture petri dish (Greiner Bio-One, 664160). The 10 cm cell culture petri dish (Greiner Bio-One, 664160) was washed with PBS every 3 days. Then, 1 ml of Trypsin-EDTA (Gibco, 25200) was added to the cell culture petri dish for incubation at 37'C for 5 minutes; afterward, the cells were isolated. A cell culture solution (9 ml) containing D-MEM (Wako, 041-29775), fetal bovine serum (Equitech-Bio, Inc., SFBM30-1798) in an amount corresponding to 10%, L-glutamine (Gibco, 25030) in an amount corresponding to 1%, and Pen-Strep (Gibco, 15140) was added to the cells, followed by pipetting with a 10 ml pipette (NUNC, 159633). 2 ml portions of the resulting cell liquid were added to five 10 cm cell culture petri dishes (Greiner Bio-One, 664160). Further, a cell culture solution (8 ml) containing D-MEM (Wako, 041-29775), fetal bovine serum (Equitech-Bio, Inc., SFBM30-1798) in an amount corresponding to 10%, L-glutamine (Gibco, 25030) in an amount corresponding to 1%, and Pen-Strep (Gibco, 15140) was added to each cell culture petri dish to obtain a 10 ml cell culture solution, which was cultured at 37° C. under 5% $CO_2$ using cell culture equipment.

Using the cells, the influence of SNJ-1945 on the LIS protein amount in each cell was analyzed as follows. More specifically, the analysis was performed using western blotting in the following manner. The fibroblasts prepared above were subjected to extraction using a protein extraction buffer (20 mM Tris-HCl, pH 7.5, 100 mM NaCl, 5 mM EDTA, 0.1% Triton X-100). After determination of protein quantity, 10 μg of protein was placed on each lane. After isolation using a 10% acrylic gel (SDS-PAGE), the protein was transferred to an Immobilon membrane (Millipore, IPVH00010), and LIS and DIC (dynein intermediate chain: reflecting the dynein amount) were detected. 3-actin was detected to be used as a protein amount reference. The following antibodies were used in the western blotting: anti-LIS1 antibody (N-19,SC-17577, goat polyclonal antibody, Santa Cruz Biotechnology; diluted to 1:100), anti-cytoplasmic dynein intermediate chain antibody (74.1, mouse monoclonal antibody, Millipore; diluted to 1:100), anti-PCOP antibody (mouse monoclonal antibody, Sigma; diluted to 1:100), and anti-β-actin antibody (SC-17210, rabbit polyclonal antibody, Santa Cruz Biotechnology; diluted to 1:100).

FIG. 1 shows the results. FIG. 1(a) shows the detected bands, and the graph in FIG. 1(b) shows the intensities of the bands. The results reveal that the LIS protein amount was significantly decreased in Lis1$^{+/-}$ cells, whereas the decrease in the LIS protein amount was recovered in Lis1$^{+/-}$ cells treated with SNJ-1945. The results demonstrated that lissencephaly is treatable by SNJ-1945.

Analysis of Change in Intracellular Protein Localization by SNJ-1945

A LIS1 gene hetero-deficient mice group and a wild-type mice (12.5- to 14.5-day-old embryos) group each consisting of five mice were prepared, and fibroblasts (MEF; mouse embryonic fibroblast) were established from each group in the same manner as above (more specifically, fibroblasts were established by grouping the same gene type). Using the cells, immunocytochemistry was performed as follows. The influence of SNJ-1945 on intracellular protein localization in each cell was analyzed. First, a slide glass (24×24 mm; Matsunami Glass Ind., Ltd.) washed beforehand with 0.1 N hydrochloric acid was placed on a 6-well plate (Nunc), and MEF cells were seeded in an amount of 1.0×10$^5$ cells per well in a D-MEM culture solution (containing 10% fetal bovine blood serum; Wako Pure Chemical Ind. Ltd.). Subsequently, the 6-well plate was cultured overnight at 37° C. under 5% $CO_2$, and SNJ-1945 was added thereto so that the final concentration became 200 μM. The incubation was performed for another 2 hours under the same conditions.

As a control experiment, the same experiment was performed by adding 1% dimethylsulfoxide (DMSO). After washing with phosphate buffer (PBS), the MEF cells were immobilized using 4% paraformaldehyde (Wako, 162-16065) (at room temperature, for 15 minutes). The MEF cells were treated with 0.2% Triton X-100 (at room temperature, for 10 minutes), and then were blocked for an hour at room temperature using 5% bovine blood serum albumin (Wako Pure Chemical Ind., Ltd.)/Block Ace (Yukijirusi Nyugyo, Japan). As the primary antibody, anti-LIS1 antibody (N-19, SC-7577, goat polyclonal antibody, Santa Cruz Biotechnology; diluted to 1:100), anti-cytoplasmic dynein intermediate chain antibody (74.1, mouse monoclonal antibody, Millipore diluted to 1:100), and anti-(COP antibody (mouse monoclonal antibody, Sigma; diluted to 1:100) were separately diluted with a blocking solution, and reaction was performed for an hour at room temperature. After the reaction, the MEF cells were washed with a phosphate buffer (PBS), and the reaction was performed at room temperature for an hour using Alexa 546 anti-mouse IgG (Invitrogen) or Alexa 546 anti-goat IgG (Invitrogen) as the secondary antibody, which was diluted with phosphate buffer (PBS) to 1:2000. Then, for nuclear staining, DAPI (4',6-diamino-2-phenylindole; Invitrogen, D1306) was added so that the final concentration became 0.2 μM. Incubation was performed for another 15 minutes at room temperature. After incubation, the cells were washed well with PBS, and embedded using glycerol (Merck) for fluorescence microscope observation.

Further, to obtain positional information in the site where the minus ends of microtubules are clustered, γ tubulin, a marker of centrosome, is also subjected to immunostaining in the same manner. As anti-γ tubulin antibody, Santa Cruz mouse monoclonal antibody (diluted to 1:100) was used. As the secondary antibody, fluorescently-labeled Invitrogen Alexa 488 anti-mouse IgG (diluted to 1:1000) was used.

After careful observation using a confocal laser microscope (TCS-SP5, Leica), the intracellular locations of the individual factors in MEF cells under varying conditions are classified into "cells clustered around the nucleus" and "cells distributed to the entire cytoplasm." For each cell group, 10 samples, each of which consists of 10 arbitrarily extracted cells, i.e., 100 cells in total for each group, were evaluated, and the average value±standard deviation was calculated. By means of Student's t-test (unpaired), a significance test was conducted. FIGS. 2 to 4 show the results. In FIG. 4, the abbreviated codes indicate the following: N.S.: no significant difference, *:P<0.05, :P<0.01, and *:P<0.001.

Figure 2A:
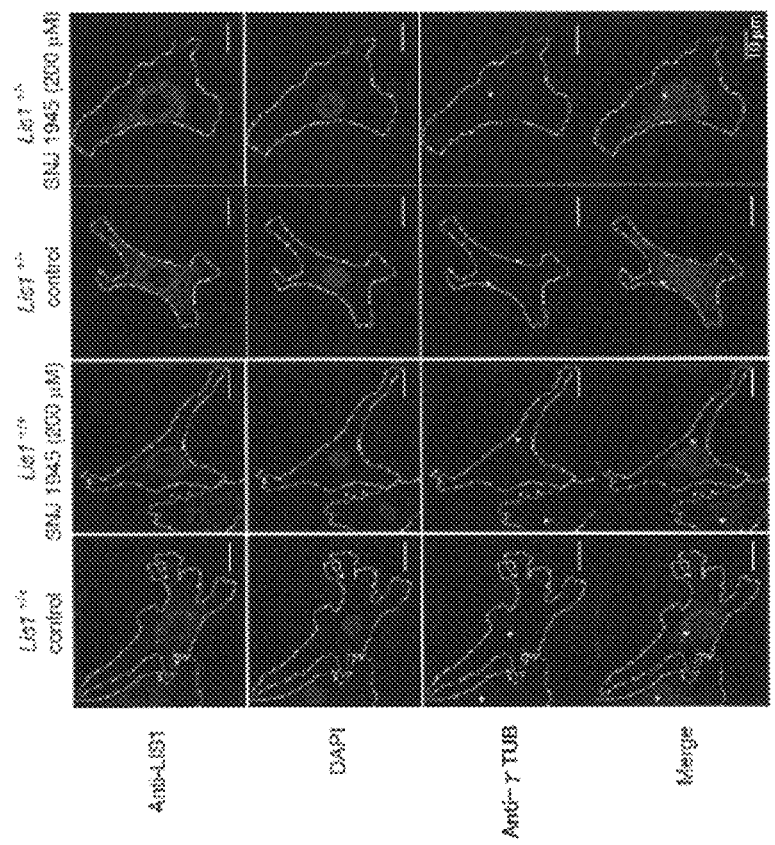
Figures 3A, 3B:
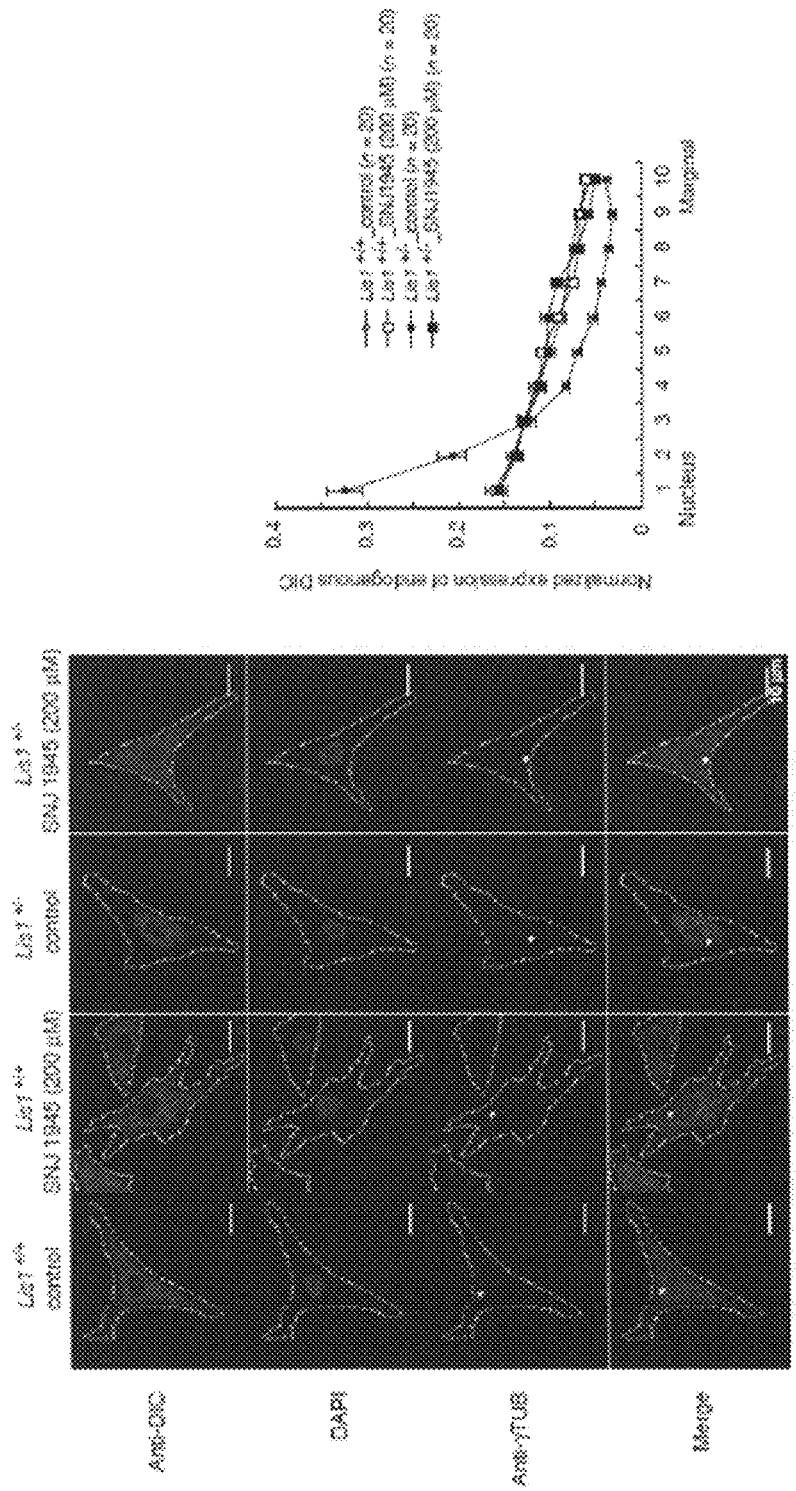
FIGS. 3A-3B show the results of analysis of the influence of SNJ-1945 on intracellular cytoplasmic dynein localization. The results reveal that cytoplasmic dynein localization was recovered by SNJ-1945 administration.
Figure 4A:
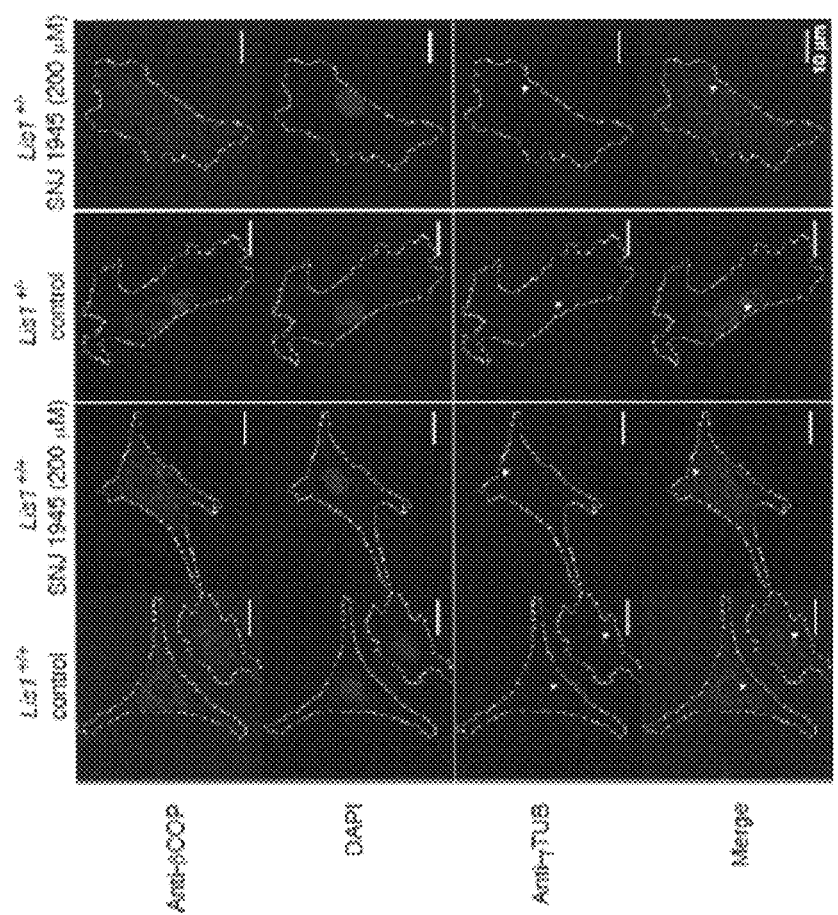
FIGS. 4A-4B show the results of analysis of the influence of SNJ-1945 on intracellular cytoplasmic β-COP localization. The results reveal that cytoplasmic β-COP localization was recovered by SNJ-1945 administration.
Figure 4B:
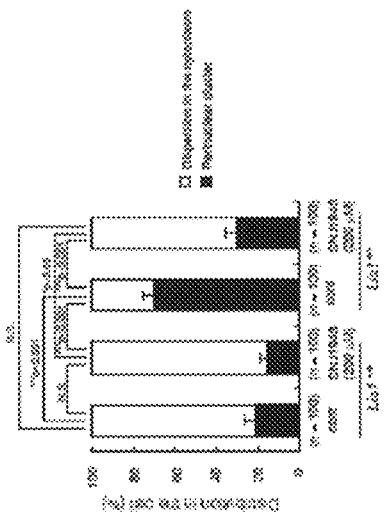

FIGS. 2b, 3b, and 4b are graphs showing quantified values of measured fluorescence intensities in multiple regions obtained by radially dividing the cells from the nucleus marginal zone to the cell marginal zone (more specifically, each fluorescence intensity is measured at 10 points at the same linear interval from the nucleus marginal zone to the cell marginal zone). Since the fluorescence intensities indicate certain protein amounts, the graph denotes the protein amounts in the regions. The amount of LIS1 is supposed to be localized predominantly to the centrosome; however, the LIS1 amount of the fibroblasts established from LIS1 heterozygous mice decreases even around the centrosome. However, it is shown that the LIS1 amount can be recovered by SNJ-1945 (FIG. 2).

Further, although cytoplasmatic dynein is supposed to form a gentle slope and peaks at around the centrosome, cytoplasmatic dynein of the fibroblasts established from LIS1 heterozygous mice is rapidly reduced after the peak near the centrosome, and is depleted around the cell, compared with the normal case. However, it is shown that the cytoplasmatic dynein amount can also be recovered by SNJ-1945 (FIG. 3).

β-COP is one of the markers for Golgi apparatus (localized around the centrosome in fibroblasts), and is generally used as an index of the function of cytoplasmatic dynein. In normal cases, β-COP is highly dense at the centrosome, and is steadily distributed in the cell marginal zone. In the fibroblasts established from LIS1 heterozygous mice, similarly to cytoplasmatic dynein, the β-COP distribution is eccentrically localized in the cell center (FIG. 4). This abnormal distribution reflects the eccentric distribution of cytoplasmatic dynein. The graph shows that the distribution is normalized as the cytoplasmatic dynein localization is normalized by the administration of SNJ-1945 (FIG. 4).

Analysis of Changes in Migration Capability of Cerebellar Granule Nerve Cell by SNJ-1945

Cerebellum tissue fragments of LIS1 gene hetero-deficient and wild-type mice (3-7 days after birth) (10 mice for each group) were crushed by gentle pipetting, and treated with 0.025% trypsin (Gibco, 25200)/0.0013% DNaseI (Sigma, DN-25) at 37° C. for 20 minutes. After centrifugation, a BME culture solution (Gibco, 21010) containing 10% equine blood serum was added for washing, and the reaction was stopped. Thereafter, the reaction liquid was subjected to pipetting by adding a BME culture solution containing 0.0052% DNaseI/10% equine blood serum, and filtered with a cell mesh-strainer (diameter=70 μm; Becton Dickinson). The cells were seeded on an untreated 24-well plate, and pre-incubated for 30 minutes at 37° C. under 5% $CO_2$. The cells were further incubated in a BME culture solution free of DNaseI, but containing 10% equine blood serum, for 8-12 hours in the same manner, thereby forming aggregates of cerebellar granule cells. Thereafter, a cover glass (24×24 mm; Matsunami Glass Ind., Ltd.) treated with poly-L-lysine (Sigma, P4707) and laminin (Sigma, L4544) was placed on a 6-well plate (Nunc), and the aggregates of cerebellar granule nerve cells were placed in a BME culture solution containing a nutritional supplement (N-2 supplement; Gibco, 17502048). SNJ-1945 was added thereto so that the final concentration became 200 μM. The aggregates were incubated for 18-24 hours at 37° C. under 5% $CO_2$.

As a control example, the same experiment was performed by adding 1% dimethylsulfoxide (DMSO; Sigma, D8779).

After the incubation, the aggregates were washed with a phosphate buffer (PBS), and immobilized by 4% paraformaldehyde (Wako, 162-16065) (at room temperature, for 15 minutes). Subsequently, the aggregates were treated with 0.2% Triton X-100 (at room temperature, for 10 minutes). DAPI (4',6-diamino-2-phenylindole; Invitrogen, D1306) was added thereto for nuclear staining so that the final concentration became 0.2 μM, followed by further incubation for 15 minutes at room temperature. Thereafter, the aggregates were repeatedly washed well with PBS, and carefully embedded using glycerol (Merck) for fluorescence microscope observation so as to avoid damage.

After careful observation using a confocal laser microscope (TCS-SP5, Leica), the migratory distance (μm) of the nerve cells from the marginal zone of the cerebellum granule cell aggregates was measured for each cell group. 10 to 210 μm is divided by 20 μm, and the number of cells distributed in each migratory distance range was found as a percentage relative to the total cells. Further, an average migratory distance (μm) was calculated and expressed as average migratory distance (μm)±standard deviation. A significance test was conducted by way of Student's t-test (unpaired). FIG. 5 shows the results.

As shown in FIG. 5, in contrast to $Lis1^{+/-}$ nerve cells, which hardly showed migration, the recovery of migration capability was observed in the SNJ-1945-treated $Lis1^{+/-}$ nerve cells. The results demonstrated that lissencephaly is treatable by SNJ-1945.

Analysis of Change in LIS1 Protein in Mouse Embryo Brains by SNJ-1945 Intraperitoneal Administration A neo(−)129S-Pafah1b1$^{tm2Awb}$/J homozygous male mouse lacking neo gene was mated with five homozygous EII-Cre transgenic female mice (FVB/N-Tg (EIIa-cre) C5379Lmgd/J, The Jackson Laboratory) by raising them in the same mouse cage. In total, six sets of mouse cages were prepared for the mating experiment. The neo(−)129S-Pafah1b1$^{tm2Awb}$/J homozygous mouse were prepared in the same manner as above. Plug check (confirmation of mating) was carried out every morning between 7 and 10 am, thereby determining the gestation cycle. SNJ-1945 was dissolved in dimethyl sulfoxide (DMSO; Sigma, D8779) at a concentration of 100 mg/ml, and intraperitoneally injected to the pregnant mice so that the administration amount became 100 μg per gram of body weight upon Day 12 of embryo period (E12) (intraperitoneal administration). To determine the effect of SNJ-1945 administration, LIS1 proteins of normal mouse embryos and those of LIS1 heterozygous mouse embryos (administered with SNJ-1945) were measured. In the SNJ-1945 administration group, the brain tissues were taken at 0 hour (immediately after the administration), 1 hour, 2 hours, 4 hours, 8 hours, 12 hours, 16 hours, 24 hours, 48 hours, and 72 hours after the administration to measure LIS1 protein, so as to determine the effect of SNJ-1945 over time. Six mice for each group were used for the measurement of LIS1 protein (n=6).

Pregnant mice were killed by cervical fracture, and the mouse embryos were immediately isolated to obtain the brain tissues. For the measurement of LIS1 protein amount, the brain weights were immediately measured as soon as the brains were removed. Then, the brains were completely solubilized by adding a protein-dissolving liquid (30 mM Tris-HCl, pH 6.8, 1.5% sodium dodecyl sulfate (SDS), 0.3% bromophenol blue (BPB; Sigma, B5525-10G), 0.3% 2-mercapto-ethanol (2-ME, Wako, 135-07522), and 15% glycerol) in an amount twice the mouse brain weight, followed by ultrasonic treatment. After the heat treatment for 5 minutes at 95° C., 1 μl of brain-tissue-derived protein solution was isolated by 12.5% SDS-acrylamide electrophoresis, and subjected to western blotting using anti-LIS1 antibody (N-19, SC-17577, goat polyclonal antibody, Santa Cruz Biotechnology; diluted to 1:100).

FIG. 6 shows the results. Although the LIS1 protein amounts of LIS1 heterozygous mouse embryos were about half those of normal mouse embryos, the amounts were recovered to a substantially normal level by SNJ-1945 administration. It was also found that the effect of SNJ-1945 continued for at least three days by a single dose of SNJ-1945. The results demonstrated that lissencephaly is treatable by SNJ-1945.

Analysis of Change in LIS1 Protein in Newborn Mouse Brains by SNJ-1945 Oral Administration A neo(−)129S-Pafah1b1$^{tm24wb}$/J homozygous male mouse lacking neo gene was mated with five homozygous EII-Cre transgenic female mice (FVB/N-Tg (EIIa-cre) C5379Lmgd/J, The Jackson Laboratory) by raising them in the same mouse cage. In total, six sets of mouse cages were prepared for the mating experiment. A newborn was defined at the time of delivery confirmation, which was conducted every morning. SNJ-1945 was dissolved in dimethyl sulfoxide (DMSO) at a concentration of 100 mg/ml, and orally administered using pipettes to the newborn mice in an amount of 200 μg/per gram of body weight.

To determine the effect of SNJ-1945 administration, LIS1 proteins of normal newborn mice and LIS1 heterozygous newborn mice (administered with SNJ-1945) were measured. In the SNJ-1945 administration group, the brain tissues were taken at 0 hour (immediately after the administration), 1 hour, 2 hours, 4 hours, 8 hours, 12 hours, 16 hours, 24 hours, 48 hours, and 72 hours after the administration to measure LIS1 protein, so as to determine the effect of SNJ-1945 over time. Six mice for each group were used for the measurement of LIS1 protein (n=6).

The newborn mice were killed by cutting off their heads, and the brain tissues thereof were immediately isolated. For the measurement of LIS1 protein amount, the weight of the brains was immediately measured as soon as the brains were removed. The brains were completely solubilized by adding a protein-dissolving liquid (30 mM Tris-HCl pH 6.8, 1.5% sodium dodecyl sulfate (SDS), 0.3% bromophenol blue (BPB), 0.3% 2-mercapto-ethanol (2-ME), and 15% glycerol) in an amount twice that of the weight of the mouse brain, followed by ultrasonic treatment. After heat treatment for 5 minutes at 95° C., 1 μl of brain-tissue-derived protein solution was isolated by 12.5% SDS-acrylamide electrophoresis, and subjected to western blotting using anti-LIS1 antibody (N-19, SC-7577, goat polyclonal antibody, Santa Cruz Biotechnology; diluted to 1:100).

FIG. 7 shows the results. Although the LIS1 protein amounts of LIS1 heterozygous newborn mice were about half of those of normal newborn mice, the amounts were recovered to substantially the normal level by SNJ-1945 administration. It was also found that the effect of SNJ-1945 continued for at least three days by a single dose of SNJ-1945.

The results showed that lissencephaly is treatable by oral administration of SNJ-1945, even during the postnatal period.

Analysis of Change in LIS1 Protein in Adult Mouse Brains by SNJ-1945 Intraperitoneal Administration SNJ-1945 was dissolved in dimethyl sulfoxide (DMSO) at a concentration of 100 mg/ml, and intraperitoneally injected to LIS1 heterozygous mice so that the administration amount was 100 μg/per gram of body weight at the time of three weeks after birth. To determine the effect of SNJ-1945 administration, LIS1 proteins of normal adult mice and LIS1 heterozygous adult mice (administered with SNJ-1945) were measured. In the SNJ-1945 administration group, the brain tissues were taken at 0 hour (immediately after the administration), 1 hour, 2 hours, 4 hours, 8 hours, 12 hours, 16 hours, 24 hours, 48 hours, and 72 hours after the administration to measure LIS1 protein, so as to determine the effect of SNJ-1945 over time. Six mice for each group were used for the measurement of LIS1 protein (n=6).

The adult mice were killed by cervical fracture, and the brain tissues were immediately isolated. For the measurement of LIS1 protein amount, the weight of the brains was immediately measured as soon as the brains were removed. The brains were completely solubilized by adding a protein-dissolving liquid (30 mM Tris-HCl, pH 6.8, 1.5% sodium dodecyl sulfate (SDS), 0.3% bromophenol blue (BPB), 0.3% 2-mercapto-ethanol (2-ME), and 15% glycerol) in an amount twice that of the weight of the mouse brain, followed by ultrasonic treatment. After 5-minute heat treatment at 95° C., 1 μl of brain tissue-derived protein solution was isolated by 12.5% SDS-acrylamide electrophoresis, and subjected to western blotting using anti-LIS1 antibody (N-19, SC-7577, goat polyclonal antibody, Santa Cruz Biotechnology; diluted to 1:100).

Figure 8A:
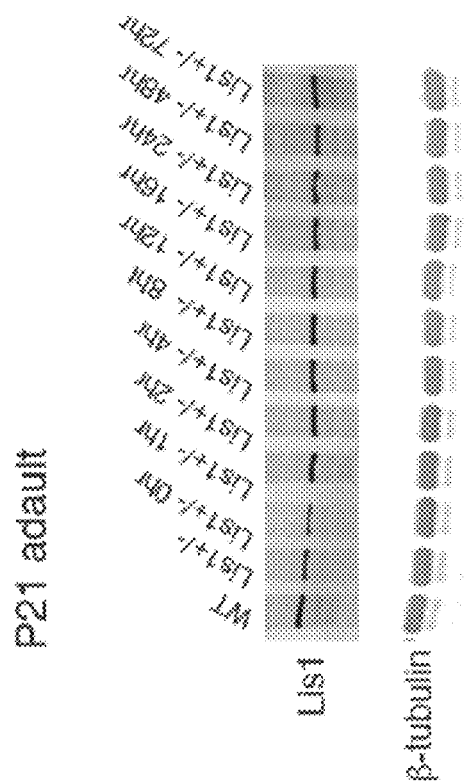
FIGS. 8A-8B show the results of analysis of the influence of SNJ-1945 on LIS protein amount in the brain of an adult mouse (100 μg/g:IP, 3 weeks old, n=6).
Figure 8B:
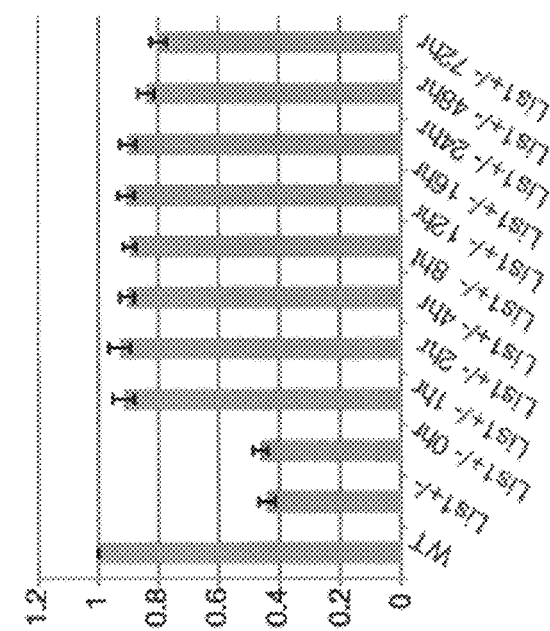

FIG. 8 shows the results. Although the LIS1 protein amounts of LIS1 heterozygous adult mice were about half those of normal adult mice, the amounts were recovered to substantially the normal level by SNJ-1945 administration. It was also found that the effect of SNJ-1945 continued for at least three days by a single dose of SNJ-1945.

The results demonstrated that lissencephaly is treatable by administration of SNJ-1945, even during the postnatal period.

Analysis of Influence of SNJ-1945 Intraperitoneal Administration on Apoptosis in Mouse Embryo Brains A neo(−)129S-Pafah1b1$^{tm24wb}$/J homozygous male mouse lacking neo gene was mated with five homozygous EII-Cre transgenic female mice (FVB/N-Tg (EIIa-cre) C5379Lmgd/J, The Jackson Laboratory) by raising them in the same mouse cage. In total, six sets of mouse cages were prepared for the mating experiment. Plug check (confirmation of mating) was carried out every morning between 7 and 10 am, thereby determining the gestation cycle. SNJ-1945 was dissolved in dimethyl sulfoxide (DMSO) at a concentration of 100 mg/ml, and intraperitoneally injected to the pregnant mice carrying LIS1 heterozygous mice (Lis1$^{+/−}$) and the pregnant mice carrying control mice (normal mouse embryos), so that the administration amount became 100 μg per gram of body weight on alternate days from Day 9.5 of the embryonic period (E9.5). On Day 15.5 of the embryonic period (E15.5), the pregnant mice were killed by cervical fracture, and the mouse embryos were removed and immobilized for 24 hours by 4% paraformaldehyde (Wako: 162-16065). After substitution with PBS, paraffin embedding was performed by a standard method. The tissue block was cut into 5 μm pieces. Each piece was adhered to an APS-coated slide glass. After deparaffinization, 20 μg/ml proteinase K/PBS treatment was conducted for 15 minutes at room temperature, and 3% $H_2O_2$/PBS treatment was performed for ten minutes at room temperature. TUNEL (TdT-mediated dUTP nick-end labeling) staining was performed using an ApopTag Apoptosis Detection Kit (Millipore: S7100) to detect apoptosis. TUNEL staining is known as a method that enables detection of apoptosis by detecting DNA fragments.

Figure 9A:
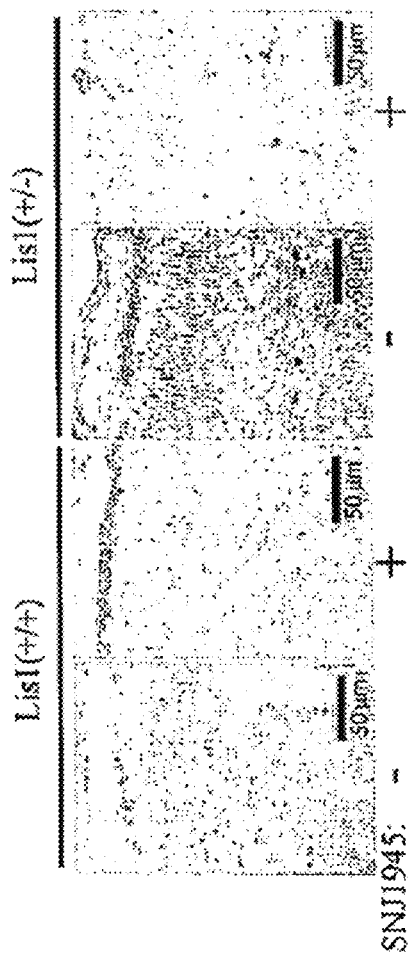
FIGS. 9A-9B show the results of analysis of the influence of SNJ-1945 on apoptosis in the brain of a mouse embryo.
Figure 9B:
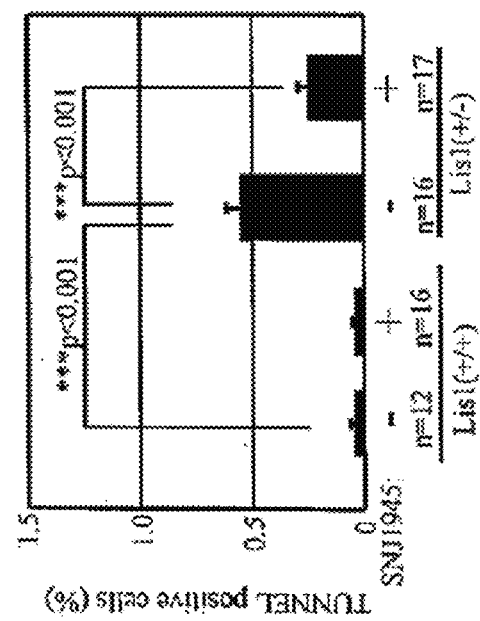

FIG. 9 shows the results. Although apoptosis was hardly observed in normal mice, apoptosis was very frequently observed in LIS1 heterozygous mice. It was also found that apoptosis in LIS1 heterozygous mice is significantly reduced by administration of SNJ-1945. Accordingly, it was assumed that the symptoms of lissencephaly can be alleviated by administration of SNJ-1945.

Analysis of Behavior of Lissencephaly Model Mice (LIS1 Gene Hetero-Deficient Mice)

Lissencephaly patients suffer from significant motor deterioration. Therefore, in order to confirm the lissencephaly-treating effect, the following experiment was conducted based on the motor function of lissencephaly model mice.

Preparation of Mice for Behavior Analysis Experiment

To conduct a behavior analysis experiment, wild-type mice and Lis1 ($^{+/-}$) heterozygous mice were divided into five groups (C group, M1 group, M2 group, M3 group, and M4 group). The details regarding the mice in each group are described below. CE-2 (CLEA Japan, Inc.) was used as mice feed. The wild-type mice and heterozygous mice used for this experiment were prepared in the same method as described in the above section "Preparation of LIS1 gene hetero-deficient mice (LIS1 heterozygous mice)."

C group: control group of wild-type mice

M1 group: LIS1 heterozygous mice without SNJ-1945 administration

M2 group: LIS1 heterozygous mice prepared as follows. SNJ-1945 was dissolved in dimethyl sulfoxide (Sigma, D-5879) at a concentration of 100 mg/ml, and administered to pregnant mice from Day 9.5 of the embryonic period (E9.5) in an amount of 200 μg per gram of maternal body weight per day. The administration was performed by adding SNJ-1945 to mice feed. During the postnatal period, the administration was continued in the same manner as in M3 group below.

M3 group: LIS1 heterozygous mice prepared as follows. SNJ-1945 was dissolved in 0.5% CMC (carboxymethyl cellulose sodium salt: Wako Pure Chemical Industries, Ltd., 039-01335) at a concentration of 50 mg/ml, and administered to newborn mice immediately on the day of birth in an amount of 200 μg per gram of body weight per day through compulsive oral administration. Further, from Day 21 of the postnatal period, administration was performed by adding SNJ-1945 to mice feed so that the administration amount became 200 μg per gram of body weight per day.

M4 group: LIS1 heterozygous mice prepared as follows. SNJ-1945 was dissolved in 0.5% CMC (carboxymethyl cellulose sodium salt) at a concentration of 50 mg/ml, and administered to newborn mice on Day 10 of the postnatal period in an administration amount of 200 μg per gram of body weight per day through compulsive oral administration. Further, from Day 21 of the postnatal period, administration was performed by adding SNJ-1945 to mice feed so that the administration amount became 200 μg per gram of body weight per day.

By adding SNJ-1945 to the mice feed (CE-2, CLEA Japan, Inc.), SNJ-1945 was continuously administered to the mice so that the administration amount became 200 μg per gram of body weight per day through oral administration. For a behavior analysis experiment, 12 to 16 mice were grouped to be subjected to preliminary breeding in the behavior experiment facility for 1 to 2 weeks; thereafter, the behavior of the mice was analyzed at an age of about 9 to 12 weeks. After the behavior analysis experiment, a gene type was determined for all mice.

To certify that the results of the behavior analysis are due to the difference between the groups, the test mice were examined for the following factors (i) to (iv) before the behavior analysis.

(i) Health Check

Rectal temperatures and body weights of the test mice were measured to confirm that there were no abnormalities regarding rectal temperature, body weight, etc. Further, whisker conditions (mice with short or no whiskers) and skin hair conditions (loss of skin hair, tidiness of skin hair) were examined. All test mice were found to be normal.

(ii) Neurological Abnormality Check

Neurological abnormality was examined in terms of the following criteria.

Righting Reflex (ability to return when turned over)

Whisker-Twitch (whether there is any reaction (e.g., turn-around) when a whisker is touched)

Ear-Twitch (whether there is any reaction (e.g., turn-around) when an ear is touched)

Reaching (whether the mouse extends an arm to reach for a desk in sight when hung in midair; confirmation of visual perception)

Key Jangling (whether there is any reaction in response to a key jangling sound; confirmation of auditory perception and convulsion susceptibility).

For these criteria, all mice were found to be normal.

(iii) Grip Strength and Muscle Strength Check

Grip strength and muscle strength were measured to detect any abnormalities regarding grip strength and muscle strength using the following criteria.

Wire hang test (a wire net is turned over together with a mouse clinging to it)

Grip Strength test (a mouse clinging to a wire net is pulled to measure muscle strength)

The results of the above tests showed that there was no significant difference between the groups; more specifically, grip strengths and muscle strengths of all mice were normal.

(iv) Anxiety-Like Behavior

Light/dark preference test was conducted to examine anxiety-like behaviors. An apparatus containing a light box and a dark box with a merging point therebetween was prepared, and mice were placed in the dark box. Although mice usually prefer a dark environment, they move to the light box to explore the light box. During a 10-minute period, the time spent in the light box and the time spent in the dark box, the number of transfers between the light box and the dark box, the latent time before the first movement to the light box, and the travel distance were measured. A short amount of time spent in the light box, a small number of transfers between the light box and the dark box, a long latent time before the first movement to the light box, and the like were considered an indication of the development of anxiety-like behavior. The results of the experiments showed that there was no significant difference between the groups, and that there was no significant difference between the time spent in the light box and the time spent in the dark box. It was thus concluded that the development of anxiety-like behavior was not observed in any mice, i.e., the mice were habituated to the experiment environment and the experimenter.

Statistical Processing

Statistical processing of experiment data of mice behavior analysis was conducted using Stat View (SAS institute) statistics software. ANOVA assay (analysis of variance between multiple groups) was conducted for all five groups, and a group with a risk rate (p value) of less than 5% ($p<0.05$) was determined to have a significant difference. After determination of comparison subjects through ANOVA assay, multiple comparisons (post-hoc test) were performed according to Fisher's PLSD method.

Behavior Analysis Experiment 1: Rotor Rod Test

Figure 10:
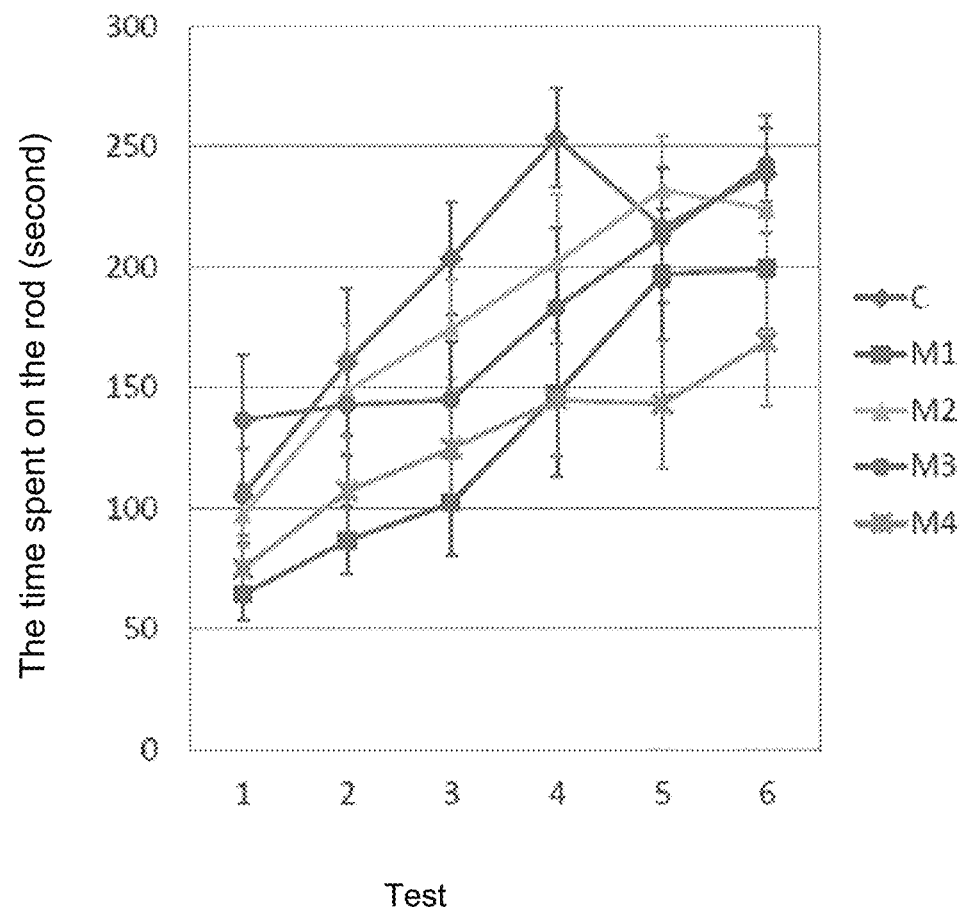
FIG. 10 shows the results of analysis of an effect of SNJ-1945 to improve motor learning ability of lissencephaly model mice by way of a rotor rod test. More specifically.
Figure 11:
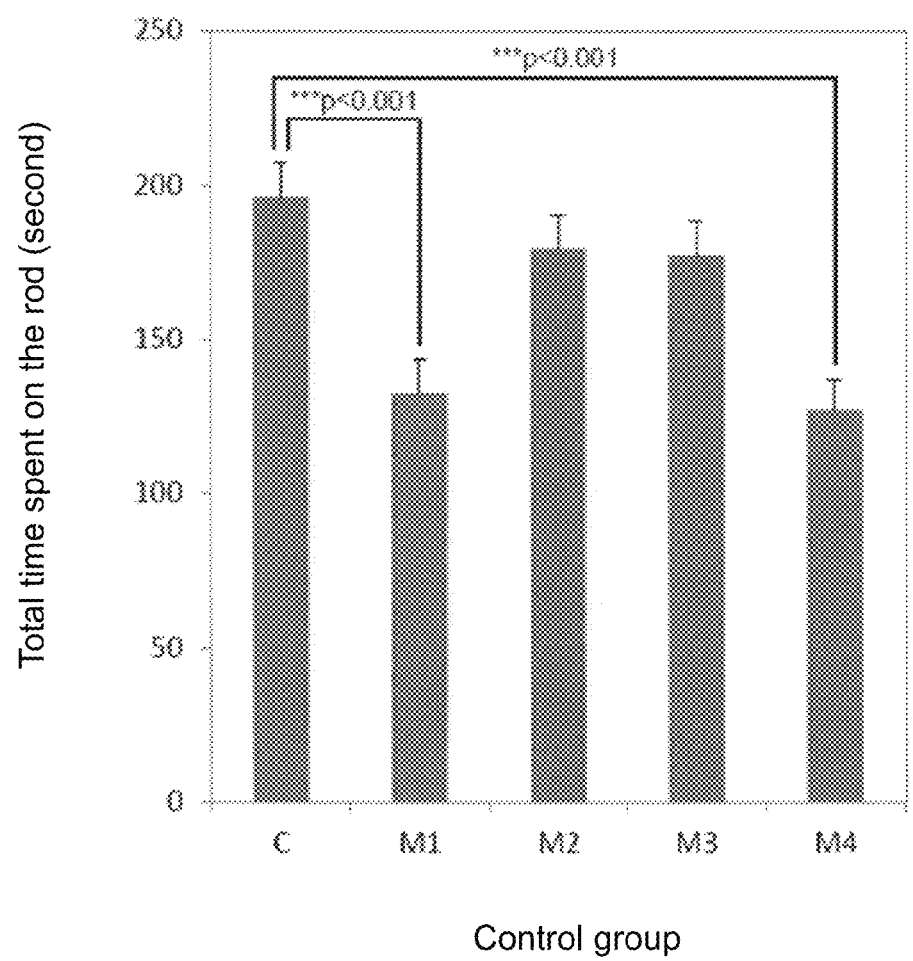
FIG. 11 shows the results of analysis of an effect of SNJ-1945 to improve motor learning ability of lissencephaly model mice by way of a rotor rod test. More specifically.

A rotor rod test was conducted as a motor coordination and motor learning test. The rotor rod test was performed as follows. An apparatus containing a cylindrical rod that rotates at a predetermined speed was prepared. A mouse was placed on the rod and, so as not to fall, started walking. The rod rotation speed was increased from 5 rpm to 40 rpm over 5 minutes. A single test was continued until the mouse fell from the rod, or until 5 minutes elapsed. The experiment was performed for two days, and three tests a day were conducted (6 tests in total). As the test was repeated, the mice became adept at staying on the rod. They did not easily fall, and stayed on the rod for a longer period of time. The mice with inferior motor learning ability did not increase their ability to stay on the rod; therefore, for them, the time spent on the rod did not increase. The results of the experiments showed that C group showed most significant motor improvement and the longest time spent on the rod (FIGS. 10 and 11). Compared with C group, M1 group was slow in motor leaning ability, and the time spent on the rod was significantly reduced. It was thus found that the motor learning ability was reduced in M1 group (FIGS. 10 and 11). For M2 and M3 groups with SNJ-1945 administration, the motor ability development curve was positioned between M1 group and C group (FIG. 10); their total time spent on the rod was increased to the extent that there was almost no significant difference from C group. It was thus confirmed that SNJ-1945 oral administration improved motor leaning ability (FIG. 11).

Behavior Analysis Experiment 2: Gait Analysis

A Gait Analysis for examining ambulation (footstep) was performed to find any abnormal motor functions or cerebellum deconditioning. More specifically, mice were made to walk on a transparent treadmill rotating at 24 cm/seconds, while pictures were taken from below using a high-speed camera (150 frames/second). The footprints of the mice were analyzed by dedicated software (DigiGait, Mouse Specifics, Inc.). Through this analysis, many characteristics were evaluated, including length of stride, angle of legs, and the method of setting/lifting the legs.

Main Items of Gait Analysis

Swing Duration: duration of time where a leg is up in the air

Figure 12:
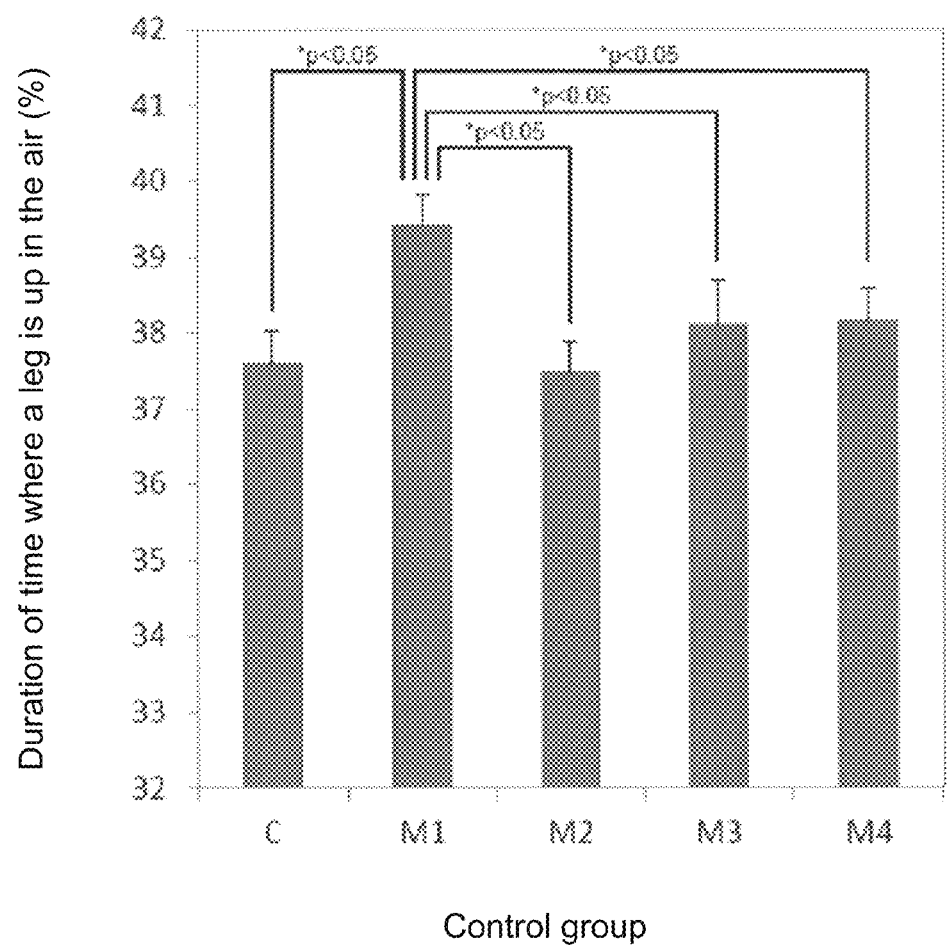
FIG. 12 shows the results regarding "% Swing" in Gait Analysis for testing an effect of SNJ-1945 to improve motor learning ability of lissencephaly model mice.
Figure 13:
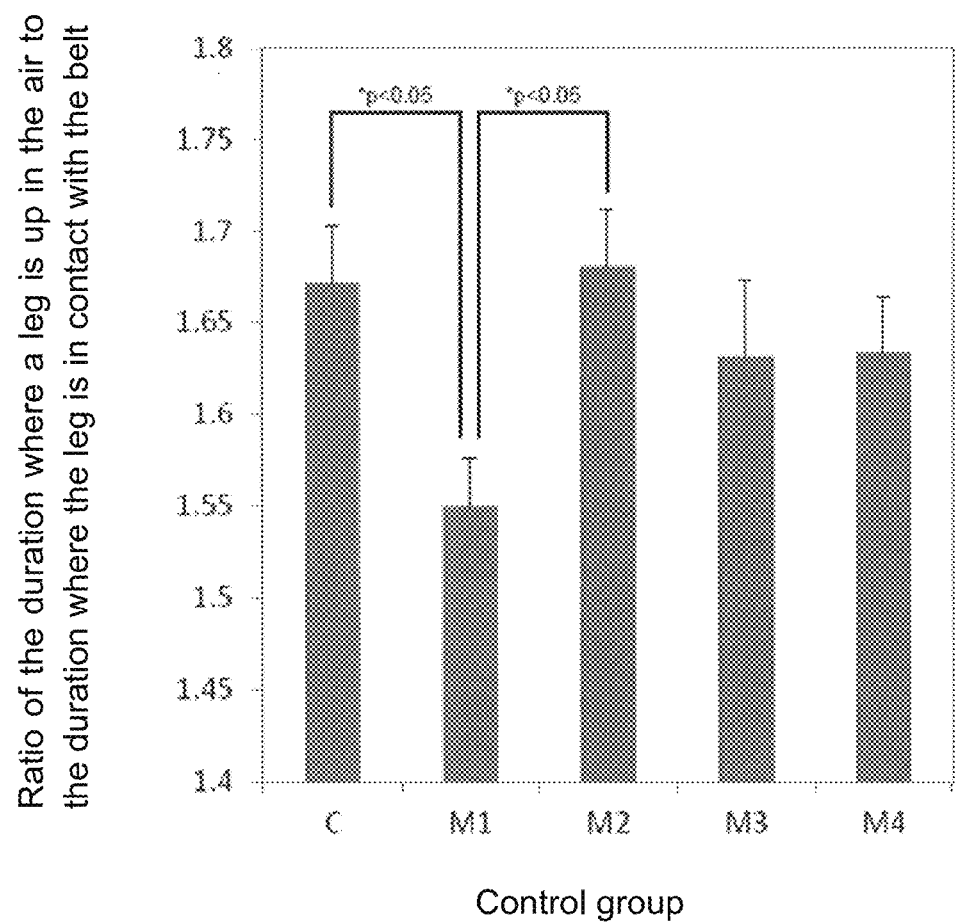
FIG. 13 shows the results regarding "Swing-to-stance-ratio" in Gait Analysis for testing an effect of SNJ-1945 to improve motor learning ability of lissencephaly model mice.

% Swing: percentage of duration of time where a leg is up in the air to take a step Braking Duration: duration from the time point where a leg touches the belt to the point where a leg completely comes in close contact with the belt % Braking: percentage of duration from the time point where a leg touches the belt to the point where a leg completely comes in close contact with the belt during the movement of taking a step % Brake of Stance: a percentage of duration from the time point where a leg touches the belt to the point where a leg completely comes in close contact with the belt during the movement where a leg is in contact with the belt Propulsion Duration: duration from the time point where a leg completely comes in close contact with the belt to the point where the leg is released from the belt % Propulsion: percentage of duration from the time point where a leg completely comes in close contact with the belt to the point where the leg is released from the belt during the movement of taking a step % Propel of Stance: percentage of duration from the time point where a leg completely comes in close contact with the belt to the point where the leg is released from the belt during the movement where the leg is in contact with the belt Stance Duration: duration where a leg is in contact with the belt % Stance: percentage of duration of time where a leg is in contact with the belt during the movement of taking a step Stride Duration: time taken to take a first step Swing-to-Stance Ratio: ratio of the duration where a leg is up in the air to the duration where the leg is in contact with the belt Significant differences were only observed in % Swing (percentage of duration where a leg is up in the air to take a step) and Swing-to-Stance Ratio (ratio of the duration where a leg is up in the air to the duration where the leg is in contact with the belt). Therefore, analysis was performed using these items. It is known that the % Swing value for animals with arthritis or the like is high, presumably because of uneven movement of their joints during the movement to take a step in the air. In comparison with C group, the % Swing of M1 group was significantly high, indicating abnormality in the function of taking a step (FIG. 12). For M2, M3, and M4 groups with SNJ-1945 administration, there was no significant difference compared with C group, and improvement in motor function was confirmed. Swing-to-Stance Ratio is known to change by a change in the way of walking; Swing-to-Stance Ratio becomes closer to 1 as the walking movement becomes closer to running. Compared with C group, the Swing-to-Stance Ratio of M1 group was significantly decreased, and was close to 1. In contrast, M2 group with SNJ-1945 administration was recovered to a level at which there was no significant difference with C group. M3 and M4 groups were also closer to 1 than M1 group (FIG. 13). The results showed that SNJ-1945 oral administration during embryonic period and prenatal period improves motor function.

Analysis of Cells Derived from Human Lissencephaly Patient

Gene Diagnosis of Human Lissencephaly Patient

Figure 14:
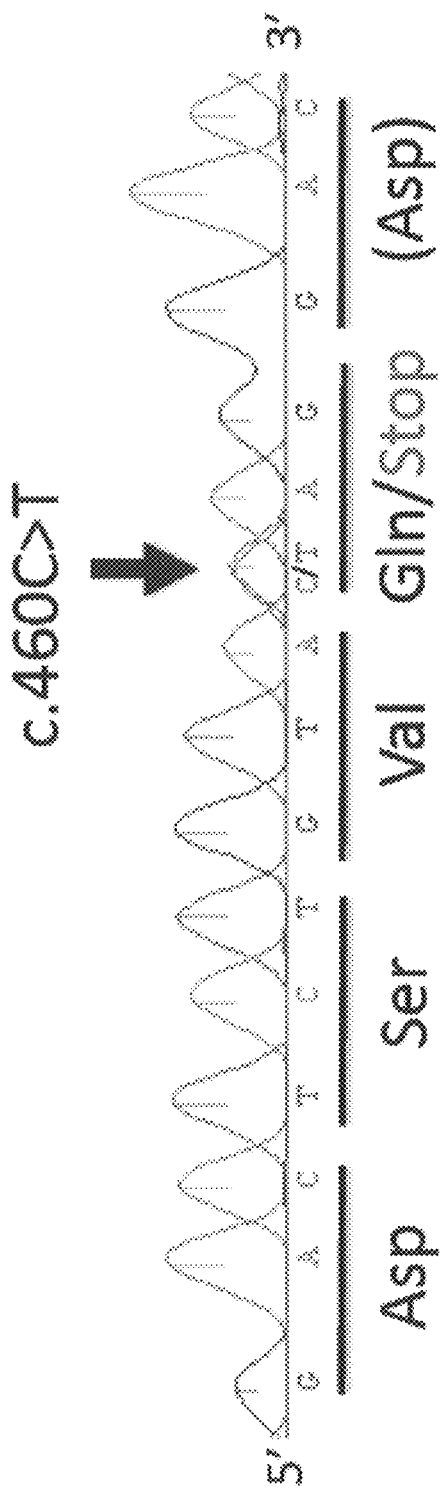
FIG. 14 shows the results of gene diagnosis (change in base sequence) of a human lissencephaly patient.

A 1 ml blood sample was taken from a lissencephaly patient and the parents, and the samples were subjected to centrifugation at 4° C., 3000 rpm using a 1.5 ml sample cup (Bio-BIK: SC-015). 50 µl of the surface layer of the resulting precipitate containing leukocytes was obtained and dissolved in 250 µl of a DNA extract buffer (10 mM Tris-HCl, pH 7.5, 0.5% sodium dodecyl sulfate, 10 mM ethylenediamine tetraacetic acid, Proteinase K 10 µg/ml (Roche 03-115-852-001)), and reacted for an hour at 37° C. After 100 µl of phenol and 100 µl of chloroform were added and intensively mixed, centrifugation was performed for 5 minutes at 4° C. and 15,000 rpm. 250 µl of the supernatant was transferred to a new 1.5 ml sample cup (Bio-BIK: SC-015), and µl of 3 M acetic acid sodium and 700 µl of ethanol were added and mixed, followed by centrifugation for 5 minutes at 4° C. and 15,000 rpm. The supernatant was discarded, and the precipitated DNA was dissolved in 100 µl of a dissolving buffer (10 mM Tris-HCl, pH 7.5, 1 mM ethylenediaminetetraacetic acid) to be used for gene diagnosis. The gene diagnosis was conducted by amplifying the gene by PCR using a primer with sequences of tctaaaatag ttatcctttg ttac and aggtgaataaaggaacactgtaca. 1 µl of DNA obtained from the patient, 1 µl of 10 mM dNTP, 1 µl of 100 µM primer, and 0.5 µl of BIOTAQ (Bioline Bio-21040) were added to 50 µl (in total) of a reaction solution, and amplification was conducted by performing 35 cycles of PCR for 20 seconds at 94° C., for 30 seconds at 55° C., and for 60 seconds at 72'C (Applied Biosystems Gene Amp 9700), thereby determining the base sequence of DNA. The determination of the base sequence was performed using Big Dye Terminator ver. 3.1 (Applied Biosystems #4336917) using a primer with sequences of tctaaaatag ttatcctttg ttac and aggtgaataaaggaacactgtaca. 35 cycles of PCR for 20 seconds at 94° C., for 30 seconds at 55° C., and for 4 minutes at 60° C. were performed (Applied Biosystems Gene Amp 9700), and the reaction product was deciphered using ABI 3500xL (Applied Biosystems). The results reveal that the 460th cytosine in the protein translation region was replaced with thymine. This generates a stop codon and stops protein translation, producing functionally inactive LIS1 (FIG. 14).

Establishment of Fibroblasts Derived from Human Lissencephaly Patient

The establishment of fibroblasts was performed in the following manner. Under a germ-free condition, a portion of epidermis (5 mm square) was obtained from a lissencephaly patient. The obtained epidermis was transported for 4 hours at room temperature while stored in a culture solution (E-MEM (Wako Pure Chemical Industries, Ltd., 051-07615), 10% fetal bovine blood serum (Equitech-Bio Inc, SFBM30-1798, 1×L-glutamine (Gibco, 25030), 1× Pen-Strep (Gibco, 15140)) (*the culture solution with this formulation is used hereinafter). After transportation, the tissue fragment was cut into a 1 mm square, fixed to a culture flask (Becton Dickinson 353009), and cultured for three weeks in 6 ml of a culture solution. After the 3-week culture, the amplification of fibroblasts from the tissue fragment was confirmed; then, the fragment was washed with a phosphate buffer physiological saline solution (phosphate buffered saline, PBS (−), 137 mM NaCl, 2.7 mM KCl, 10 mM $Na_2HPO_4$, 1.8 mM $KH_2PO_4$, pH 7.4), and 0.5 ml of trypsin-EDTA (Gibco, 25200) was added, followed by reaction for 5 minutes at 37° C. to separate the cells. Then, 10 ml of a culture solution was added, and the fragment was transferred to a 10 cm petri dish (Greiner, 664-160) for culture.

Fluorescence Cell Immunostaining

To observe the cells with a microscope, the cells were cultured on cover glasses. The cover glasses (24×24 No. 1, Matsunami Glass Ind., Ltd.) were immersed in 0.1 M hydrochloric acid for 20 minutes. After washing with water, the cover glasses were placed in 70% ethanol, and kept in a clean bench. In the clean bench, each cover glass was placed on the bottom of each well of a 6-well plate (Falcon 353046). After the ethanol was dried, $0.5 \times 10^5$ fibroblasts per well were added and cultured for 16 hours, thereby adhering the cells onto the cover glasses.

A SNJ-1945-containing culture solution was prepared. More specifically, SNJ-1945 dissolved in dimethyl sulfoxide (Sigma D-5879) was mixed with a culture solution so that the final concentration became 200 µM, and placed still for an hour at 37° C. to dissolve SNJ-1945 in a culture medium, thereby obtaining a SNJ-1945-containing culture solution. The SNJ-1945-containing culture solution was added to the cells cultured in the 6-well plate in an amount of 2 ml/well after the culture medium in the well was discarded, and culture was performed for two hours. As a control, a culture solution containing the same amount of dimethyl sulfoxide was cultured in the same manner.

After 2-hour culture, the cells were washed with a phosphate buffer physiological saline solution (phosphate buffered saline, PBS (−), 137 mM NaCl, 2.7 mM KCl, 10 mM $Na_2HPO_4$, 1.8 mM $KH_2PO_4$, pH 7.4), and 4% paraformaldehyde (PFA) in PBS (−) (Wako Pure Chemical Industries, Ltd., 163-20145) was added. The cells were immobilized by being left for 15 minutes at room temperature. The cells were then washed with PBS (−), and 0.2% Triton X-100 (polyoxyethylene (10) octylphenyl ether; Wako Pure Chemical Industries, Ltd., 168-11805) in PBS (−) was added. After being left for 10 minutes at room temperature, cell infiltration was performed. The cells were further washed with PBS (−), and a blocking solution (3% BSA (Sigma, A3156-5G), 4% Block Ace Powder (Yukijirushi Co., Ltd.) and PBS (−)) was added. The cells were left for an hour at room temperature, thereby blocking non-specific binding (blocking treatment). As the primary antibody, a supernatant obtained by 5-minute centrifugation at 4° C. and 15000 rpm, diluted 100-fold with a blocking solution, was used.

A parafilm was placed on a wet chamber, and 300 µl of an antibody solution was placed thereon. Each cover glass was placed on the antibody solution with the cell-adhering surface face-down, and was reacted by being placed still for an hour at room temperature. The cover glass with the cells adhered thereon was placed back in the 6-well plate containing PBS (−), and washed by being subjected to 5-minute shaking 4 times. For the secondary antibody and a nucleus-staining pigment 10 mM DAPI (4′,6-diamidino-2-phenylindole, Dojindo Molecular Technologies, Inc. 28718-90-3), a supernatant obtained from 5-minute centrifugation at 15000 rpm and 4° C. was diluted 1000-fold with PBS (−) (500-fold for DAPI), and added to the well in an amount of 1.5 ml per well. The well was blocked from light and the mixture reacted by being slowly shaken for an hour at room temperature. PBS (−) was added, and the cells were washed by repeating 5-minute shaking 4 times. 1 drop of an enclosed liquid (FluorSave Reagent, Calbiochem) was added to a slide glass (slide glass for fluorescence staining; S0318, Matsunami Glass Ind., Ltd.), and the cells were enclosed by placing a cover glass thereon with the cell-adhering surface face-down. To make it airtight, the periphery of the cover glass was sealed with lacquer. After the cells were fixed for about 30 minutes to 1 hour, the surface of the cover glass was cleaned with a rolling pin wet with water, and then cleaned with a rolling pin wet with ethanol, thereby obtaining an observation sample.

Table 2 below shows a list of antibodies used for fluorescence staining.

TABLE 2

| LIS1 | primary antibody | anti LIS1 rabbit antisera<br>anti γ-tubulin mouse IgG<br>(sc-17787, SANTA CRUZ) |
| --- | --- | --- |
|  | secondary antibody | anti rabbit IgG goat IgG-<br>AlexaFluor546 (A11010,<br>invitrogen)<br>anti mouse IgG donkey IgG-<br>AlexaFluor488 (A11055,<br>invitrogen) |
| dynein intermediate chain (DIC) | primary antibody | anti dynein 74k<br>intermediate chain mouse<br>IgG (MAB1618, CHEMICON)<br>anti γ-tubulin goat IgG<br>(sc-7396, SANTA CRUZ) |
|  | secondary antibody | anti mouse IgG goat IgG-<br>AlexaFluor546 (A11003,<br>invitrogen)<br>anti goat IgG donkey IgG-<br>AlexaFluor488 (A11055,<br>invitrogen) |
| β-COP | primary antibody | anti β-COP mouse IgG<br>(G6160, SIGMA-ALDRICH)<br>anti γ-tublin goat IgG<br>(sc-7396, SANTA CRUZ) |
|  | secondary antibody | anti mouse IgG goat IgG-<br>AlexaFluor546 (A11003,<br>invitrogen)<br>anti goat IgG donkey IgG-<br>AlexaFluor488 (A11055,<br>invitrogen) |

Observation of Confocal Microscope

The cells subjected to fluorescence immunostaining were observed using a confocal microscope (TCS FP5S, Leica). A fluorescence pigment was excited using 3 types of laser rays (Diode 405 nm; Argon 488 nm, output 30%; HeNe 543 nm), and the cells were observed using an oil immersion objective lens (HCX PL Apo lambda blue 63×1.4 oil). The images were taken by dedicated software (LAS AF, Leica) under the conditions of 2× zoom, 512×512 pixels, scan speed=400 Hz, and frame average=4. The cell boundary was obtained by simultaneously taking differential interference images. The obtained images were converted from LIF (Leica Image Format) to TIFF for image analysis. The analysis of the fluorescence microscope images was performed using Image J (NIH).

Figure 15:
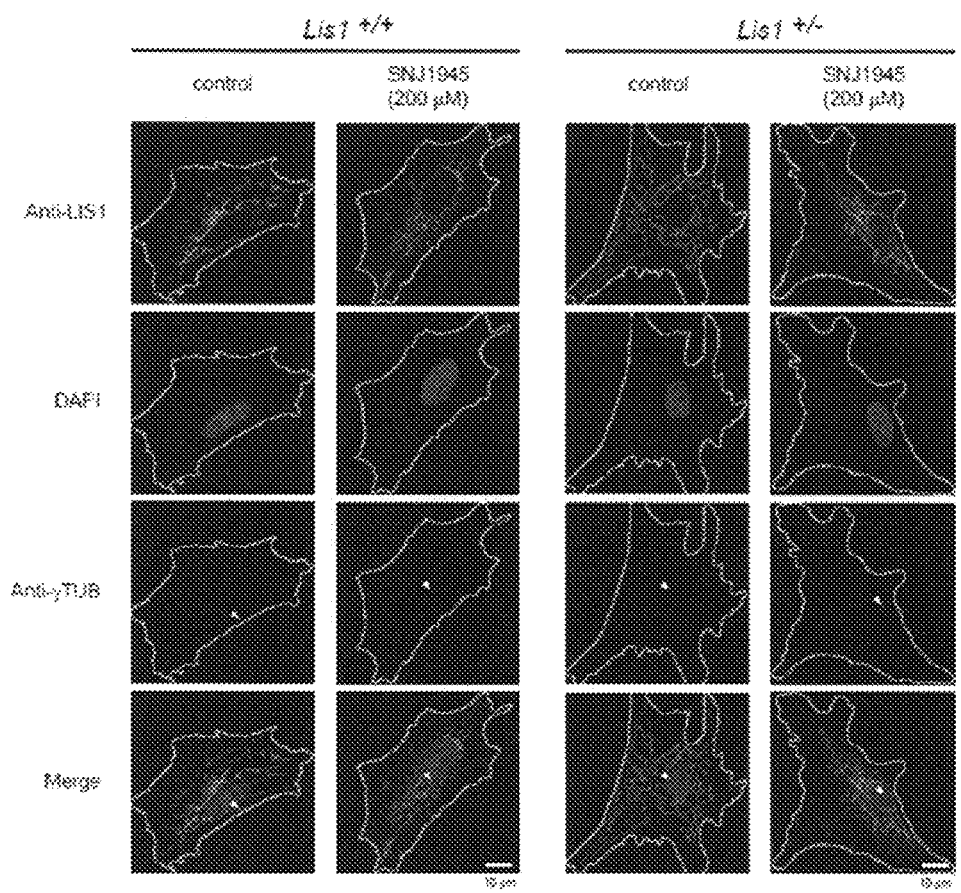
FIG. 15 shows the results of LIS1 detection by way of fluorescence immunostaining in normal human fibroblasts and fibroblasts derived from a human lissencephaly patient.
Figure 16:
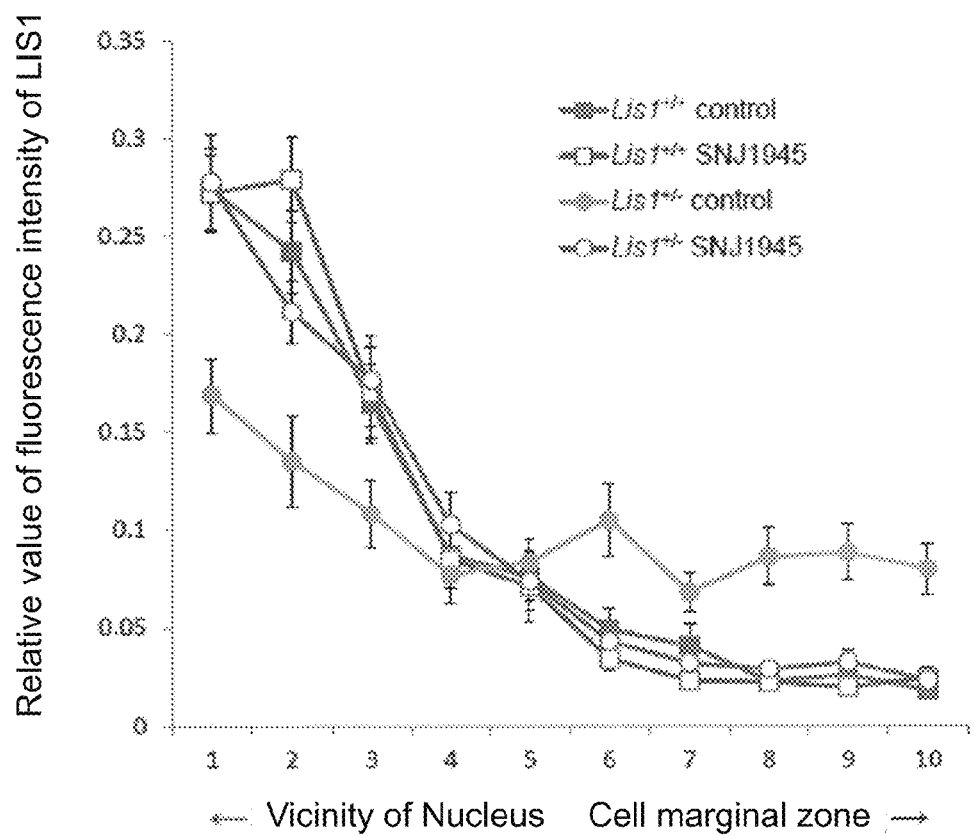
FIG. 16 shows the results of analysis of intracellular localization of LIS1, obtained by measuring fluorescence intensities at 10 points linearly from the nuclear marginal zone to the cellular marginal zone at equal intervals, based on the results of FIG. 15.

Distribution of LIS1: FIGS. 15 and 16

The intracellular distribution of LIS1 in the culture cells subjected to fluorescence-immunostaining using an anti-LIS1 antibody was observed. The observation showed that LIS1 was localized around the nucleus or centrosome in the normal Lis1 cells ($^{+/-}$), and is hardly present in the cell marginal zone. In Lis1 ($^{+/-}$) cells, the accumulation of LIS1 around the nucleus observed in Lis1 ($^{+/+}$) cells was not present, and LIS1 was evenly distributed from the region around the nucleus to the cell marginal zone. In particular, distribution along the cell marginal zone was prominently observed, although such distribution was hardly seen in Lis1 ($^{+/+}$) cells. It was confirmed that treating Lis1 ($^{+/-}$) cells with SNJ-1945 causes LIS1 to be accumulated around the nucleus or centrosome again as in Lis1 ($^{+/+}$). This reveals that a treatment using SNJ-1945 is capable of recovering the intracellular distribution of LIS1 in the cells derived from a human lissencephaly patient to the state of distribution in the normal LIS1.

Figure 17:
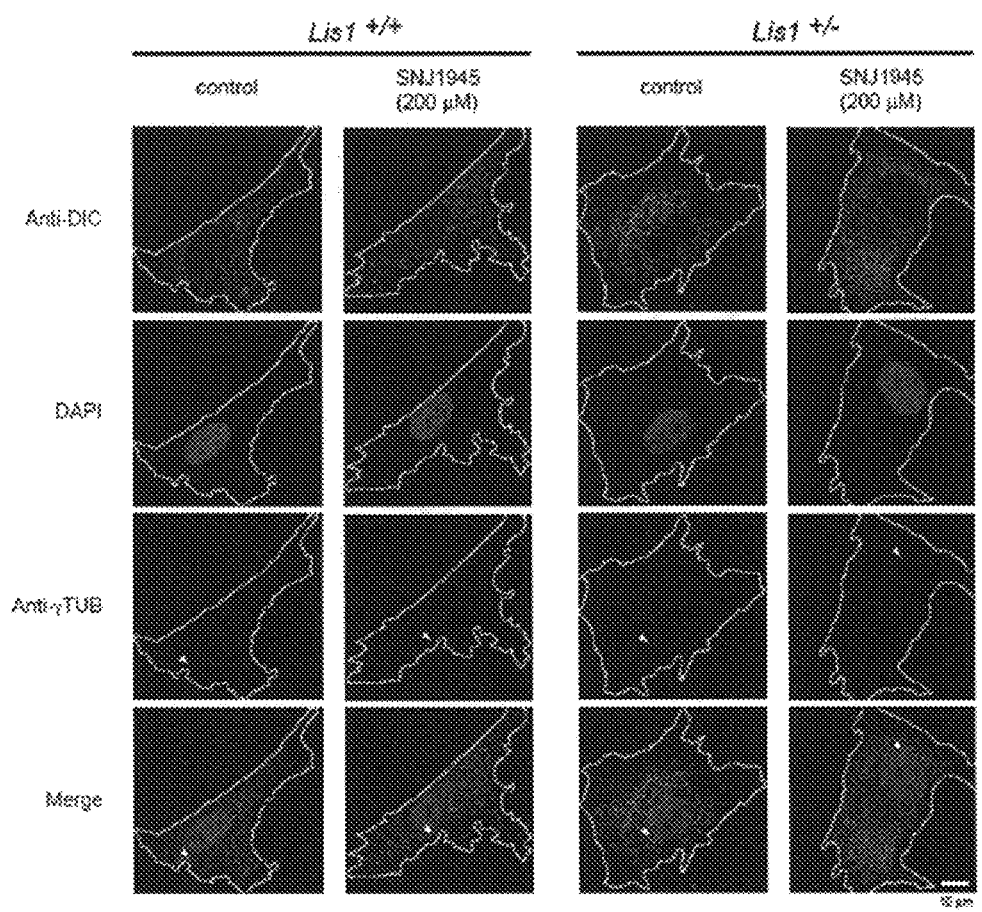
FIG. 17 shows the results of detection of cytoplasmic dynein by way of fluorescence immunostaining in normal human fibroblasts and fibroblasts derived from a human lissencephaly patient.
Figure 18:
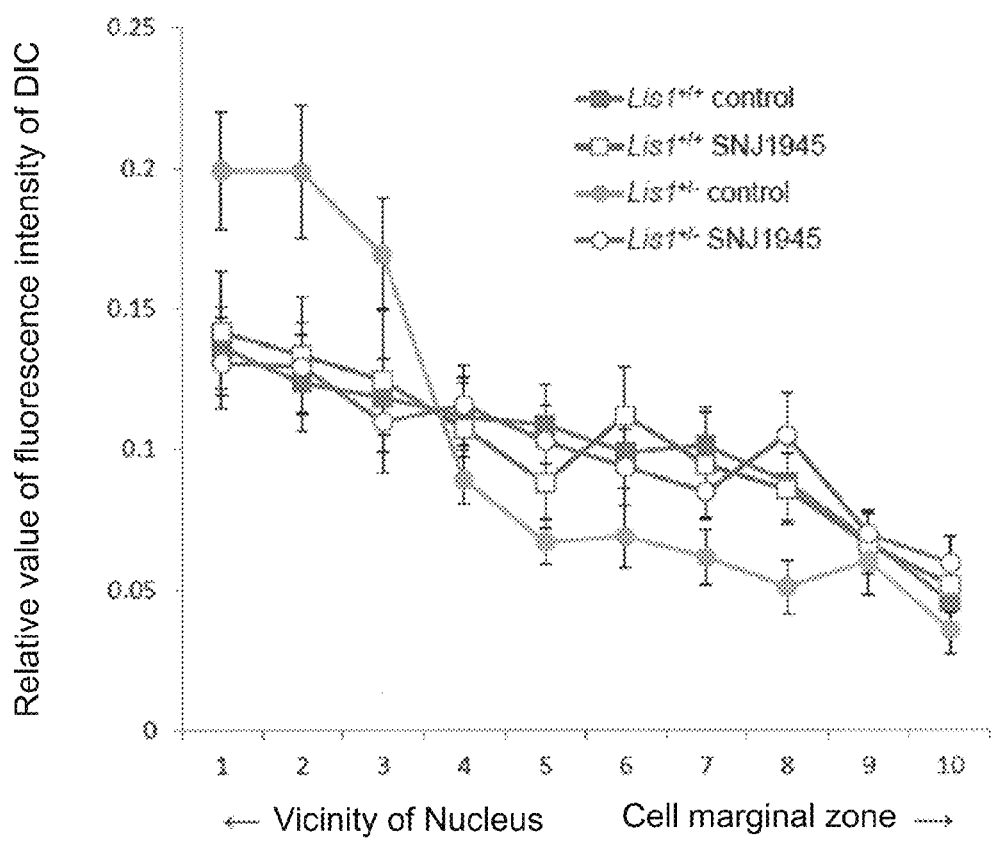
FIG. 18 shows the results of analysis of intracellular localization of cytoplasmic dynein, obtained by measuring fluorescence intensities at points linearly from the nuclear marginal zone to the cellular marginal zone at equal intervals, based on the results of FIG. 17.

Distribution of Cytoplasmatic Dynein: FIGS. 17 and 18

The intracellular distribution of the culture cells subjected to fluorescence-immunostaining using anti-DIC (cytoplasmatic dynein intermediate chain) antibody was observed.

The observation showed that, in normal Lis1 cells ($^{+/+}$), cytoplasmatic dynein was completely diffused from the region around the nucleus or centrosome to the cell marginal zone with a gentle gradient. In contrast, in Lis1 ($^{+/-}$) cells, the diffusion of cytoplasmatic dynein toward the marginal zone observed in Lis1 ($^{+/+}$) cells was not present, and cytoplasmatic dynein was intensively localized around the nucleus and centrosome. By treating the Lis1 ($^{+/-}$) cells with SNJ-1945, cytoplasmatic dynein became completely diffused again from the region around the nucleus to the cell marginal zone, as observed in Lis1 ($^{+/+}$). This reveals that a treatment using SNJ-1945 is capable of recovering the intracellular distribution of cytoplasmatic dynein in the cells derived from a human lissencephaly patient to the state of distribution in the normal cells.

Figure 19:
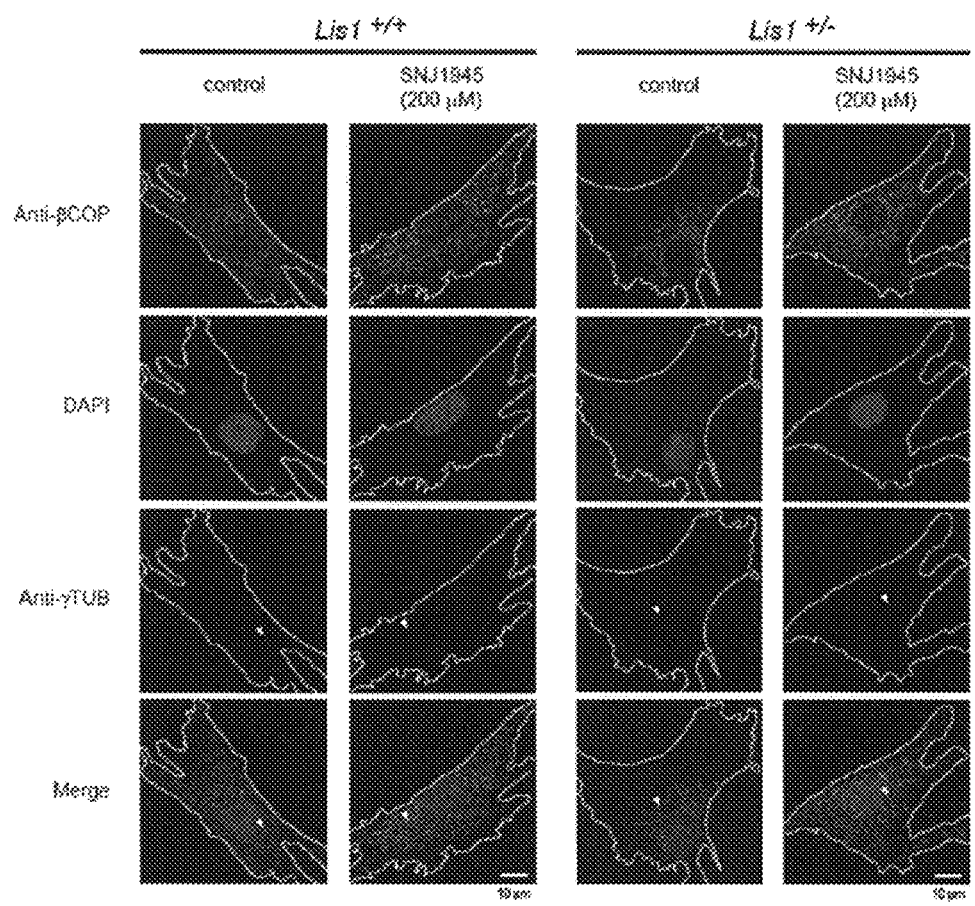
FIG. 19 shows the results of detection of β-COP small granule vesicles by way of fluorescence immunostaining in normal human fibroblasts and fibroblasts derived from a human lissencephaly patient.
Figure 20:
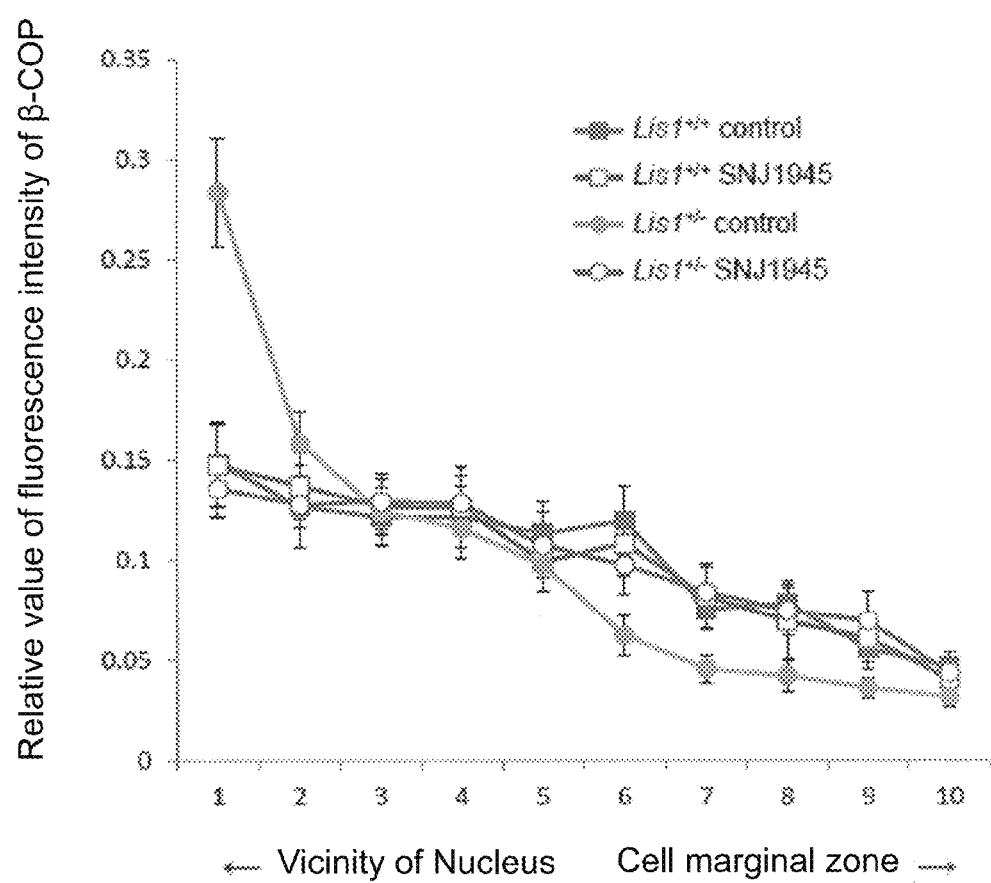
FIG. 20 shows the results of analysis of intracellular localization of β-COP small granule vesicles, obtained by measuring fluorescence intensities at 10 points linearly from the nuclear marginal zone to the cellular marginal zone at equal intervals, based on the results of FIG. 19.

Distribution of β-COP-Coated Vesicles: FIG. 19 and FIG. 20

The intracellular distribution of β-COP-coated vesicles was observed using an anti-β-COP antibody. The observation showed that, in normal Lis1 cells ($^{+/-}$), β-COP-coated vesicles were completely diffused from the region around the nucleus or centrosome to the cell marginal zone with a gentle gradient. In contrast, in Lis1 ($^{+/-}$) cells, the diffusion of β-COP-coated vesicles was not present except for the region around the nucleus; i.e., β-COP-coated vesicles were intensively localized in the region around the nucleus and centrosome. By treating the Lis1 ($^{+/-}$) cells with SNJ-1945, β-COP-coated vesicles became distributed evenly from the region around the nucleus to the cell marginal zone again, as observed in Lis1 ($^{-/+}$). This reveals that a treatment using SNJ-1945 is capable of recovering the intracellular distribution of β-COP-coated vesicles in the cells derived from a human lissencephaly patient to the state of distribution in the normal cells.

FIGS. 16, 18, and 20 are graphs showing the same results as in FIGS. 2b, 3b, and 4b. More specifically, the graphs were obtained in the following manner. In order to detect the intracellular locations of LIS1, cytoplasmatic dynein, and β-COP-coated vesicles, the fluorescence intensity was measured at 10 points linearly from the nuclear marginal zone to the cellular marginal zone at equal intervals. For each condition, 20 cells were measured; and the fluorescence intensities at the individual points were normalized based on the fluorescence intensity of all of the cells (=1), and plotted in a graph. The error bar denotes the standard error.

The LIS1 distribution was accumulated in the region around the nucleus in the normal cells, and is completely diffused in Lis1 ($^{+/-}$) cells. However, a treatment using SNJ-1945 recovers the state of accumulation in the region around the nucleus to the distribution state in the normal cells (FIG. 16). The cytoplasmatic dynein distribution and β-COP-coated vesicle distribution were diffused to the entire cell in the normal cells, and accumulated in the region around the cell nucleus in Lis1 ($^{+/-}$) cells. However, a treatment using SNJ-1945 recovered the accumulation state to the intracellular distribution in the normal cells (FIGS. 18 and 20).

Protein Quantitative Analysis
Preparation of Cell Extract

In a clean bench, the cells were placed in a 6-well plate in an amount of 3×10$^5$ cells per well and cultured for 16 hours, thereby adhering the cells to each well. The culture medium in the well was discarded, and the SNJ-1945-containing culture solution (the culture solution containing SNJ-1945-dissolved in Dimethyl Sulfoxide (Sigma, D-5879); final SNJ-1945 concentration=200μ) was added in an amount of 2 ml/well, and a 2-hour culture was performed. As a control, another culture was performed using a culture medium containing the same amount of Dimethyl Sulfoxide (Sigma, D-5879).

After 2-hour culture by adding SNJ-1945, the cells were washed twice with PBS (−), 500 μl of PBS (−), was added and the cells were scraped with a cell scraper. The scraped cells were collected to a 1.5 ml tube to be subjected to centrifugation for 5 minutes at 4° C. and 15000 rpm; the supernatant was discarded, and a cell precipitate was obtained. 500 μl of PBS (−) was added to the well with remaining cells (cells left after the scraping), and the remaining cells were scraped again with a cell scraper, and added to the precipitate. The resulting precipitate was subjected to centrifugation for 5 minutes at 4° C. and 15000 rpm; the supernatant was discarded, and a cell precipitate was obtained. Further, 500 μl of PBS (−) was added to the well with remaining cells (cells left after the scraping), and the remaining cells were collected and added to the precipitate. The resulting precipitate was subjected to centrifugation for 5 minutes at 4° C. and 15000 rpm; the supernatant was discarded, and a cell precipitate was collected.

70 μl of lysate buffer was added to each tube containing the collected cells, and the cells were dissolved by pipetting, thereby obtaining a cell suspension. The lysate buffer was prepared at time of use. The lysate buffer formulation is as follows.

20 mM Tris-HCl (2-Amino-2-hydroxymethyl-1,3-propanediol, pH 7.5, 100 mM NaCl, 5 mM EDTA, 0.1% Triton X-100, 10 μg/ml pepstatin A, μg/ml aprotinin, 10 μg/ml leupeptin, 1 mM PMSF (benzylsulfonyl fluoride, Sigma P7626-5G)

Next, each cell suspension was frozen by liquid nitrogen; afterward, the frozen cell suspension was dissolved again. The cell suspension was subjected to pipetting, and then to ultrasonic treatment to dissolve the cells. This series of processes including liquid nitrogen freezing, pipetting, and ultrasonic treatment was repeated three times. Thereafter, the cell liquid was subjected to centrifugation for 5 minutes at 4° C. and 15000 rpm, and the supernatant was collected in a new tube. The cell extract thus prepared was used for the experiment.

Western Blotting

The absorbency of the cell extract was measured, and the protein amount of the entire solution was determined. Bovine blood serum albumin (bovine serum albumin, BSA; Sigma, A3156-5G) dissolved in lysate buffer was used as a standard sample. 200 µl of Bradford reagent was placed in a 96-well plate, and 2 µl of cell extract was added. The absorbency at 595 nm was measured using an ARVO Sx (PerkinElmer) 96-well plate reader, and the entire protein amount was determined.

Then, SDS-PAGE was conducted. 10% polyacrylamide mini-slab gel was prepared, and the cell extract was mixed with a sample buffer (250 mM Tris-HCl, pH 6.8, 40% glycerol, 8% sodium dodecyl sulfate (SDS), 5% 2-mercaptoethanol, 5% bromophenol blue) at a ratio of 3:1. Based on the protein amount determined by the Bradford method, the cells were loaded to each well of the gel in an amount of 10 µg/well. At the same time, 5 µl of an electrophoresis protein marker (Precision Plus Protein Dual Color Standards 161-0373, Bio-Rad) was loaded to each well. Electrophoresis was performed using a migration buffer (25 mM tris, 192 mM glycine, 0.1% sodium dodecyl sulfate (SDS)) under the conditions of 20 mA, 85 minutes per mini-slab gel. The proteins were transferred from the electrophoresed gels to PVDF membranes (Immobilon-P IPVH00010, Millipore) under the conditions of 150 mA, 90 minutes. This transfer step was conducted using a transfer buffer having the following formulation.

Liquid A: 0.3 M Tris-HCl, pH 9.6, 0.02% SDS
Liquid B: 25 mM Tris-HCl, pH 10.2, 0.02% SDS
Liquid C: 25 mM Tris-HCl, pH 10.2, 0.02% SDS, 2 mM 6-aminohexanoic acid Blocking buffer (5% BSA, 4% Block Ace, 25 mM Tris-HCl, pH 7.6, 137.7 mM NaCl, 0.1% Tween-20) was added to the membranes to which the proteins were thus transferred in an amount of 30 ml per membrane, and shaken for an hour at room temperature, thereby blocking non-specific binding (blocking). The primary antibody used herein was prepared by diluting 100- to 300-fold a supernatant obtained by 5-minute centrifugation at 15000 rpm and 4° C., with a blocking solution. The primary antibody was reacted with the membranes for an hour in a wet chamber at room temperature. After the reaction with the primary antibody, the membranes were shaken in TTBS buffer (25 mM Tris, pH 7.6, 137.7 mM NaCl, 0.1% Tween 20) for 10 minutes, and the reacted membranes were washed three times. The secondary antibody was prepared by diluting 1000-fold, with TTBS, a supernatant obtained by 5-minute centrifugation at 15000 rpm and 4° C. The secondary antibody was reacted with the membranes for an hour in a wet chamber at room temperature. Thereafter, the reacted membranes were shaken in TTBS buffer for 10 minutes, and washed three times. The resulting membranes were shaken in Milli-Q water for three minutes, and washed three times. The membranes were then immersed in a coloring solution obtained by adding 1% of NBT/BCIP liquid (NBT/BCIP Stock Solution, Roche) to AP buffer (100 mM tris, pH 9.5, 100 mM NaCl, 5 mM $MgCl_2$) for 10 to 30 minutes to color the membranes. The resulting membranes were shaken in Milli-Q water for 3 minutes, and washed three times. Then, each membrane was dried by wrapping both surfaces with Kimtowels. Table 3 shows the primary antibody and the secondary antibody used for the above western blotting.

TABLE 3

| LIS1 | |
|---|---|
| primary antibody | anti LIS1 rabbit antisera |
| secondary antibody | anti rabbit IgG donkey IgG-Alkaline Phosphatase (711-055-152, Jackson Immuno Research) |
| dynein intermediate chain (DIC) | |
| primary antibody | anti dynein 74k intermediate chain mouse IgG (MAB1618, CHEMICON) |
| secondary antibody | anti mouse IgG goat IgG-Alkaline Phosphatase (115-055-044, Jackson Immuno Research) |
| β-actin | |
| primary antibody | anti β-actin mouse IgG (A2228, SIGMA-ALDRICH) |
| secondary antibody | anti mouse IgG goat IgG-Alkaline Phosphatase (115-055-044, Jackson Immuno Research) |

Figure 21:
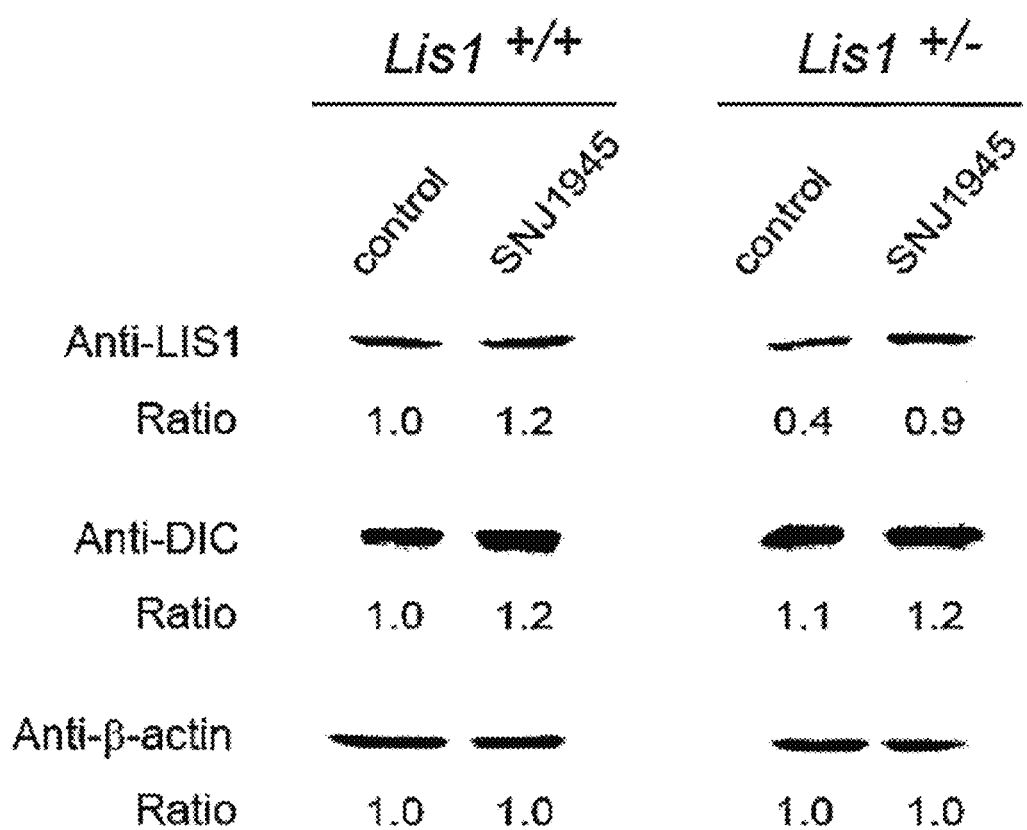
FIG. 21 shows the results of detection of LIS1, cytoplasmic dynein, and β-actin by way of western blotting in normal human fibroblasts and fibroblasts derived from a human lissencephaly patient.
Figure 22:
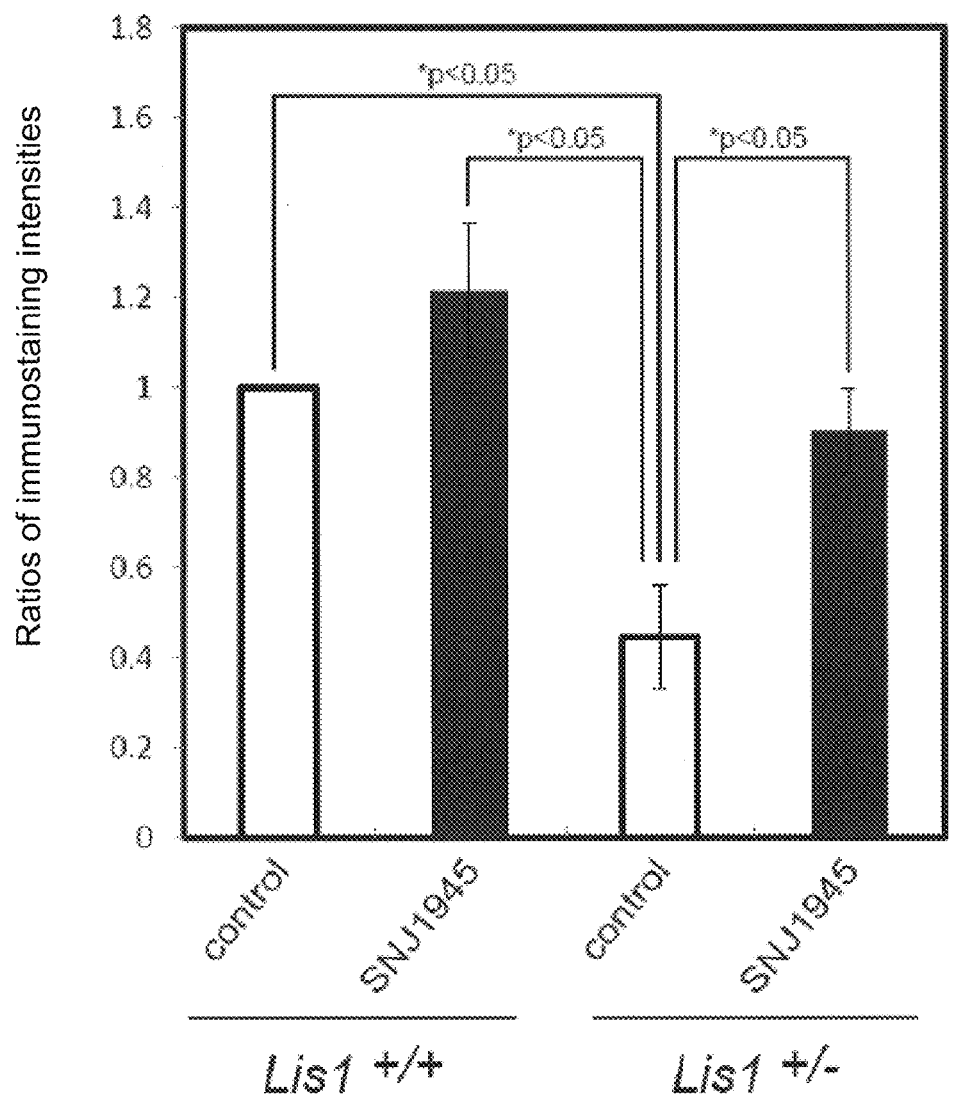
FIG. 22 is a graph showing the intensities of the bands of FIG. 21.

Using an LAS-3000 lumino image analyzer (Fujifilm Corporation), the dried membranes were analyzed, and the images were captured using dedicated LAS3000IR software (Fujifilm Corporation) in a Method-Digitize EPI mode under the following conditions: Exposure type=Precision, Exposure time=Auto, Sensitivity=Standard, and Brightness=5. The obtained images were stored in TIFF mode, and the absorbency of the band of the target protein was measured using dedicated MultiGauge ver. 3.1 image analysis software (Fujifilm Corporation). The total protein amount of each of LIS1, cytoplasmatic dynein and β-actin in the human fibroblasts was confirmed according to the bands obtained by western blotting (FIG. 21). Further, the average values of four experiments were plotted in a graph (FIG. 22: the error bar denotes the standard error, and a significance difference was found by conducting a t-test at a risk rate of 5%). The results showed that the LIS1 amount in the Lis1 ($^{+/-}$) cells were half or lower the LIS1 amount in normal cells (Lis1 ($^{+/+}$). The LIS1 amount after the drug treatment was recovered nearly to the extent of the LIS1 level in Lis1 ($^{+/+}$). The amount of cytoplasmatic dynein intermediate chain also increased. There was no change in amount of β-actin observed as a control protein. These results confirmed that inhibition of the function of calpain (protease) by SNJ-1945 suppresses degradation of LIS1, thereby increasing the LIS1 amount in the cells to the LIS1 level in the normal cells.

Analysis Using Calpain Inhibitor Other than SNJ-1945 (Reference Analysis Example)

Normal mice and Lis1 ($^{+/-}$) heterozygous mice (8 mice for each group) were raised by giving usual feed (CE-2, CLEA Japan, Inc.). At the age of 3 weeks, ALLN (Merck 208719) serving as a calpain inhibitor was dissolved in dimethyl sulfoxide in an amount of 10 mg/ml, and 40 µg of ALLN per gram of body weight was intraperitoneally injected to the mice. E64d (Roche 1585681) also serving as a calpain inhibitor was dissolved in dimethyl sulfoxide in an amount of 10 mg/ml, and 20 µg of E64d per gram of body weight was intraperitoneally injected to the mice (8 mice). At time points 6 hours and 24 hours after the injection, the mice were anesthetized and killed by cervical fracture, and the brain tissues were immediately isolated. To measure the LIS1 amount, the brain weight was measured immediately after the brain was isolated, and then completely solubilized by adding a protein dissolving buffer (30 mM Tris-HCl, pH 6.8, 1.5% sodium dodecyl sulfate (SDS), 0.3% bromophenol blue, 0.3% 2-mercapto-ethanol, 15% glycerol) in an amount twice the weight of the brain, followed by ultrasonic treatment. After 5-minute heat treatment at 95° C., 1 µl of the brain tissue-derived protein solution was isolated by 12.5% SDS-acrylamide electrophoresis, and LIS1 was detected by western blotting using an anti-LIS1 antibody. The antibodies in Table 3 were used. The structural formulas of ALLN and E64d are shown below.

[Chem. 79]

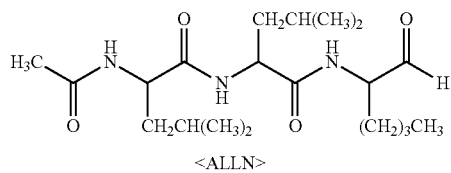

<ALLN>

[Chem. 80]

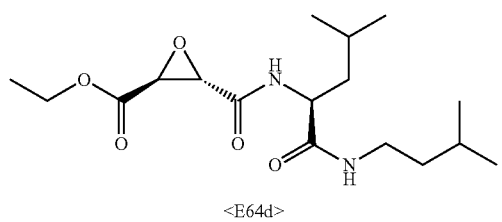

<E64d>

Figure 23A:
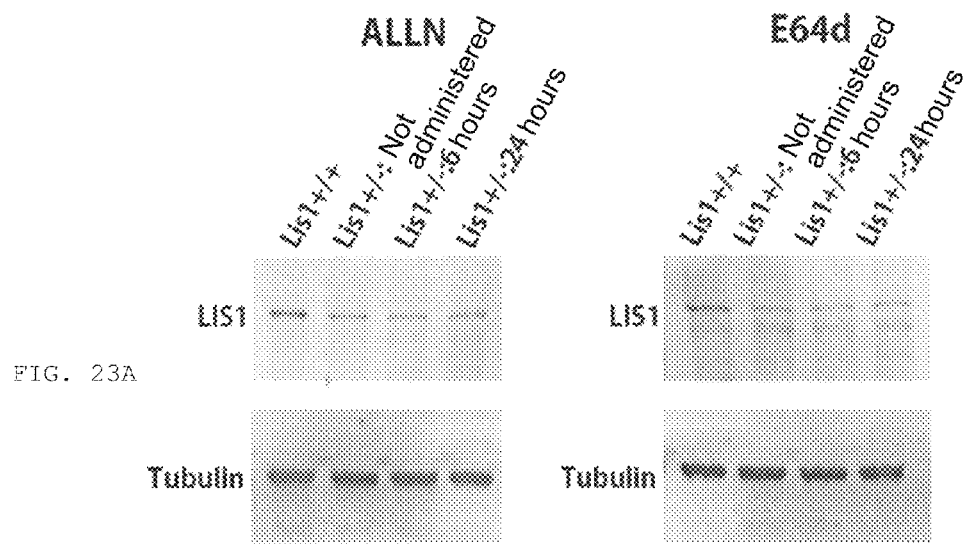
FIGS. 23A-23B show the results of analysis regarding recovery of LIS1 protein expression amount in lissencephaly model mice by administration of calpain inhibitors other than SNJ-1945.
Figure 23B:
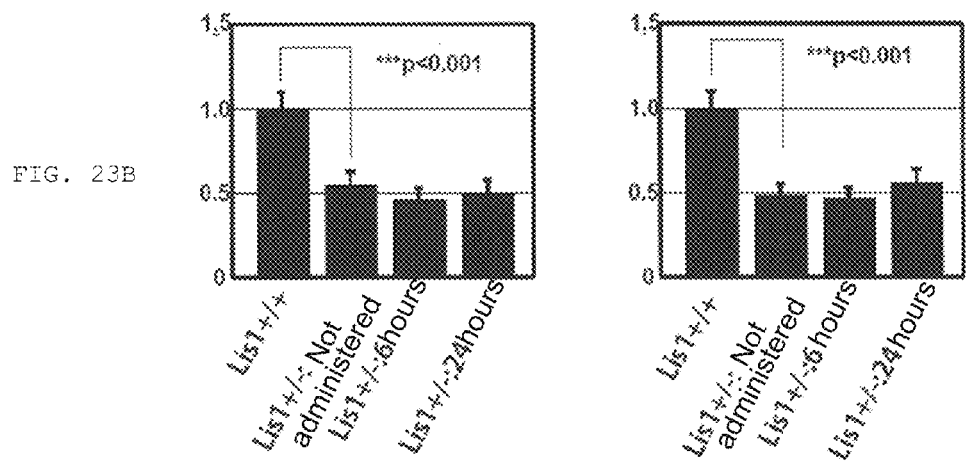

FIG. 23 shows the results. The results reveal that the LIS1 protein amounts of LIS1 heterozygous mouse embryos were about half the LIS1 protein amounts of normal mouse embryos. The LIS1 protein amount was not increased, even by the administration of ALLN or E64d; thus, it was revealed that ALLN and E64d presumably had no effect of treating lissencephaly.

Analysis of Toxicity of Calpain Inhibitors

The cerebellums were removed from 4- to 5-day-old FVB mice (15 mice). In a $Ca^{2+}$-free Hank's Balanced Salt Solution (CF-HBSS; $Ca^{2+}$, $Mg^{2+}$-free Hank's Balanced Salt Solution (CMF-HBBS, Sigma) containing 5 mM magnesium chloride ($MgCl_2$, Wako) and 4 mg/mL glucose (Wako)), the meninges were removed and cut into pieces. After the cerebellum fragments were washed with CF-HBSS, the fragments were allowed to stand for 20 minutes at 37° C. in CF-HBSS containing 0.025% trypsin (Invitrogen) and 6.25 µg/mL deoxyribonuclease (DNase, Sigma), and then centrifuged. The resulting tissues were washed with 10% HS/BME (DNase Medium; obtained by adding 5 mM $MgCl_2$ and 25 µg/mL DNase to Basal Medium Eagle (BME, Invitrogen) containing 10% Horse Serum (HS, Invitrogen)) and centrifuged. DNase medium was added to the cells, and the cells were transferred to a 24-well plate (Nunc). The cells were kept still for 30 minutes at 37'C under an atmospheric environment of 5% $CO_2$, thereby suspending the cells. The cell suspension was isolated, and then washed with 10% HS/BME. The suspension was transferred again to a 24-well plate to be cultured for 16 hours at 37° C. under an atmospheric environment of 5% $CO_2$. The cells were collected to BME containing 1% Bovine Serum Albumin (BSA, Sigma) and 0.5% $N_2$ supplement (Invitrogen), and the cell suspension was seeded on a 35 mm glass base dish (Iwaki) coated beforehand with poly-L-lysine (Sigma) and laminin (Sigma) in an amount of $5 \times 10^{-5}$ cells/mL. The cells were cultured for 8 hours at 37° C. under an atmospheric environment of 5% $CO_2$. The cultured nerve cells were used as test nerve cells.

Figure 24:
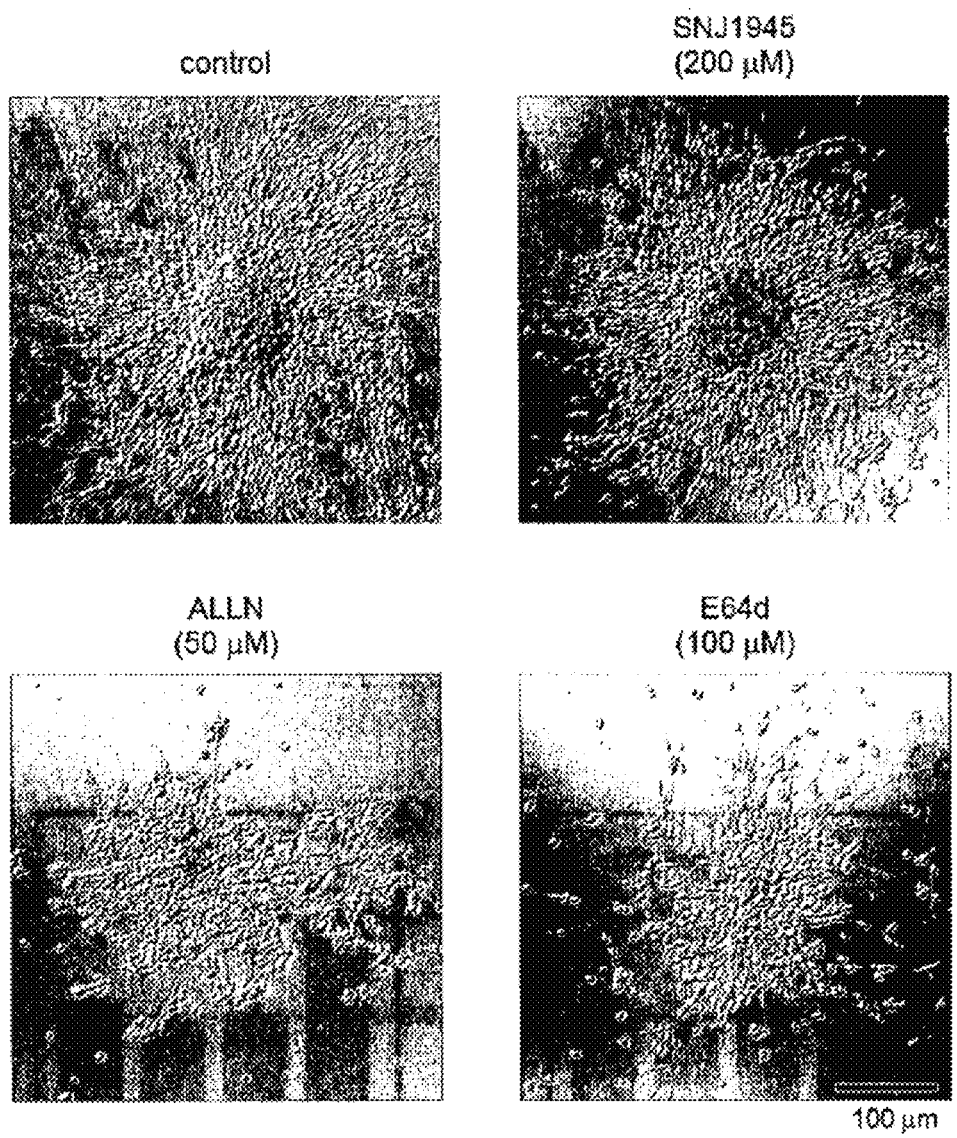
FIG. 24 shows the results of analysis of cytotoxicity of calpain inhibitors (SNJ-1945, E64d, and ALLN).

A culture solution (10% HS/BME) containing SNJ-1945, E64d, or ALLN was prepared in the following manner. SNJ-1945 dissolved in dimethyl sulfoxide (Sigma, D-5879) was mixed with a culture solution so that the final concentration became 200 µM, and was kept still for an hour at 37° C., thereby completely dissolving SNJ-1945 in the culture medium. ALLN and E64d were also dissolved in culture media in the same manner, except that ALLN and E64d were added to the culture media to final concentrations of 50 µM and 100 µM, respectively. The culture media in which the components were dissolved were added to the test nerve cells prepared above in an amount of 2 ml/well, and the cells were cultured for 16 hours. As a control, the same culture was conducted using a culture medium containing the same amount of dimethyl sulfoxide (Sigma, D-5879). After culture, the cells were observed using an inverted microscope (TCS FP5S, Leica). A 20× objective lens was used. Images were taken using dedicated software (LAS AF, Leica) under the condition of 512×512 pixels. FIG. 24 shows the results. As shown in FIG. 24, in the control cells containing only dimethyl sulfoxide (DMSO), normal neurite elongation and cell migration were observed, and the cells were diffused over the vicinity. In the cells containing SNJ1945, normal neurite elongation and cell migration were also observed, and no significant difference from the control was observed. In contrast, in the cells containing ALLN, the cells were roundly aggregated, neurite elongation was hardly observed, the cells remained accumulated in the center, and migration was hardly observed. Similarly, in the cells containing E64d, the cells were aggregated in the center, many cells were incapable of neurite elongation, little migration was observed compared with the control, and diffusion of the cells over the vicinity was very small.

These results showed that SNJ-1945 did not show any cell toxicity even in a high concentration, compared with other calpain inhibitors. Thus, high safety of SNJ-1945 with respect to the cells was confirmed.

The invention claimed is:

1. A method for treating lissencephaly comprising administering to a lissencephaly patient or a pregnant woman who is carrying a lissencephaly fetus, a compound represented by the general formula (I):

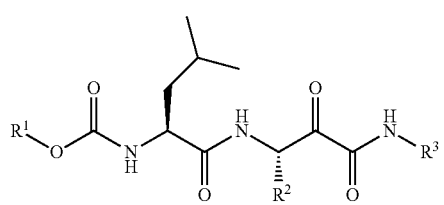

(I)

wherein $R^1$ is a linear or branched $C_{1-6}$ alkyl substituted with $C_{1-6}$ alkoxy; a linear or branched $C_{1-6}$ alkyl substituted with a heterocyclic group; a heterocyclic group, or a group represented by the formula (IIa):

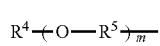

(IIa)

wherein $R^4$ is a linear or branched $C_{1-6}$ alkyl; $R^5$ is $C_{1-4}$ alkylene, and m is an integer of 1 to 6;

$R^2$ is a linear or branched $C_{1-6}$ alkyl optionally substituted with phenyl; and $R^3$ is a linear or branched $C_{1-6}$ alkyl optionally substituted with halogen, a $C_{1-6}$ alkoxy, or phenyl; a $C_{3-6}$ cycloalkyl optionally substituted with halogen, $C_{1-6}$ alkoxy, or phenyl; a condensed polycyclic hydrocarbon; or hydrogen.

2. The method according to claim 1, wherein $R^1$ is a group represented by the formula (IIb):

(IIb)

wherein n is an integer of 1 to 6.

3. The method according to claim 1, wherein $R^1$ is a group represented by the formula (IIa):

(IIa)

wherein, $R^4$ is a linear or branched $C_{1-6}$ alkyl, $R^5$ is $C_{1-4}$ alkylene, and m is an integer of 1 to 6.

4. The method according to claim 1, wherein $R^1$ is pyridyl optionally having $C_{1-3}$ alkyl.

5. The method according to claim 1, wherein $R^1$ is a heterocyclic group comprising oxygen heteroatom.

6. The method according to claim 1, wherein $R^3$ is cyclopropyl.

7. The method according to claim 1, wherein the compound represented by the general formula (I) is selected from the group consisting of ((1S)-1-(((1S)-1-benzyl-2,3-dioxo-3-(cyclopropylamino)propyl)amino)carbonyl)-3-methylbutyl)carbamic acid 2-methoxyethyl ester, ((1S)-1-(((1S)-1-benzyl-2,3-dioxo-3-(cyclopropylamino)propyl)amino)carbonyl)-3-methylbutyl)carbamic acid 5-methoxy-3-oxapentyl ester, ((1S)-1-((((1 S)-1-benzyl-2,3-dioxo-3-(cyclopropylamino)propyl)amino)carbonyl)-3-methylbutyl)carbamic acid 8-methoxy-3,6-dioxaoctyl ester, ((1S)-1-((((1S)-1-benzyl-2,3-dioxo-3-(cyclopropylamino)propyl)amino)carbonyl)-3-methylbutyl)carbamic acid 11-methoxy-3,6,9-trioxaundecanyl ester, and ((1S)-1-((((1S)-1-benzyl-3-(cyclopropylamino)-2,3-dioxopropyl)amino)carbonyl)-3-methylbutyl)carbamic acid 2-(pyridin-2-yl)ethyl ester.

8. The method according to claim 1, wherein the compound represented by the general formula (I) is ((1S)-1-((((1S)-1-benzyl-2,3-dioxo-3-(cyclobutylamino)propyl)amino)carbonyl)-3-methylbutyl)carbamic acid 5-methoxy-3-oxapentyl ester.

9. The method according to claim 1, wherein the compound represented by the general formula (I) is administered by oral administration.

10. The method according to claim 1, wherein the compound represented by the general formula (I) is administered by intravascular administration.

11. The method according to claim 1, wherein the compound represented by the general formula (I) is administered at a dose of 50 to 1,200 mg once every two to five days.

* * * * *